US012590077B2

(12) United States Patent
Nutt et al.

(10) Patent No.: US 12,590,077 B2
(45) Date of Patent: Mar. 31, 2026

(54) SHORT-ACTING MONOAMINE RELEASERS

(71) Applicant: Solvonis Therapeutics Ireland Holdings Limited, Dublin (IE)

(72) Inventors: David Nutt, London (GB); Alan Borthwick, London (GB); Robin Tyacke, London (GB)

(73) Assignee: Solvonics Therapeutics Ireland Holdings Limited, Dublin (IE)

( * ) Notice: Subject to any disclaimer, the term of this patent is extended or adjusted under 35 U.S.C. 154(b) by 0 days.

(21) Appl. No.: 18/729,953

(22) PCT Filed: Jan. 19, 2023

(86) PCT No.: PCT/EP2023/051249

§ 371 (c)(1),
(2) Date: Jul. 18, 2024

(87) PCT Pub. No.: WO2023/139163

PCT Pub. Date: Jul. 27, 2023

(65) Prior Publication Data

US 2025/0100990 A1 Mar. 27, 2025

Related U.S. Application Data

(60) Provisional application No. 63/301,055, filed on Jan. 19, 2022.

(51) Int. Cl.

*C07D 317/60* (2006.01)
*A61K 31/36* (2006.01)
*A61K 45/06* (2006.01)

(52) U.S. Cl.

CPC ............ *C07D 317/60* (2013.01); *A61K 31/36* (2013.01); *A61K 45/06* (2013.01)

(58) Field of Classification Search

None
See application file for complete search history.

(56) References Cited

U.S. PATENT DOCUMENTS

| | | | |
|---|---|---|---|
| 4,327,725 | A | 5/1982 | Cortese et al. |
| 4,624,848 | A | 11/1986 | Lee |
| 4,871,549 | A | 10/1989 | Ueda et al. |
| 4,968,509 | A | 11/1990 | Radebaugh et al. |
| 5,011,692 | A | 4/1991 | Fujioka et al. |
| 5,017,381 | A | 5/1991 | Maruyama et al. |
| 5,229,135 | A | 7/1993 | Philippon et al. |
| 5,260,068 | A | 11/1993 | Chen |
| 5,260,069 | A | 11/1993 | Chen |
| 5,456,923 | A | 10/1995 | Nakamichi et al. |
| 5,461,140 | A | 10/1995 | Heller et al. |
| 5,508,040 | A | 4/1996 | Chen |
| 5,516,527 | A | 5/1996 | Curatolo |
| 5,567,441 | A | 10/1996 | Chen |
| 5,622,721 | A | 4/1997 | Dansereau et al. |
| 5,686,105 | A | 11/1997 | Kelm et al. |
| 5,700,410 | A | 12/1997 | Nakamichi et al. |
| 5,837,284 | A | 11/1998 | Mehta et al. |
| 5,840,329 | A | 11/1998 | Bai |
| 5,977,175 | A | 11/1999 | Lin |
| 6,465,014 | B1 | 10/2002 | Moroni et al. |
| 6,875,751 | B2 | 4/2005 | Imbach et al. |
| 6,932,983 | B1 | 8/2005 | Straub et al. |
| 7,585,851 | B2 | 9/2009 | Bryant et al. |
| 7,964,580 | B2 | 6/2011 | Sofia et al. |
| 9,249,128 | B2 | 2/2016 | Cravatt et al. |
| 2020/0360311 | A1 | 11/2020 | Golan et al. |

FOREIGN PATENT DOCUMENTS

| | | | |
|---|---|---|---|
| CN | 107827989 | A | 3/2018 |
| CN | 113004201 | A | 6/2021 |
| WO | 2005058864 | A1 | 6/2005 |
| WO | 2008016677 | A2 | 2/2008 |
| WO | 2012131396 | A1 | 10/2012 |
| WO | 2021088805 | A1 | 5/2021 |

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113. (Year: 1989).*

Hood, Medications Used for Mental Health Illness, Understanding Pharmacology in Nursing Practice, 2020, 13, pp. 367-392. (Year: 2020).*

Miller GM. The Emerging Role of Trace Amine-associated Receptor 1 in the Functional Regulation of Monoamine Transporters and Dopaminergic Activity. Journal of Neurochemistry. 2011; 116:164-76.

Mitchell et al. MDMA-assisted therapy for severe PTSD: a randomized, double-blind, placebo-controlled phase 3 study. Nat Med. 2021;27(6):1025-1033.

Mithoefer M, MDMA-Assisted Psychotherapy: How Different is it from Other Psychotherapy?. Manifesting minds: A review of psychedelics in science, medicine, sex, and spirituality. 2013;125.

Mithoefer MC, et al., A Manual for MDMA-Assisted Therapy in the Treatment of Postraumatic Stress Disorder. 2017 Ver 8.1.

Mithoefer MC, et al., The safety and efficacy of ±3,4-methylenedioxymethamphetamine-assisted psychotherapy in subjects with chronic, treatment-resistant posttraumatic stress disorder: the first randomized controlled pilot study. J. of Psychopharmacology. 2010;25(4):439-452.

Morean ME, et al. The Drug Effects Questionnaire: Psychometric Support across Three Drug Types. Psychopharmacology (Berl). 2013;227(1):177-92.

(Continued)

*Primary Examiner* — Renee Claytor
*Assistant Examiner* — Andrew P Lee
(74) *Attorney, Agent, or Firm* — CALYX LAW LLP; Graham Pechenik

(57) ABSTRACT

Disclosed herein are novel 1,3-benzodioxole esters and their homologues, having various advantages over current compounds used in certain methods of drug-assisted therapy, such as MDMA, together with pharmaceutical compositions containing such 1,3-benzodioxole esters, and methods of their use to treat CNS disorders, and in particular mental health disorders.

20 Claims, No Drawings

(56) References Cited

OTHER PUBLICATIONS

Mukker et al. A Pro-Soft Drug Approach for Mitigation of Side Effects of Inhaled Corticosteroids. J Pharm Sci. 2016;105(9):2509-2514.
Nichols DE & Nichols CD, Serotonin Receptors. Chemistry Review; 2008, 108:1614-41.
Oehen P, et al. Pilot study of MDMA-assisted therapy for treatment-resistant PTSD. J Psychopharmacol. 2013. 27 (1):40-52.
Passie. Healing with Entactogens: Therapist and Patient Perspectives on MDMA-Assisted Group Psychotherapy, Torsten Passie. Multidisciplinary Association for Psychedelic Studies. 2012.
PCT/EP2023/051249. Information on Search Strategy. Mar. 17, 2023.
PCT/EP2023/051249. International Preliminary Report on Patentability. Jul. 23, 2024.
PCT/EP2023/051249. International Search Report. Mar. 17, 2023.
PCT/EP2023/051249. Written Opinion of the International Searching Authority. Mar. 17, 2023.
Pecherer et al. Darstellung und Eigenschaften verschiedener 3-Benzazocine, eine Klasse potentieller Analgetika [Synthesis and characteristics of various 3-benzazocines, a class of potential analgesics]. Helv Chim Acta. 1970;53 (4):763-770.
Rang HP, et al. Rang & Dale's Pharmacology 9th Edition. Elsevier Health Sciences. 2019.
Rautio et al. Prodrugs: design and clinical applications. Rautio et al., Nat Rev Drug Discov. 2008;7(3):255-70.
Ray TS, Psychedelics and the Human Receptorome, PloS one, 2010; 5(2), e9019.
Revel et al. TAAR1 activation modulates monoaminergic neurotransmission, preventing hyperdopaminergic and hypoglutamatergic activity. Proc Natl Acad Sci U S A. 2011;108(20):8485-8490.
Rickli et al. Receptor interaction profiles of novel psychoactive tryptamines compared with classic hallucinogens. Eur Neuropsychopharmacol. 2016;26(8):1327-1337.
Rogers G, et al., The Harmful Effects of Recreational Ecstacy: A Systematic Review of Observational Evidence. Health Technology Assessment, 2009; 13(6): iii-iv, ix-xii, 1-315.
Sandtner et al. Binding Mode Selection Determines the Action of Ecstasy Homologs at Monoamine Transporters. Mol Pharmacol. 2016;89(1):165-175.
Schenberg EE, Psychedelic-Assisted Psychotherapy: A Paradigm Shift in Psychiatric Research and Development. Frontiers in Pharmacology, 2018;9:733.
Schmid Y, et al. Acute subjective effects in LSD-and MDMA-assisted therapy. Journal of psychopharmacology, 2020. 1-13.
Sessa & Fischer. Underground MDMA-,LSD-and 2-CB-assisted individual and group psychotherapy in Zurich: Outcomes, implications and commentary. Drug Science, Policy and Law. 2015. 2.
Sessa B, et al. A Review of 3,4-methylenedioxymethamphetamine (MDMA)-Assisted Psychotherapy. Frontiers Psychiatry. 2019. 10:138.
Sessa. Why MDMA therapy for alcohol use disorder? And why now ?. Neuropharmacology. 2018;142:83-88.
Simmler et al. In Vitro Characterization of Psychoactive Substances at Rat, Mouse, and Human Trace Amine-Associated Receptor 1. J Pharmacol Exp Ther. 2016;357(1):134-144.
Simmler et al. Pharmacological characterization of designer cathinones in vitro. Br J Pharmacol. 2013;168 (2):458-470.
Thompson MR, et al. A role for oxytocin and 5-HT(1A) receptors in the prosocial effects of 3,4 methylenedioxymethamphetamine ("ecstasy"). Neuroscience; 2007. 146(2).
Tucker et al. The Demethylenation of Methylenedioxymethamphetamine ("Ecstasy") By Debrisoquine Hydroxylase (CYP2D6). Biochemical Pharmacology, 1994;47(7):1151-1156.
Williams FM. Clinical Significance of Esterases in Man. Clin Pharmacokinet., 1985; 10(5):392-403.
Xu et al. Antibody-catalyzed anaerobic destruction of methamphetamine. Proc Natl Acad Sci U S A. 2007;104 (10):3681-3686.
Zhang JH, et al. A Simple Statistical Parameter for Use in Evaluation and Validation of High Throughput Screening Assays. Journal of Biomolecular Screening. 1999;4(2):62-73.
Arza et al. AAPA PharmaSciTech., 2009;10(1):220-6.
Baggott MJ, et al. Effects of 3,4-methylenedioxymethamphetamine on socioemotional feelings, authenticity, and autobiographical disclosure in healthy volunteers in a controlled setting. Journal of Psychopharmacology. 2016;30 (4):378-87.
Baumann et al. Powerful cocaine-like actions of 3,4-methylenedioxypyrovalerone (MDPV), a principal constituent of psychoactive 'bath salts' products. Neuropsychopharmacology. 2013;38(4):552-562.
Berge et al., Pharmaceutical Salts. J.Pharm. Sci., 1977;66:1-19.
Bexis & Docherty. Role of alpha2A-adrenoceptors in the effects of MDMA on body temperature in the mouse. Br J Pharmacol. 2005;146(1):1-6.
Bhardwaj et al. Chemical delivery systems and soft drugs: Retrometabolic approaches of drug design. Saudi Pharm J. 2014;22(4):290-302.
Buchwald & Bodor. Recent advances in the design and development of soft drugs. Pharmazie. 2014;69 (6):403-413.
Buchwald P. Soft drugs: design principles, success stories, and future perspectives. Expert Opin Drug Metab Toxicol. 2020;16(8):645-650.
Carleton NB, et al. Brief Fear of Negative Evaluation Scale—Revisited. Depression and Anxiety. 2006;23:297-303.
Carvalho et al. Mechanisms Underlying the Hepatotoxic Effects of Ecstasy. Curr. Pharm. Biotechnol., 2010;11 (5):476-95.
Chemical Abstracts Service. 1506566-57-9.
Chemical Abstracts Service. 1889489-18-2.
De Gregorio et al. Hallucinogens in Mental Health: Preclinical and Clinical Studies on LSD, Psilocybin, MDMA, and Ketamine. J Neurosci. 2021;41(5):891-900.
De La Torre et al. MDMA, methamphetamine, and CYP2D6 pharmacogenetics: what is clinically relevant?. Front Genet. 2012;3:235.
De La Torre et al. Non-linear pharmacokinetics of MDMA ('ecstasy') in humans. Br J Clin Pharmacol. 2000;49 (2):104-109.
Di Cara B, et al. Genetic Deletion of Trace Amine 1 Receptors Reveals Their Role in Auto-Inhibiting the Actions of Ecstasy (MDMA). The Journal of Neuroscience. 2011;31(47):16928-40.
Di L. The Impact of Carboxylesterases in Drug Metabolism and Pharmacokinetics. Curr Drug Metab. 2019;20 (2):91-102.
Dimitrov et al. Ketamine esters and amides as short-acting anaesthetics: Structure-activity relationships for the side-chain. Bioorg Med Chem. 2019;27(7):1226-1231.
Dittrich A. The standardized psychometric assessment of altered states of consciousness (ASCs) in humans. Pharmacopsychiatry. 1998;31 Suppl 2:80-84.
Domes G, et al. Oxytocin Improves "Mind Reading" in Humans. Biological Psychiatry. 2007;61:731-3.
Dunlap LE, et al. Dark Classics in Chemical Neuroscience: 3,4-Methylenedioxymethamphetamine (MDMA). ACS Chem Neurosci. 2018;9(10):2408-27.
Franzer A & Hensler JG, Basic neurochemistry: principles of molecular, cellular, and medical neurobiology: Chapter 13. Lippincott Press; Philadelphia, PA. 1999.
Garcia-Alvarez et al. Studies on the uptake of glucose derivatives by red blood cells. ChemMedChem. 2007;2 (4):496-504.
Giovannitti JA, et al. Alpha-2 Adrenergic Receptor Agonists: A Review of Current Clinical Applications. American Dental Society of Anesthesiology. 2015;62:31-8.
Girault JA & Greengard P. The Neurobiology of Dopamine Signaling. Basic Science Seminars in Neurology. 2004;61(5):641-4.
Graeff et al. Role of 5-HT in Stress, Anxiety, and Depression. Pharmacology, Biochemistry, and Behavior. 1996; 54(1):129-41.
Greene TA & Wuts PGM, "Protective Groups in Organic Chemistry," (Wiley, 2nd ed. 1991).
Greer & Tolbert. A Method of Conducting Therapeutic Sessions with MDMA. Journal of Psychoactive Drugs, 1998; 30: 371-379.
Griffiths et al. Mystical-type experiences occasioned by psilocybin mediate the attribution of personal meaning and spiritual significance 14 months later. J Psychopharmacol. 2008;22(6):621-632.

(56) References Cited

OTHER PUBLICATIONS

Grof S. LSD Psychotherapy. 1980.
Harris DS, et al. "Subjective and hormonal effects of 3, 4-methylenedioxymethamphetamine (MDMA) in humans." Psychopharmacology 2002; 162:396-405.
Harrison IT & Harrison S, et al., "Compendium of Synthetic Organic Methods," 1971-1996 vols. 1-8 John Wiley and Sons.
Harvey et al. Development of Rapidly Metabolized and Ultra-Short-Acting Ketamine Analogs. Anesth Analg. 2015;121(4):925-933.
Holland J, et al., Ecstasy: The Complete Guide; A Comprehensive Look At The Risks And Benefits Of MDMA, 2001;82 n.2.
Huang et al. Isobologram Analysis: A Comprehensive Review of Methodology and Current Research. Front Pharmacol. 2019;10:1222.
Jaiswal M, et al., Nanoemulsion: an advanced mode of drug delivery system. Biotech., 2015; 3(5):123-7.
Johnson et al. Human hallucinogen research: guidelines for safety. J Psychopharmacol. 2008;22(6):603-620.
Jose et al. Structure-activity relationships for ketamine esters as short-acting anaesthetics. Bioorg Med Chem. 2013;21(17):5098-5106.
Kalant H. The pharmacology and toxicology of "ecstasy" (MDMA) and related drugs. CMAJ. 2001;165(7):917-928.
Mas et al. Cardiovascular and neuroendocrine effects and pharmacokinetics of 3,4-methylenedioxymethamphetamine in humans. J Pharmacol Exp Ther. 1999;290(1):136-145.
Katz et al. Characterizing the psychological state produced by LSD. J Abnorm Psychol. 1968;73(1):1-14.
Keller et al. The ethoxycarbonyl group as both activating and protective group in N-acyl-Pictet-Spengler reactions using methoxystyrenes. A short approach to racemic 1-benzyltetrahydroisoquinoline alkaloids. Beilstein J Org Chem. 2021;17:2716-2725.
Kernis MH & Goldman BM. A Multicomponent Conceptualization of Authenticity: Theory and Research. Advances in Experimental Social Psychology. 2006;38.
Kirsch P, et al. Oxytocin Modulates Neural Circuitry for Social Cognition and Fear in Humans. Journal of Neuroscience. 2005;25(49):11489-93.
Laizure et al. The role of human carboxylesterases in drug metabolism: have we overlooked their importance?. Pharmacotherapy. 2013;33(2):210-222.
Leary MR. A Brief Version of the Fear of Negative Evaluation Scale. Personality and Social Psychology Bulletin. 1983;9(3):371-5.
Liechti ME et al., Gender Differences in the Subjective Effects of MDMA. Psychopharmacology (Berl) 2001; 154 (2):161-8.
Liu & Li. TAAR1 in Addiction: Looking Beyond the Tip of the Iceberg. Front Pharmacol. 2018;9:279.
Llabres et al. Molecular basis of the selective binding of MDMA enantiomers to the alpha4beta2 nicotinic receptor subtype: synthesis, pharmacological evaluation and mechanistic studies. Eur J Med Chem. 2014;81:35-46.

* cited by examiner

SHORT-ACTING MONOAMINE RELEASERS

CROSS-REFERENCE

This application is a U.S. National Stage Entry under 35 U.S.C. § 371 of International Application No. PCT/EP2023/051249, filed Sep. 28, 2022, which claims priority under PCT Article 8(1) and Rule 4.10 to U.S. Provisional Application No. 63/301,055, filed Jan. 19, 2022, both of which are incorporated by reference for all purposes as if fully set forth herein.

FIELD OF THE INVENTION

Certain 1,3-benzodioxole esters and their homologues are disclosed, together with pharmaceutical compositions containing such compounds, and methods of their use to treat CNS disorders, and in particular mental health disorders.

BACKGROUND OF THE INVENTION

Mental health disorders are the leading cause of disability worldwide and are estimated to lead to over a million lives lost to suicide. Additionally, they are estimated to cost the global economy over $1 trillion in lost productivity each year. Mental health disorders are also highly correlated with substance abuse, poor educational attainment, unemployment, homelessness, and incarceration, all of which are associated with a 40% higher risk of developing cardiovascular and metabolic diseases, as well as other comorbidities. In the United States, mental health disorders are estimated to affect 1 in 5 adults and 1 in 6 children aged 6-17, totaling nearly 50 million people. Moreover, their incidence has been increasing over recent decades in all age groups, and is expected to increase yet further as a result of the ongoing COVID-19 pandemic.

Despite the high prevalence and increasing incidence, only half of all people with a mental health disorder receive treatment. Further, even for those who do receive treatment, the average delay between onset of symptoms and eventual treatment is 11 years. Myriad issues contribute to the failure of timely treatment; for example, half of U.S. counties do not have a single practicing psychiatrist, and a significant number of individuals lack insurance coverage. However, the primary reason why individuals fail to receive treatment is simply the absence of therapeutically effective treatment options available. Current treatment options for mental health disorders consist generally of psychotherapy, pharmacotherapy (typically, SSRIs), and direct brain intervention, either provided alone or in combination (e.g., psychotherapy together with one or more daily medications). All, however, suffer serious drawbacks.

The enormous public health burden of mental health disorders necessitates the development of novel alternative compounds, especially those which minimize side effects, optimize efficacy, and allow for greater access. Provided herein are compounds, compositions, methods, uses, and pharmaceutical kits to meet these needs and others, and having such advantages and improvements as will become readily apparent through the disclosure below.

INCORPORATION BY REFERENCE

Each patent, publication, and non-patent literature cited in the application or listed in the section titled "References" below, is hereby incorporated by reference in its entirety, as if each was incorporated by reference individually, and as if each is fully set forth herein. However, where such reference is made, and whether to patents, publications, non-patent literature, or other sources of information, it is for the general purpose of providing context for discussing features of the invention. Accordingly, unless specifically stated otherwise, the reference is not to be construed as an admission that the document or underlying information, in any jurisdiction, is prior art or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In a first aspect, provided is a compound having the structure of Formula (1):

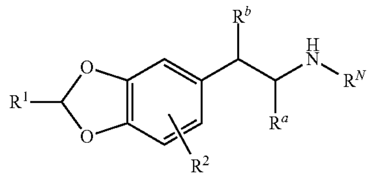

or a pharmaceutically acceptable salt thereof, wherein:

$R^1$ is H or Y; $R^2$ is H or Y; $R^a$ is X or Y; $R^b$ is H or Y; $R^N$ is methyl or Y;

X is H, methyl, or ethyl; and

Y is $-(CH_2)_n-CO_2R$, where n is an integer between 0 and 4 inclusive;

wherein R is alkyl, cycloalkyl, aryl, arylalkyl, $-(CH_2)_m Z(CH_2)_mCH_3$, or $-(CH_2)_mR^{cyc}$;

wherein Z is independently, and in either orientation, —O—, —C≡C—, —NH—, —NHNH—, —ONH—, —OCNH—, —CONH, —CH$(NH_2)$—, —OC(O)—, —S—, —S(O)—, $-SO_2-$, —CHF—, and $-CF_2-$;

$R^{cyc}$ is independently an optionally substituted aryl, an optionally substituted heterocycle, or an optionally substituted heteroaryl; and each m is independently between 0 and 4 inclusive;

wherein only one of $R^1$, $R^2$, $R^a$, $R^b$, $R^N$, or X is Y; and provided that the compound is not selected from the group consisting of:

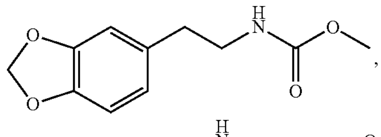

,

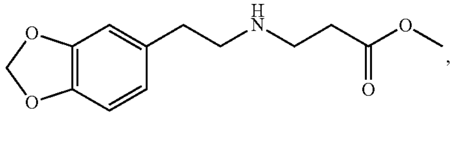

,

-continued

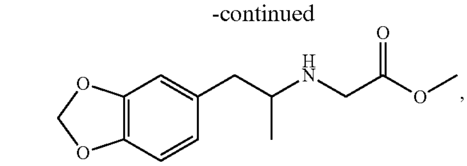

,

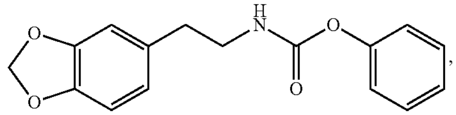

, and

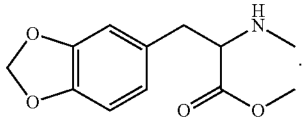

.

In some embodiments, the compound has the structure of any one of Formulas (I)-(V):

Formula (I)

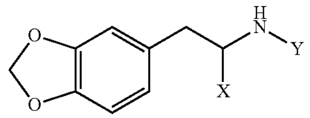

Formula (II)

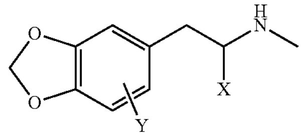

Formula (III)

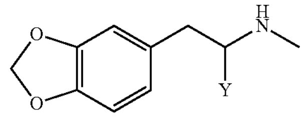

Formula (IV)

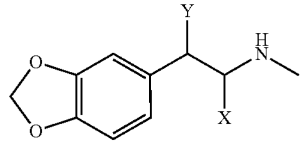

Formula (V)

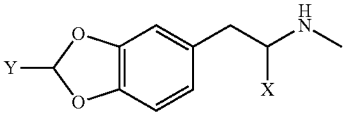

or a pharmaceutically acceptable salt thereof.

In some embodiments, the compound has the structure of Formula (I), or a pharmaceutically acceptable salt thereof. In some embodiments, the compound has the structure of Formula (II), or a pharmaceutically acceptable salt thereof.

In some embodiments, the compound has the structure of Formula (IIA), (IIA)

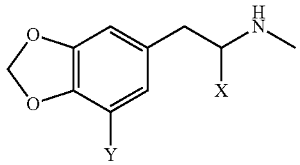

or a pharmaceutically acceptable salt thereof.

In some embodiments, X is methyl.

In some embodiments, the compound is selected from the group consisting of

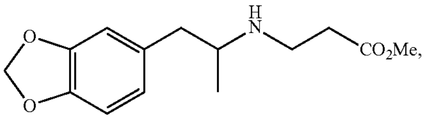

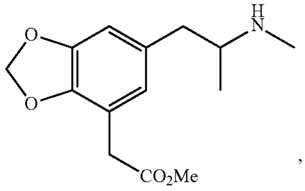

, or

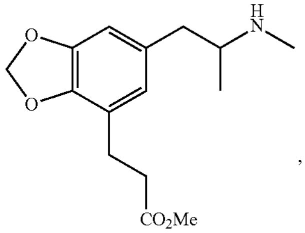

, or a pharmaceutically acceptable salt thereof.

In some embodiments, the compound is selected from the group consisting of

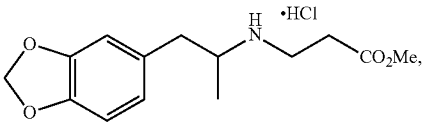

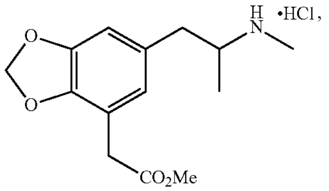

or

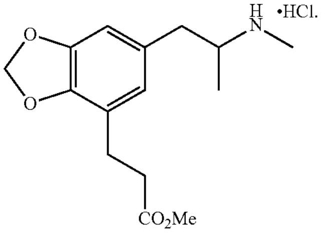

In another aspect, provided is a single enantiomer of the compound of any of the preceding embodiments.

In some embodiments (also and used equivalently for shorthand herein, "in embodiments"), the compound is classified as highly soluble in PBS pH 7.4. In some embodiments, the compound is classified as highly permeable, as determined by a MDR1-MDCKII permeability assay. In some embodiments, the compound is not determined to be a substrate for P-glycoprotein, as determined in the presence of a P-glycoprotein inhibitor or in mock MDCKII cells.

In some embodiments, the clearance rate of the compound is greater than the clearance rate of MDMA, as determined in human liver microsomes. In some embodiments, the half-life of the compound is shorter than the half-life of MDMA, as determined by a pharmacokinetic study in vitro or in vivo.

In some embodiments, the compound stimulates release of a monoamine neurotransmitter and inhibits the function of a monoamine transporter. In some embodiments, the compound stimulates release of a monoamine neurotransmitter or inhibits the function of a monoamine transporter. In some embodiments, the monoamine neurotransmitter is any of serotonin (5-HT), dopamine (DA), and norepinephrine (NE), and/or the monoamine transporter is any of a serotonin transporter (SERT), a dopamine transporter (DAT), and a norepinephrine transporter (NET).

In some aspects, the disclosed compounds are for use in modulating neurotransmission. In some embodiments, modulating neurotransmission treats a substance use disorder, a behavioral addiction, or a mental health disorder. In some aspects, the disclosed compounds are for use in the treatment of a substance use disorder, a behavioral addiction, or a mental health disorder. In some embodiments, the substance use disorder, the behavioral addiction, or the mental health disorder is any of alcohol use disorder, opioid use disorder, nicotine dependence, stimulant use disorder, tobacco use disorder, gambling addiction, gambling disorder, sexual addiction, gaming addiction, shopping addiction, internet addiction, binge eating disorder, internet gaming addiction, an anxiety disorder, a depressive disorder, or a trauma or stressor related disorder.

In some aspects are disclosed pharmaceutical compositions comprising a therapeutically effective amount of a disclosed compound for use in treating a substance use disorder, a behavioral addiction, or a mental health disorder, and a pharmaceutically acceptable carrier, diluent, or excipient. In some embodiments, the composition is suitable for oral, buccal, sublingual, injectable, subcutaneous, intravenous, or transdermal administration. In some embodiments, the composition is suitable for oral administration. In some embodiments, the composition is suitable for intravenous administration. In some embodiments, the composition is in a unit dosage form.

In some embodiments, the composition further comprises a therapeutically effective amount of an additional active agent. In some embodiments, the additional active agent is selected from the group consisting of: amino acids, antioxidants, anti-inflammatory agents, analgesics, antineuropathic and antinociceptive agents, antimigraine agents, anxiolytics, antidepressants, antipsychotics, anti-PTSD agents, cannabinoids, immunostimulants, anti-cancer agents, antiemetics, orexigenics, antiulcer agents, antihistamines, antihypertensives, anticonvulsants, antiepileptics, bronchodilators, neuroprotectants, entactogens and empathogens, entheogens, psychedelics, tryptamines, terpenes, beta-carbolines, phenethylamines, monoamine oxidase inhibitors, sedatives, stimulants, serotonergic agents, nootropics, and vitamins. In some embodiments, the additional active agent acts to increase a therapeutic effect, provide an additional therapeutic effect, decrease an unwanted effect, increase stability or shelf-life, improve bioavailability, induce synergy, or alter pharmacokinetics or pharmacodynamics. In some embodiments, the additional therapeutic effect is an antioxidant, anti-inflammatory, analgesic, antineuropathic, antinociceptive, antimigraine, anxiolytic, antidepressant, antipsychotic, anti-PTSD, immunostimulant, anti-cancer, antiemetic, orexigenic, antiulcer, antihistamine, antihypertensive, anticonvulsant, antiepileptic, bronchodilator, neuroprotective, entactogenic, empathogenic, entheogenic, psychedelic, nootropic, sedative, or stimulant effect.

In some embodiments, the additional active agent is selected from the group consisting of: opioid antagonists (e.g., nalmefene, naltrexone), CB-1 antagonists (e.g., rimonabant), CRH1 antagonists (e.g., verucerfont, pexacerfont), NK1R antagonists (e.g., tradipitant), OTR agonists (e.g., oxytocin), GABA agents (e.g., topiramate, baclofen, benzodiazepines, such as alprazolam, diazepam or lorazepam), voltage-gated sodium channel inhibitors (e.g., oxacarbazepine, valproic acid, zonisamide), voltage-dependent calcium channel agonists (e.g., gabapentin, pregabalin), α7 nicotinic acetylcholine (ACh) receptor agonists (e.g., varenicline), 5-HT3 antagonists (e.g., ondansetron), 5-HT1A receptor partial agonists (e.g., aripiprazole), 5-HT2A receptor antagonists (e.g., quetiapine, olanzapine, mirtazapine), 5-HT reuptake inhibitors (e.g., trazodone), SERT inhibitors (e.g., duloxetine), al adrenoreceptor antagonists (e.g., doxazosin, prazosin), glucocorticoid receptor antagonists (e.g., mifepristone), al adrenoreceptor agonists (e.g., guanfacine), AChE inhibitors (e.g., citicoline), dopamine D2 receptor antagonists (e.g., tiapride), α2 adrenoreceptor agonists (e.g., clonidine), NMDA receptor antagonists (e.g., acamprosate), and aldehyde dehydrogenase inhibitors (e.g., disulfiram), including pharmaceutically acceptable salts.

In some aspects are disclosed unit dosage forms comprising a therapeutically effective amount of a disclosed compound. In some embodiments, the unit dosage form is formulated for oral administration. In embodiments, the unit dosage form is formulated for immediate release, controlled release, sustained release, extended release, or modified release. In embodiments, the unit dosage form is formulated for intravenous administration. In embodiments, the unit dosage form comprises the compound in a total amount of between 1 and 100 mg. In embodiments, the unit dosage form comprises the compound in a total amount of between 5 and 50 mg.

In some aspects are disclosed methods for modulating neurotransmission in a mammal, comprising administering to the mammal a therapeutically effective amount of a disclosed compound, composition, or unit dosage form. In some embodiments, the neurotransmission is serotonergic neurotransmission. In some embodiments, the neurotransmission is dopaminergic neurotransmission. In some embodiments, modulating neurotransmission comprises one or more of: (a) stimulating release of serotonin, and/or reducing serotonin uptake, by inhibiting the function of a serotonin transporter (SERT); and (b) stimulating release of dopamine, and/or reducing dopamine uptake, by inhibiting the function of a dopamine transporter (DAT). In some embodiments, the neurotransmission comprises reduced peak norepinephrine levels relative to peak serotonin levels and/or peak dopamine levels. In some embodiments, the neurotransmission is noradrenergic neurotransmission. In some embodiments, noradrenaline levels are increased from baseline following administration of the compound in a microdialysis assay. In some embodiments, the increase in noradrenaline levels from baseline is reduced relative to an increase in noradrenaline levels produced by MDMA or MEAI in a microdialysis assay. In some embodiments, modulating neurotransmission treats a substance use disorder, a behavioral addiction, or a mental health disorder in the mammal.

In some embodiments, the compound or the composition is orally administered to a mammal or a subject. In some embodiments, the compound or the composition is intravenously administered to the mammal or the subject.

In some aspects are disclosed methods of treating a medical condition in a mammal in need of such treatment, comprising administering a disclosed compound, composition, or unit dosage form. In some embodiments, the medical condition is a disorder linked to dysregulation or inadequate functioning of neurotransmission. In some embodiments, the disorder is linked to dysregulation or inadequate functioning of neurotransmission is that of serotonergic neurotransmission. In embodiments, the medical condition is a substance abuse disorder, a behavioral addiction, or a mental health disorder. In embodiments, the mammal is a human.

In some aspects are disclosed methods of reducing the symptoms of a substance use disorder, a behavioral addiction, or a mental health disorder in a human, comprising identifying a human in need of said reducing, and administering to the human a disclosed compound, composition, or unit dosage form. In some aspects are disclosed methods of treating a substance use disorder patient, a behavioral addiction patient, or a mental health patient in need thereof, comprising administering to the patient a therapeutically effective amount of a disclosed compound, composition, or unit dosage form.

In some embodiments, the substance abuse disorder, behavioral addiction, or mental health disorder is selected from the group consisting of: alcohol use disorder, nicotine dependency, opioid use disorder, stimulant use disorder, sedative, hypnotic, or anxiolytic use disorder, tobacco use disorder, gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technological addictions, post-traumatic stress disorder (PTSD), an anxiety disorder, a depressive disorder, adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders. In some embodiments, the substance abuse disorder is any of alcohol use disorder, nicotine dependence, sedative, hypnotic, or anxiolytic use disorder, opioid abuse disorder, stimulant use disorder, and tobacco use disorder. In some embodiments, the behavioral addiction is any of gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, and technology addiction. In some embodiments, the mental health disorder is any of an anxiety disorder, a depressive disorder, OCD, or PTSD. In some embodiments, the anxiety disorder is generalized anxiety disorder (GAD). In some embodiments, the depressive disorder is major depressive disorder (MDD) or treatment-resistant depression (TRD).

In some aspects are disclosed methods of improving psychological functioning in a human, comprising identifying a human in need of said improving, and administering to the human a disclosed compound, composition, or unit dosage form. In some embodiments, the improvement in psychological functioning is a reduction of neuroticism or psychological defensiveness, an increase in creativity or openness to experience, an increase in decision-making ability, an increase in feelings of wellness or satisfaction, or an increase in ability to fall or stay asleep.

In some embodiments, the compound is administered in combination with one or more psychotherapy sessions. In embodiments, the patient has successfully completed a group therapy preparation course prior to the one or more psychotherapy sessions. In embodiments, the patient has met all predefined inclusion criteria, and the patient has not met any predefined exclusion criteria, prior to the one or more psychotherapy sessions. In some embodiments, the one or more psychotherapy sessions is between 5 and 20 psychotherapy sessions, during which at least two of said psychotherapy sessions the patient is administered the compound. In some embodiments, the method of the invention results in one or more of: (a) a reduction of substance use, (b) a reduction of substance cravings, (c) a promotion of substance abstinence, (d) a prevention of relapse, or (e) an improvement of at least one symptom of the substance use disorder. In some embodiments, the method of the invention results in one or more of: (a) an increase in quality of life, (b) an increase in psychosocial functioning, (c) a decrease in use or frequency of a prescription medication, (d) a decrease in use or frequency of a recreational drug, (e) a decrease in obsessive compulsive thoughts, (f) a decrease in suicidality, (g) an increase in feelings of empathy, or (h) an increase in self-compassion. In some embodiments, the method of the invention results in an improvement of at least one symptom of a comorbid psychiatric disorder, such as antisocial personality disorder, borderline personality disorder, depression, anxiety, schizophrenia, attention deficit hyperactivity disorder, bipolar disorder, obsessive compulsive disorder, binge eating disorder, or PTSD. In some embodiments, the results are measured at least 1 month, at least 3 months, at least 6 months, at least 9 months, or at least 1 year from baseline, or from the first psychotherapy session.

In some embodiments, the patient is also administered a therapeutically effective amount of an additional active agent selected from the group consisting of: an opioid antagonist (e.g., nalmefene, naltrexone), a CB-1 antagonist (e.g., rimonabant), a CRH1 receptor antagonist (e.g., verucerfont, pexacerfont), a NK1R antagonist (e.g., tradipitant), an OTR agonist (e.g., oxytocin), a GABA agent (e.g., topiramate, baclofen, a benzodiazepine, such as alprazolam, diazepam or lorazepam), a voltage-gated sodium channel inhibitor (e.g., oxacarbazepine, valproic acid, zonisamide), a voltage-dependent calcium channel agonist (e.g., gabapentin, pregabalin), an $\alpha$7 nicotinic acetylcholine receptor agonist (e.g., varenicline), a 5-HT3 antagonist (e.g., ondansetron), a 5-HT1A receptor partial agonist (e.g., aripiprazole), a 5-HT2A receptor antagonist (e.g., quetiapine, olanzapine, mirtazapine), a 5-HT reuptake inhibitor (e.g., trazodone), a SERT inhibitor (e.g., duloxetine), an $\alpha$1 adrenoreceptor antagonist (e.g., doxazosin, prazosin), a glucocorticoid receptor antagonist (e.g., mifepristone), an $\alpha$1 adrenoreceptor agonist (e.g., guanfacine), an AChE inhibitor (e.g., citicoline), a dopamine D2 receptor antagonist (e.g., tiapride), an $\alpha$2 adrenoreceptor agonist (e.g., clonidine), an NMDA receptor antagonist (e.g., acamprosate), an aldehyde dehydrogenase inhibitor (e.g., disulfiram), and pharmaceutically acceptable salts thereof.

In some embodiments, the patient has a genetic variation associated with a mental health disorder, SUD, AUD, trauma or stressor related disorder, depression, or anxiety, and including a genetic variation in mGluR5 or FKBP5. In some embodiments, the patient has a genetic variation associated with the metabolism of ester bonds, including metabolism in the plasma, gut, liver, or other tissues, such as a polymorphism relating to an endogenous esterase. In some embodiments, the patient has AUD, nicotine dependency, opioid use disorder, sedative, hypnotic, or anxiolytic use disorder, stimulant use disorder, or tobacco use disorder. In some embodiments, the patient has gambling disorder, compulsive sexual behavior, sexual addiction, gaming addiction, shopping addiction, internet addiction, kleptomania, pyromania, compulsive buying, pornography addiction, binge eating disorder, internet gaming addiction, exercise addiction or overtraining syndrome, love addiction, work addiction or workaholism, or technology addiction. In some embodiments, the patient has a depressive disorder or an anxiety disorder.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims. It also will be appreciated that headings within this document are being utilized only to expedite its review by a reader. They should not be construed as limiting the invention in any manner.

DETAILED DESCRIPTION OF THE INVENTION

While various aspects and features of certain embodiments are summarized above, the following detailed description illustrates several exemplary embodiments in further detail to enable one of skill in the art to practice such embodiments, and to make and use the full scope of the invention claimed. Described examples are provided for illustrative purposes and are not intended to limit the scope of the invention or its applications. It will be understood that many modifications, substitutions, changes, and variations in the examples, embodiments, applications, and details of the invention can be made by those skilled in the art without departing from the spirit of the invention, or the scope of the invention as described in the appended claims.

It will be appreciated that the headings herein are being utilized only to expedite its review by a reader. They must not be construed as limiting the invention or its equivalents in any manner.

Among aspects of the invention are novel drug compounds that act as monoamine releasing agents. Among other aspects of the invention are novel drug compounds that act as monoamine uptake inhibitors. Among other aspects of the invention are novel drug compounds that act as receptor agents, such as receptor agonists or partial agonists, at monoamine receptors. Among yet other aspects are pharmaceutical compositions and methods for the treatment of CNS disorders relating to or affected by one or more monoamine neurotransmitter systems, such as mental health conditions and mental disorders, and psychiatric and neuropsychiatric disorders.

The scope of the invention includes all embodiments and formulations thereof, not only those expressly described below, and it will be understood that many modifications, substitutions, changes, and variations in the described embodiments, applications, and details of the invention illustrated herein can be made by those skilled in the art without departing from the spirit of the invention, or the scope of the invention as set forth in the appended claims.

As mentioned, there is a significant need for therapeutically effective mental health treatment options. One such promising emerging therapeutic option is that of 3,4-methylenedioxymethamphetamine (MDMA) which, in human clinical studies currently underway, has started to accumulate evidence demonstrating that the Schedule I controlled drug has rapid and long-lasting therapeutic effects in treating mental health disorders following only limited doses when taken in combination with psychotherapy.

MDMA is a member of a pharmacological class called empathogens, or entactogens, that have demonstrated antidepressant, anxiolytic, and prosocial effects. These effects are believed to be produced or mediated, at least in part, by promoting raised levels of the monoamine neurotransmitters serotonin (5-HT), dopamine (DA), and norepinephrine (NE), by increasing activity at $5\text{-HT}_{1A}$ and $5\text{-HT}_{1B}$ receptors (Graeff et al., Pharmacol. Biochem. Behav., 54(1):129-41, 1996), and by acting at $5\text{-HT}_2$ receptors See, e.g., Rang et al., Rang & Dale's Pharmacol Elsevier Health Sciences. 2014; 177-196; Nichols & Nichols, Chemical reviews, 2008; 108 (5), 1614-1641; Frazer & Hensler J G (1999). Chapter 13: Serotonin Receptors. In Siegel G J, Agranoff B W, Albers R W, Fisher S K, Uhler M D (eds.). Basic Neurochemistry: Molecular, Cellular, and Medical Aspects. Philadelphia: Lippincott-Raven. pp. 263-292; Girault, J. A., & Greengard, P. 2004; 61(5), 641-644; Liechti et al., Psychopharmacol. (Berl), 154(2):161-8, 2001; see also Bexis and Docherty, Br. J. Pharmacol., 146(1):1-6, 2005; Giovannitti et al., Anesth. Prog., 62(1):31-9, 2015; Thompson et al., Neurosci., 146 (2):509-14, 2007; Kirsch et al., J. Neurosci., 25(49):11489-93, 2005; Domes et al., Biol. Psychiatry., 61(6):731-3, 2007; Ray, Plos One, 5(3):10, 2010; see Table 5 and accompanying text in Dunlap et al., ACS Chem Neurosci. 2018 Oct. 17; 9(10):2408-2427).

The term "empathogen" ("generating a state of empathy") was independently suggested in 1983-84 by the psychologist and psychopharmacologist Ralph Metzner, and the Purdue University professor of pharmacology and medicinal chemistry David Nichols, who in 1986 also coined the term "entactogen" ("to touch within") (Holland et al., Park Street Press, 2001 at 182 n.2). True to their names (used interchangeably herein), empathogens and entactogens such as MDMA can increase compassion for the self and others, reduce psychological defenses and fear of emotional injury, and enhance levels of trust and the capacity for introspection and communication. In part due to such effects, MDMA has been granted "breakthrough therapy" designation by the U.S. Food and Drug Administration (FDA).

In a recent randomized, double-blind, placebo-controlled, multi-site phase 3 clinical trial, in research sponsored by the Multidisciplinary Association for Psychedelic Studies, MDMA-assisted therapy was highly efficacious in individuals with severe PTSD, and treatment was safe and well-tolerated, even in those with comorbidities (Mitchell et al., Nat. Med., 27, 1025-1033, 2021). Studies have also demonstrated potential for MDMA to address other difficult-to-treat mental health conditions, including, among others, substance abuse, obsessive compulsive disorder (OCD), phobias, eating disorders, depression, end-of-life anxiety, and social anxiety.

Although MDMA generally produces no long-lasting or serious adverse events, it is known to cause transient adverse events that are mild to moderate in severity, including increased anxiety, cardiovascular effects such as increased blood pressure and heart rate, hyperthermia, hyperhidrosis, jaw tightness and bruxism, muscle tightness, unpleasant stimulation, reduced appetite, nausea, poor concentration, and impaired balance (see, e.g., Harris et al., Psychopharmacology (Berl), 162(4):396-405, 2002; Liechti et al., Psychopharmacology (Berl), 154(2):161-8, 2001; Oehen et al., J. Psychopharmacol., 27(1): 40-52, 2013; Mas et al., J. Pharmacol. Exp. Ther., 290(1): 136-45, 1999; Mithoefer et al., J. of Psychopharmacology, 25(4): 439-452, 2010; Rogers et al., Health Technol. Assess, 13(6): iii-iv, ix-xii, 1-315, 2009). MDMA is also expected to be approved only for drug-assisted psychotherapy, where it will be administered during one or more day-long drug-assisted sessions, generally with two trained psychotherapists or clinicians. This paradigm may restrict access to vulnerable and disadvantaged patient populations. Enhancing access to the therapeutic benefits of MDMA may be accomplished by providing compounds with comparable or superior efficacy and relatively diminished side effects, as well as other improvements, such as optimized time course of drug action.

Accordingly, there is a need to provide alternative treatment options.

A. GENERAL DEFINITIONS AND TERMS

As used in this specification and the appended claims, the singular forms "a," "an," and "the" include plural referents unless the context clearly dictates otherwise. Thus, for example, reference to "an active agent" includes reference to a combination of two or more active agents, and reference to "an excipient" includes reference to a combination of two or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

Unless otherwise indicated, all numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, "about" refers to plus or minus five percent (±5%) of the recited unit of measure. The term "substantially," where it is applied to modify a feature or limitation herein, will be read in the context of the invention and in light of the knowledge in the art to provide the appropriate certainty, e.g., by using a standard that is recognized in the art for measuring the meaning of "substantially" as a term of degree, or by ascertaining the scope as would one of skill in the art.

In embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

A comprehensive list of the abbreviations utilized by organic chemists of ordinary skill in the art appears in the first issue of each volume of the Journal of Organic Chemistry; this list is typically presented in a table entitled Standard List of Abbreviations; the current list as of the date of this filing is hereby incorporated by reference as if fully set forth herein.

Unless defined otherwise, all technical and scientific terms have the meaning as commonly understood by one having ordinary skill in the art to which this invention belongs, who as a shorthand may be referred to simply as "one of skill." Further definitions to assist the reader in understanding the embodiments are as follows; however, it will be appreciated that such definitions are not intended to limit the scope of the invention, which shall be properly interpreted and understood by reference to the full specification (as well as any plain meaning known to one of skill) in view of the language used in the appended claims. The terminology used herein is for the purpose of describing particular embodiments only and is not intended to be limiting.

Generally, the nomenclature used and procedures performed herein are those known in fields relating to one or more aspects of the invention, such as biology, pharmacology, neuroscience, organic chemistry, synthetic chemistry, and/or medicinal chemistry, and are those that will be well known and commonly employed in such fields. Standard techniques and procedures will be those generally performed according to conventional methods in the art.

"Alkyl" will be understood to include straight or branched radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably from 1 to 6 carbon atoms, more preferably from 1 to 4 carbon atoms, and most preferably from 1 to 3 carbon atoms. For any alkyl, the alkyl may be optionally substituted at one or more positions by deuterium, halogen, alkyl, alkyl ester, hydroxy, alkoxy, carboxy, formyl, aryl, cycloalkyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, $—OP(O)(OH)_2$, —OC(O)H, $—OSO_2OH$, $—OC(O)NH_2$, and $—SONH_2$.

"Alkanyl" refers to saturated branched, straight-chain, or cyclic alkyl radicals derived by the removal of one hydrogen atom from a single carbon atom of a parent alkane. Typical alkanyl groups include methanyl; ethanyl; propanyls such as propan-1-yl, propan-2-yl (isopropyl), and cyclopropan-1-yl; butanyls such as butan-1-yl, butan-2-yl (sec-butyl), 2-methyl-propan-1-yl (isobutyl), 2-methyl-propan-2-yl (t-butyl), and cyclobutan-1-yl; etc.

“Alkenyl” refers to an unsaturated branched, straight-chain, or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl (allyl), prop-2-en-2-yl, cycloprop-1-en-1-yl, and cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, and cyclobuta-1,3-dien-1-yl; and the like.

“Alkynyl” refers to an unsaturated branched, straight-chain, or cyclic alkyl radical having at least one carbon-carbon triple bond derived by the removal of one hydrogen atom from a single carbon atom of a parent alkyne. Typical alkynyl groups include ethynyl; propynyls such as prop-1-yn-1-yl, and prop-2-yn-1-yl; butynyls such as but-1-yn-1-yl, but-1-yn-3-yl, and but-3-yn-1-yl; and the like.

“Aryl” refers to a monovalent aromatic hydrocarbon radical derived by the removal of one hydrogen atom from a single carbon atom of a parent aromatic ring system. Typical aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. Preferably, an aryl group comprises from 6 to 20 carbon atoms, more preferably, between 6 to 12 carbon atoms.

“Arylalkyl” refers to a radical having an alkyl component and an aryl component, where the alkyl component links the aryl component to the point of attachment. The alkyl component is as defined above, except that the alkyl component is at least divalent, an alkylene, to link to the heteroaryl component and to the point of attachment. The alkyl component can include any number of carbons, such as C0-6, C1-2, C1-3, C1-4, C1-5, C1-6, C2-3, C2-4, C2-5, C2-6, C3-4, C3-5, C3-6, C4-5, C4-6 and C5-6. In some instances, the alkyl component can be absent. The aryl component is as defined within. Arylalkyl groups can be substituted or unsubstituted.

“Cycloalkyl” refers to a saturated or partially unsaturated, monocyclic, bicyclic, fused bicyclic or bridged polycyclic ring assembly containing from 3 to 12 ring atoms, or the number of atoms indicated. Cycloalkyl can include any number of carbons, such as 3 to 6 carbon atoms, 4 to 6 carbon atoms, 5 to 6 carbon atoms, 3 to 8 carbon atoms, 4 to 8 carbon atoms, 5 to 8 carbon atoms, 6 to 8 carbon atoms, 7 to 8 carbon atoms, 3 to 9 carbon atoms, 4 to 9 carbon atoms, 5 to 9 carbon atoms, 6 to 9 carbon atoms, 7 to 9 carbon atoms, 8 to 9 carbon atoms, 3 to 10 carbon atoms, 4 to 10 carbon atoms, 5 to 10 carbon atoms, 6 to 10 carbon atoms, 7 to 10 carbon atoms, 8 to 10 carbon atoms, 9 to 10 carbon atoms, 3 to 11 carbon atoms, 4 to 11 carbon atoms, 5 to 11 carbon atoms, 6 to 11 carbon atoms, 7 to 11 carbon atoms, 8 to 11 carbon atoms, 9 to 11 carbon atoms, 10 to 11 carbon atoms, 3 to 12 carbon atoms, 4 to 12 carbon atoms, 5 to 12 carbon atoms, 6 to 12 carbon atoms, 7 to 12 carbon atoms, 8 to 12 carbon atoms, 9 to 12 carbon atoms, 10 to 12 carbon atoms, and 11 to 12 carbon atoms. Saturated monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Saturated bicyclic and polycyclic cycloalkyl rings include, for example, norbornane, bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

“Halogen” refers to fluorine, chlorine, bromine, and iodine.

“Heterocycle” or “heterocyclic” refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Unless stated otherwise specifically in the specification, the heterocyclyl radical is a monocyclic, bicyclic, tricyclic, or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^y-OR^x$, $-R^y-OC(O)-R^x$, $-R^y-OC(O)-OR^x$, $-R^y-OC(O)-N(R^x)_2$, $-R^y-N(R^x)_2$, $-R^y-C(O)R^x$, $-R^y-C(O)OR^x$, $-R^y-C(O)N(R^x)_2$, $-R^y-O-R^z-C(O)N(R^x)_2$, $-R^y-N(R^x)C(O)OR^x$, $-R^y-N(R^x)C(O)R^x$, $-R^y-N(R^x)S(O)tR^x$ (where t is 1 or 2), $-R^y-S(O)tR^x$ (where t is 1 or 2), $-R^y-S(O)tOR^x$ (where t is 1 or 2) and $-R^y-S(O)tN(R^x)_2$ (where t is 1 or 2), where each $R^x$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^y$ is independently a direct bond or a straight or branched alkylene or alkenylene chain, and $R^Z$ is a straight or branched alkylene or alkenylene chain, and where each of the above substituents is unsubstituted unless otherwise indicated.

"Optionally substituted" unless otherwise specified means that a group may be unsubstituted, or substituted by one or more of the substituents listed for that group. Likewise, when a group is described as being "unsubstituted or substituted" if substituted, the substituent(s) may be selected from one or more of the indicated substituents. When there are more than one substituents, the substituents may be the same or different. In one embodiment, an optionally substituted group has one substituent. In another embodiment, an optionally substituted group has two substituents. In another embodiment, an optionally substituted group has three substituents. In another embodiment, an optionally substituted group has four substituents. If no substituents are indicated for an "optionally substituted" or "substituted" group, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, and a tri-substituted amino group.

Still additional definitions and abbreviations are provided elsewhere herein.

B. COMPOUNDS

In one aspect, provided is a compound having the structure of Formula (1):

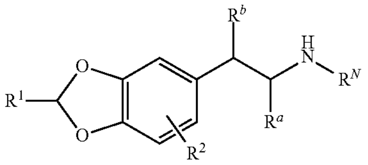

or a pharmaceutically acceptable salt thereof, wherein $R^1$ is H or Y; $R^2$ is H or Y; $R^a$ is X or Y; $R^b$ is H or Y; $R^N$ is methyl or Y; X is H, methyl, or ethyl; and Y is $-(CH_2)_n-CO_2R$, where n is an integer between 0 and 4 inclusive; wherein R is alkyl, cycloalkyl, aryl, arylalkyl, $-(CH_2)_mZ(CH_2)_mCH_3$, or $-(CH_2)_mR^{cyc.}$; wherein Z is independently, and in either orientation, $-O-$, $-C{=}C-$, $-NH-$, $-NHNH-$, $-ONH-$, $-OCNH-$, $-CONH$, $-CH(NH_2)-$, $-OC(O)-$, $-S-$, $-S(O)-$, $-SO_2-$, $-CHF-$, and $-CF_2-$; $R^{cyc}$ is independently an optionally substituted aryl, an optionally substituted heterocycle, or an optionally substituted heteroaryl; and each m is independently between 0 and 4 inclusive; wherein only one of $R^1$, $R^2$, $R^a$, $R^b$, $R^N$, or X is Y.

In some embodiments, $R^1$ is H or Y. In some embodiments, $R^1$ is H. In some embodiments, $R^1$ is Y.

In some embodiments, $R^2$ is H or Y. In some embodiments, $R^2$ is H. In some embodiments, $R^2$ is Y.

In some embodiments, $R^a$ is X or Y. In some embodiments, $R^a$ is X. In some embodiments, $R^a$ is Y.

In some embodiments, $R^b$ is H or Y. In some embodiments, $R^b$ is H. In some embodiments, $R^b$ is Y.

In some embodiments, $R^N$ is methyl or Y. In some embodiments, $R^N$ is methyl. In some embodiments, $R^N$ is Y.

In some embodiments, X is H, methyl, or ethyl. In some embodiments, X is H. In some embodiments, X methyl. In some embodiments, X is ethyl.

In some embodiments, Y is $-(CH_2)_n-CO_2R$, where n is an integer between 0 and 4 inclusive; wherein R is hydrogen, alkyl, cycloalkyl, aryl, arylalkyl, $-(CH_2)_mZ(CH_2)_mCH_3$, or $-(CH_2)_mR^{cyc.}$; wherein Z is independently, and in either orientation, selected from the group consisting of $-O-$, $-C{=}C-$, $-NH-$, $-NHNH-$, $-ONH-$, $-OCNH-$, $-CONH$, $-CH(NH_2)-$, $-OC(O)-$, $-S-$, $-S(O)-$, $-SO_2-$, $-CHF-$, and $-CF_2-$; $R^{cyc}$ is independently an optionally substituted aryl, an optionally substituted heterocycle, or an optionally substituted heteroaryl; and each m is independently between 0 and 4 inclusive. In some embodiments, R is hydrogen. In other embodiments, R is not hydrogen. In some such embodiments, R is alkyl, cycloalkyl, aryl, arylalkyl, $—(CH_2)_mZ(CH_2)_mCH_3$, or $—(CH_2)_mR^{cyc}$; wherein Z is independently, and in either orientation, —O—, —C═C—, —NH—, —NHNH—, —ONH—, —OCNH—, —CONH, $—CH(NH_2)—$, —OC(O)—, —S—, —S(O)—, $—SO_2—$, —CHF—, and $—CF_2—$; $R^{cyc}$ is independently an n optionally substituted aryl, an optionally substituted heterocycle, or an optionally substituted heteroaryl; and each m is independently between 0 and 4 inclusive. In some embodiments, R is alkyl. In some embodiments, R is cycloalkyl. In some embodiments, R is aryl. In some embodiments, R is arylalkyl. In some embodiments, R is $—(CH_2)_mZ(CH_2)_mCH_3$. Z is selected from the group consisting of —O—, —C═C—, —NH—, —NHNH—, —ONH—, —OCNH—, —CONH—, $—CH(NH_2)—$, —OC(O)—, —S—, —S(O)—, $—SO_2—$, —CHF—, and $—CF_2—$. In some embodiments, Z is —O—. In some embodiments, Z is —C═C—. In some embodiments, Z is —NH—. In some embodiments, Z is —NHNH—. In some embodiments, Z is —ONH—. In some embodiments, Z is —OCNH—. In some embodiments, Z is —CONH—. In some embodiments, Z is $—CH(NH_2)—$. In some embodiments, Z is —OC(O)—. In some embodiments, Z is —S—. In some embodiments, Z is —S(O)—. In some embodiments, Z is $—SO_2—$. In some embodiments, Z is —CHF—. In some embodiments, Z is $—CF_2—$. In some embodiments, R is $(CH_2)_mR^{cyc}$.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with: (a) Halogen; (b) $C_{1-7}$alkyl; (c) Hydroxy; (d) Methoxy; (e) Isopropoxy; (f) Ethoxy; (g) Hydroxymethyl; (h) Hydroxypropyl; (i) Tert-butyl; (j) N-butyl; (k) Sec-butyl; (l) Isobutyl; (m) Acetamide; (n) Carbamoyl; (o) CN; (p) COOH; (q) $NO_2$; (r) $S(O)_2OH$; (s) $S(O)CH_3$; (t) $S(O)_2CH_3$;

(u) a group of the formula $—OR^a$, wherein $R^a$ is a hydrogen atom, or an alkyl group of 1 to 7 carbon atoms;

(v) a group of the formula $—SR^b$, wherein $R^b$ is a hydrogen atom, or an alkyl group of 1 to 7 carbon atoms; and (w) a group of the formula $—COOR^c$, wherein $R^c$ is straight or branched alkyl of 1 to 5 carbon atoms or cycloalkyl of 3 to 6 carbon atoms.

In some embodiments, $R^{cyc}$ is an optionally substituted aryl, heterocycle, or heteroaryl. In embodiments, $R^{cyc}$ is an optionally substituted aryl. In embodiments, $R^{cyc}$ is an optionally substituted heterocycle. In embodiments, $R^{cyc}$ is an optionally substituted heteroaryl.

In some embodiments, n is an integer between 0 and 4 inclusive. In some embodiments, n is 0. In some embodiments, n is 1. In some embodiments, n is 2. In some embodiments, n is 3. In some embodiments, n is 4. In some embodiments, m is independently between 0 and 4 inclusive. In some embodiments, m is 0. In some embodiments, m is 1. In some embodiments, m is 2. In some embodiments, m is 3. In some embodiments, m is 4.

In some embodiments, the compound is not selected from the group consisting of

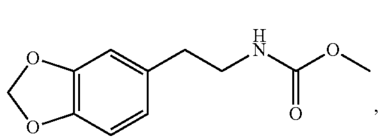
,

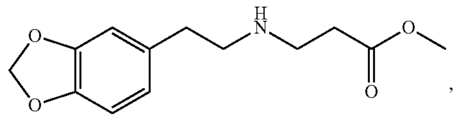
,

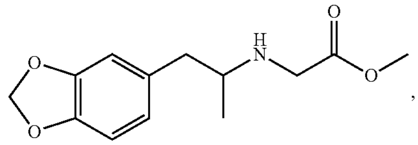
,

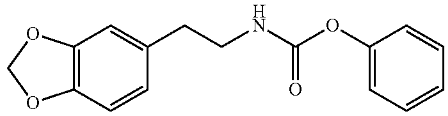
, and

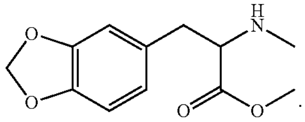
.

In some embodiments, the compound is not

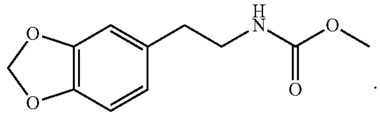 [SMILES: COC(=O)NCCc1ccc2c(c1)OCO2]
.

In some embodiments, the compound is not

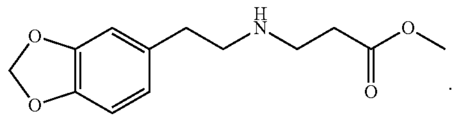 [SMILES: COC(=O)CCNCCc1ccc2c(c1)OCO2]
.

In some embodiments, the compound is not

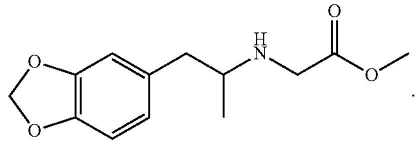 [SMILES: COC(=O)CNC(C)Cc1ccc2c(c1)OCO2]
.

In some embodiments, the compound is not

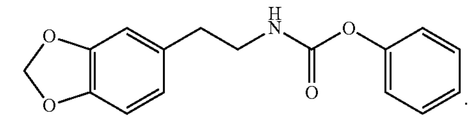 [SMILES: O=C(NCCc1ccc2c(c1)OCO2)Oc1ccccc1]

In some embodiments, the compound is not

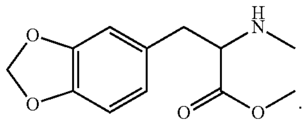 [SMILES: CNC(Cc1ccc2c(c1)OCO2)C(=O)OC]

In some embodiments, the compound is not

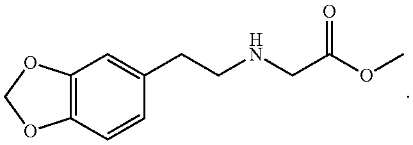 [SMILES: COC(=O)CNCCc1ccc2c(c1)OCO2]

In some embodiments, the compound is not

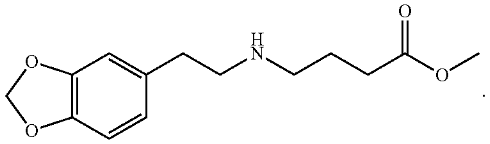 [SMILES: COC(=O)CCCNCCc1ccc2c(c1)OCO2]

In some embodiments, provided herein is a compound, having a structure of Formula (I), wherein X is selected from hydrogen, methyl, and ethyl; Y is —$(CH_2)_n$—$CO_2R$, where n is an integer between 0 and 4 inclusive; R is any of hydrogen (H); alkyl, cycloalkyl, aryl, or arylalkyl, as those terms are defined herein; —$(CH_2)_mZ(CH_2)_mCH_3$ or —$(CH_2)_mR^{cyc}$, where Z and $R^{cyc}$ are as defined herein and where each m is independently an integer between 0 and 4 inclusive; or a pharmaceutically acceptable salt, hydrate, or solvate thereof (which will be understood to include all amorphous and polymorphic forms). Formula (I) is as follows:

(I)

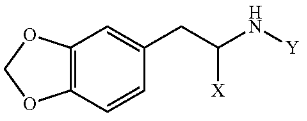

In some embodiments, R is any of hydrogen (H); alkyl, cycloalkyl, aryl, or arylalkyl. In some embodiments, R is hydrogen. In some embodiments, R is not hydrogen. In some embodiments, R is any of alkyl, cycloalkyl, aryl, or arylalkyl.

"Z" is independently, and in either orientation, —O—, —C═C—, —NH—, —NHNH—, —ONH—, —OCNH—, —CONH, —$CH(NH_2)$—, —OC(O)—, —S—, —S(O)—, —$SO_2$—, —CHF—, and —$CF_2$—.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with any of substituents (a) (Halogen) through (w) (a group of the formula —$COOR^c$ as herein defined), as discussed above.

Non-limiting exemplary compounds described herein of Formula (I) are below:

<u>Exemplary Embodiments of Formula I</u>

I-1

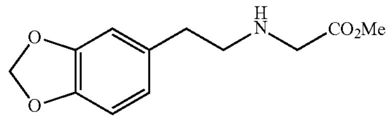

I-2

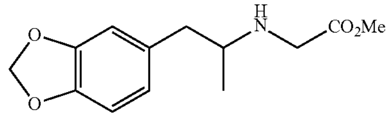

I-3

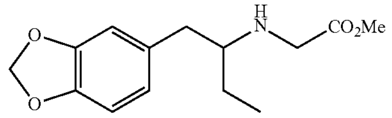

I-4

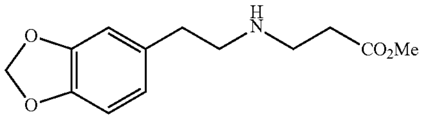

I-5

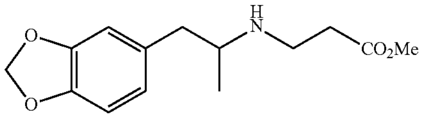

I-6

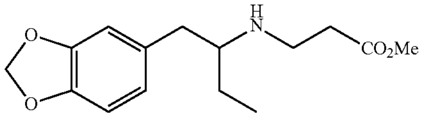

In some embodiments, for instance embodiments consisting of a single compound of Formula (I), or a composition consisting essentially of a single compound of Formula (I), the compound of Formula (I) will be as described above, but wherein when X is H, Y is any substituent besides —$(CH_2)(CO_2H)$, —$(CH_2)(CO_2Me)$, —$(CH_2)_2(CO_2H)$, and —$(CH_2)_2$ $(CO_2Me)$ (i.e., as otherwise described, but wherein when X is H, Y is not $(CH_2)(CO_2H)$, —$(CH_2)(CO_2Me)$, —$(CH_2)_2(CO_2H)$, or —$(CH_2)_2(CO_2Me)$.

In some embodiments, for instance embodiments consisting of a single compound of Formula (I), or a composition consisting essentially of a single compound of Formula (I), the compound of Formula (I) will be as described above, but wherein when X is Me, Y is any substituent besides —$(CH_2)(CO_2H)$, and —$(CH_2)(CO_2Me)$ (i.e., as otherwise described, but wherein when X is Me, Y is not —$(CH_2)(CO_2H)$, or —$(CH_2)(CO_2Me)$.

In some embodiments, the compound is not

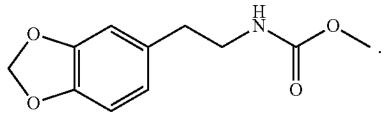 [SMILES: COC(=O)NCCc1ccc2c(c1)OCO2]

In some embodiments, the compound is not

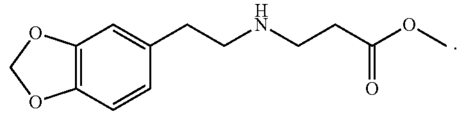 [SMILES: COC(=O)CCNCCc1ccc2c(c1)OCO2]

In some embodiments, the compound is not

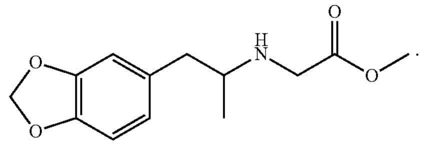 [SMILES: COC(=O)CNC(C)Cc1ccc2c(c1)OCO2]

In some embodiments, the compound is not

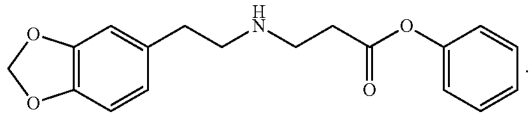 [SMILES: O=C(CCNCCc1ccc2c(c1)OCO2)Oc1ccccc1]

In some embodiments, the compound is not

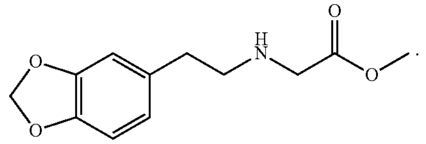 [SMILES: COC(=O)CNCCc1ccc2c(c1)OCO2]

In some embodiments, the compound is not

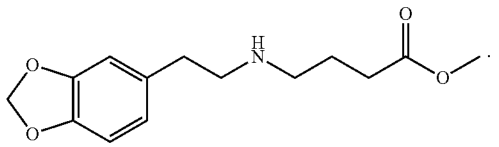 [SMILES: COC(=O)CCCNCCc1ccc2c(c1)OCO2]

In some embodiments, provided herein is a compound, having a structure of Formula (II), wherein X is selected from hydrogen, methyl, and ethyl; Y is —$(CH_2)_n$—$CO_2R$, where n is an integer between 0 and 4 inclusive; R is any of hydrogen (H); alkyl, cycloalkyl, aryl, or arylalkyl, as those terms are defined herein; —$(CH_2)_mZ(CH_2)_mCH_3$ or —$(CH_2)_m$ $R^{cyc}$, where Z and $R^{cyc}$ are as defined herein and where each m is independently an integer between 0 and 4 inclusive; or a pharmaceutically acceptable salt, hydrate, or solvate thereof (which will be understood to include all amorphous and polymorphic forms). Formula (II) is as follows:

(II)

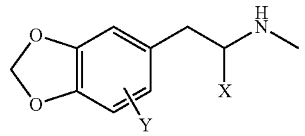

In some embodiments, R is any of hydrogen (H); alkyl, cycloalkyl, aryl, or arylalkyl. In some embodiments, R is hydrogen. In some embodiments, R is not hydrogen. In some embodiments, R is any of alkyl, cycloalkyl, aryl, or arylalkyl.

In one aspect, the compound of Formula (II) is a compound of Formula (IIA), or a pharmaceutically acceptable salt, hydrate, or solvate thereof (which will be understood to include all amorphous and polymorphic forms). Formula (IIA) is as follows:

(IIA)

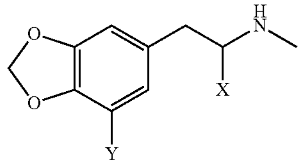

In one aspect, the compound of Formula (II) is a compound of Formula (IIB), or a pharmaceutically acceptable salt, hydrate, or solvate thereof (which will be understood to include all amorphous and polymorphic forms). Formula (IIB) is as follows:

(IIB)

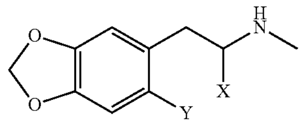

In some embodiments, for instance embodiments consisting of a single compound of Formula (IIB), or a composition consisting essentially of a single compound of Formula (IIB), the compound of Formula (IIB) will be as described above, but wherein when X is H, Y is any substituent besides —$(CH_2)_2(CO_2H)$ (i.e., as otherwise described, but wherein when X is H, Y is not —$(CH_2)_2(CO_2H)$.

In one aspect, the compound of Formula (II) is a compound of Formula (IIC), or a pharmaceutically acceptable salt, hydrate, or solvate thereof (which will be understood to include all amorphous and polymorphic forms). Formula (IIC) is as follows:

(IIC)

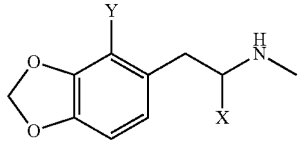

"Z" is independently, and in either orientation, —O—, —C═C—, —NH—, —NHNH—, —ONH—, —OCNH—, —CONH, —$CH(NH_2)$—, —OC(O)—, —S—, —S(O)—, —$SO_2$—, —CHF—, and —$CF_2$—.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with any of substituents (a) (Halogen) through (w) (a group of the formula —$COOR^c$ as herein defined), as discussed above.

Non-limiting exemplary compounds described herein of Formula (II) are below:

Formula (IIA)

IIA-1

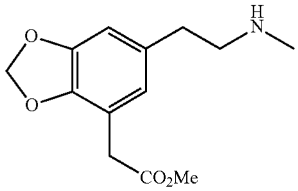

IIA-2

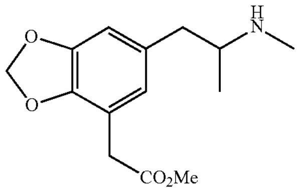

IIA-3

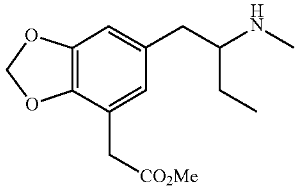

-continued

IIA-4

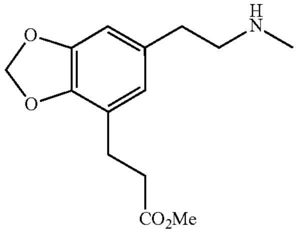

IIA-5

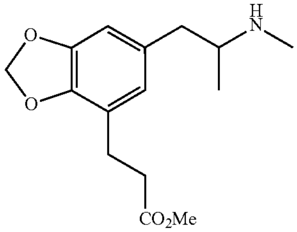

IIA-6

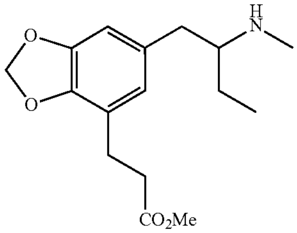

Formula (IIB)

IIB-1

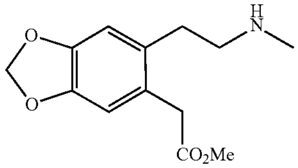

IIB-2

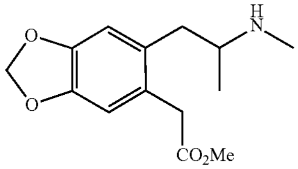

IIB-3

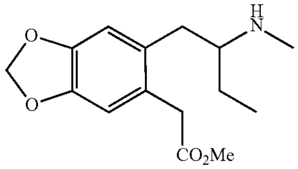

IIB-4

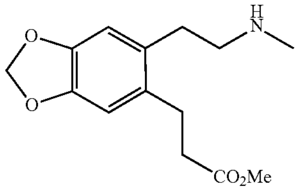

-continued

IIB-5

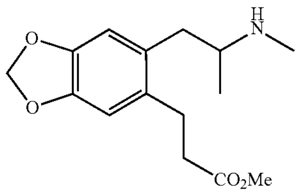

IIB-6

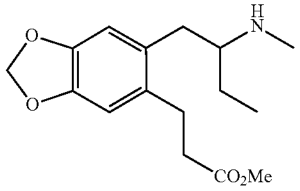

Formula (IIC)

IIC-1

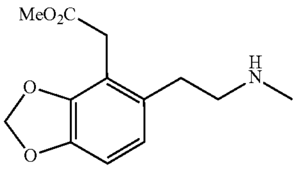

IIC-2

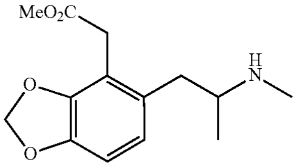

IIC-3

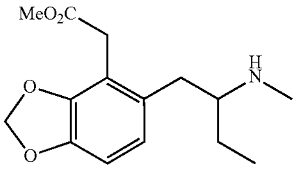

IIC-4

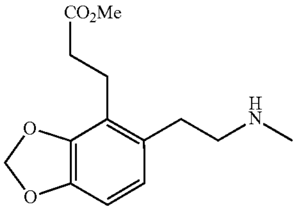

IIC-5

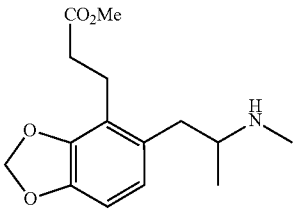

-continued

IIC-6

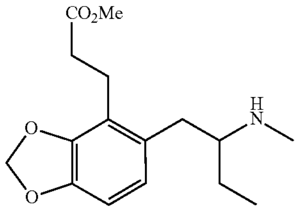

In some embodiments, provided herein is a compound, having a structure of Formula III, wherein Y is $—(CH_2)_n—CO_2R$, where n is an integer between 0 and 4 inclusive; R is any of hydrogen (H); alkyl, cycloalkyl, aryl, or arylalkyl, as those terms are defined herein; $—(CH_2)_mZ(CH_2)_mCH_3$ or $—(CH_2)_mR^{cyc}$, where Z and $R^{cyc}$ are as defined herein and where each m is independently an integer between 0 and 4 inclusive; or a pharmaceutically acceptable salt, hydrate, or solvate thereof (understood to include all amorphous and polymorphic forms). Formula (III) is as follows, and like all such other Formulae, referred by reference to its numeral as follows:

(III)

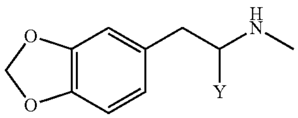

In some embodiments, R is any of hydrogen (H); alkyl, cycloalkyl, aryl, or arylalkyl. In some embodiments, R is hydrogen. In some embodiments, R is not hydrogen. In some embodiments, R is any of alkyl, cycloalkyl, aryl, or arylalkyl.

"Z" is independently, and in either orientation, —O—, —C═C—, —NH—, —NHNH—, —ONH—, —OCNH—, —CONH, $—CH(NH_2)—$, —OC(O)—, —S—, —S(O)—, $—SO_2—$, —CHF—, and $—CF_2—$.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with any of substituents (a) (Halogen) through (w) (a group of the formula $—COOR^c$ as herein defined), as discussed above.

Non-limiting exemplary compounds described herein of Formula (III) are below:

Exemplary Embodiments of Formula (III)

III-1

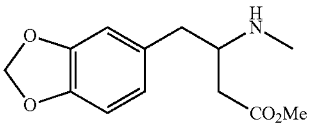

III-2

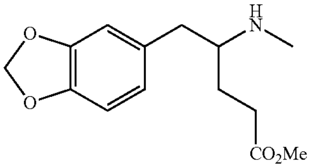

In some embodiments, the compound is not

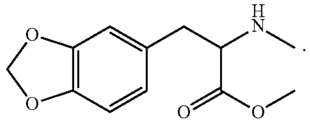 [SMILES: CNC(Cc1ccc2c(c1)OCO2)C(=O)OC]

In some embodiments, provided herein is a compound, having a structure of Formula (IV), wherein X is selected from hydrogen, methyl, and ethyl; Y is $—(CH_2)_n—CO_2R$, where n is an integer between 0 and 4 inclusive; R is any of hydrogen (H); alkyl, cycloalkyl, aryl, or arylalkyl, as those terms are defined herein; $—(CH_2)_mZ(CH_2)_mCH_3$ or $—(CH_2)_mR^{cyc}$, where Z and $R^{cyc}$ are as defined herein and where each m is independently an integer between 0 and 4 inclusive; or a pharmaceutically acceptable salt, hydrate, or solvate thereof (which will be understood to include all amorphous and polymorphic forms).

(IV)

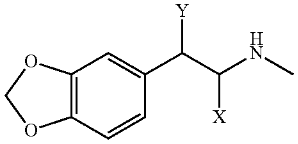

In some embodiments, R is any of hydrogen (H); alkyl, cycloalkyl, aryl, or arylalkyl. In some embodiments, R is hydrogen. In some embodiments, R is not hydrogen. In some embodiments, R is any of alkyl, cycloalkyl, aryl, or arylalkyl.

"Z" is independently, and in either orientation, —O—, —C═C—, —NH—, —NHNH—, —ONH—, —OCNH—, —CONH, $—CH(NH_2)—$, —OC(O)—, —S—, —S(O)—, $—SO_2—$, —CHF—, and $—CF_2—$.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with any of substituents (a) (Halogen) through (w) (a group of the formula $—COOR^c$ as herein defined), as discussed above.

Non-limiting exemplary compounds described herein of Formula (IV) are below:

Exemplary Embodiments of Formula (IV)

IV-1

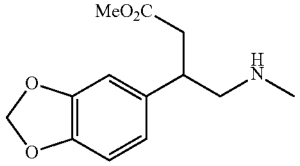

IV-2

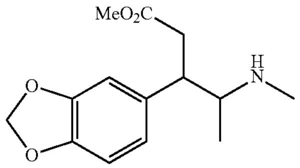

IV-3

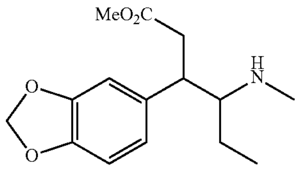

IV-4

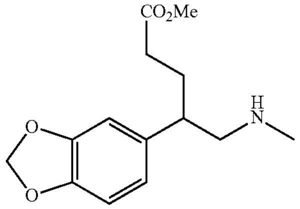

IV-5

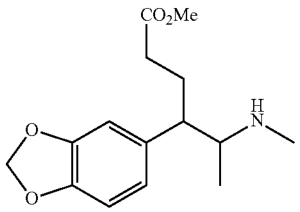

IV-6

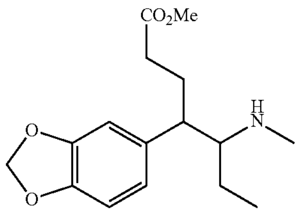

In some embodiments, provided herein is a compound, having a structure of Formula V, wherein X is selected from hydrogen, methyl, and ethyl; Y is $—(CH_2)_n—CO_2R$, where n is an integer between 0 and 4 inclusive; R is any of hydrogen (H); alkyl, cycloalkyl, aryl, or arylalkyl, as those terms are defined herein; $—(CH_2)_mZ(CH_2)_mCH_3$ or $—(CH_2)_mR^{cyc}$, where Z and $R^{cyc}$ are as defined herein and where each m is independently an integer between 0 and 4 inclusive; or a pharmaceutically acceptable salt, hydrate, or solvate thereof (which will be understood to include all amorphous and polymorphic forms).

(V)

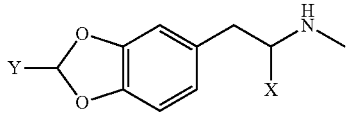

In some embodiments, R is any of hydrogen (H); alkyl, cycloalkyl, aryl, or arylalkyl. In some embodiments, R is hydrogen. In some embodiments, R is not hydrogen. In some embodiments, R is any of alkyl, cycloalkyl, aryl, or arylalkyl.

"Z" is independently, and in either orientation, —O—, —C═C—, —NH—, —NHNH—, —ONH—, —OCNH—, —CONH, $—CH(NH_2)—$, —OC(O)—, —S—, —S(O)—, $—SO_2—$, —CHF—, and $—CF_2—$.

"$R^{cyc}$" is independently an aryl, heterocycle, or heteroaryl, said aryl, heterocycle, or heteroaryl as defined herein or as selected from the class consisting of phenyl, naphthyl, naphthalenyl, indolyl, thiophenyl, pyridyl, pyridinyl, pyrimidinyl, furyl, furanyl, tetrahydrofuranyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzofuranyl, dihydrobenzofuranyl, benzoyl, benzoxazolyl, methylenedioxyphenyl, isobenzofuranyl, benzothiophenyl, benzoxazolyl, indazolyl, benzthiazolyl, benzimidazolyl, quinolinyl, isoquinolinyl, purinyl, quinolizinyl, cinnolinyl, phthalyl, quinoxalinyl, napthyridinyl, pteridinyl, quinazolinyl, and wherein one or more hydrogen atoms of said aryl, heterocycle, or heteroaryl are optionally and independently replaced with any of substituents (a) (Halogen) through (w) (a group of the formula $—COOR^c$ as herein defined), as discussed above.

The compounds described herein may contain one or more asymmetric centers and give rise to enantiomers, diastereomers, and other stereoisomeric forms. Each chiral center may be defined, in terms of absolute stereochemistry, as (R)- or (S)-. The invention includes all such possible isomers, as well as mixtures thereof, including racemic and optically pure forms.

Optically active (R)- and (S)-, (−)- and (+)-, or (D)- and (L)-isomers may be prepared using chiral synthons or chiral reagents, or resolved using conventional techniques. Various methods are known in the art for preparing optically active forms and determining activity.

In some embodiments are disclosed pharmaceutical compositions in which the compound is present as a pure or substantially pure individual enantiomer, or an enantiomerically enriched mixture having an optical purity of between 0-25%, between 25-50%, between 50-75%, between 75-90%, between 90-95%, or at least 95% enantiomeric excess.

When the compounds described herein contain olefinic double bonds or other centers of geometric asymmetry, and unless specified otherwise, it is intended that the compounds include both E and Z geometric isomers. Likewise, tautomeric forms are included.

The invention also includes compounds with at least one desired isotopic substitution of an atom, at an amount above the natural abundance of the isotope, i.e., isotopically enriched. Isotopes are atoms having the same atomic number but different mass numbers, i.e., the same number of protons but a different number of neutrons. Examples of isotopes that can be incorporated into compounds described herein include isotopes of hydrogen, carbon, nitrogen, oxygen, and chlorine such as $^{2}H$, $^{3}H$, $^{11}C$, $^{13}C$, $^{14}C$, $^{15}N$, $^{17}O$, $^{18}O$, and $^{36}Cl$ respectively. In one non-limiting embodiment, isotopically labeled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and pro-soft drugs thereof can generally be prepared by carrying out the procedures disclosed in the schemes or in the examples and preparations described below by substituting a readily available isotopically labeled reagent for a non-isotopically labeled reagent.

By way of example and without limitation, isotopes of hydrogen including deuterium ($^{2}H$) and tritium ($^{3}H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is at least 60, 70, 80, 90, 95, or 99% or more enriched in an isotope at any location of interest. In one non-limiting embodiment, deuterium is 90, 95, or 99% enriched at a desired location.

The term "isotopically-labeled" analog refers to an analog that is a "deuterated analog," a "$^{13}C$-labeled analog" or a "deuterated/$^{13}C$-labeled analog." "Deuterated analog" means a compound described herein, whereby a H-isotope, i.e., hydrogen/protium ($^{1}H$), is substituted by a H-isotope, i.e., deuterium ($^{2}H$). Deuterium substitution can be partial or complete. Partial deuterium substitution means that at least one hydrogen is substituted by at least one deuterium. In certain embodiments, the isotope is at least 60, 70, 80, 90, 95, or 99% or more enriched in an isotope at any location of interest. In some embodiments it is deuterium that is 90, 95, or 99% enriched at a desired location. Unless indicated to the contrary, the deuteration is at least 80% at the selected location. Deuteration can occur at any replaceable hydrogen that provides the desired results.

The individual compounds of the compositions of the invention will be understood to also encompass pharmaceutically acceptable salts of such compounds. The term "pharmaceutically acceptable salt" refers to salts prepared from pharmaceutically acceptable non-toxic acids or bases, which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, salts of the compounds are those wherein the counter-ion is pharmaceutically acceptable. Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. (See Berge et al. (1977) "Pharmaceutical Salts," J. Pharm. Sci. 66:1-19.)

In some embodiments, preferred pharmaceutically acceptable salts will be those employing a hydrochloride anion. For example, in some such embodiments, the compound is any one of:

I-2 HCl

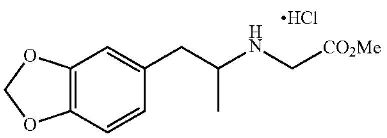

I-5 HCl

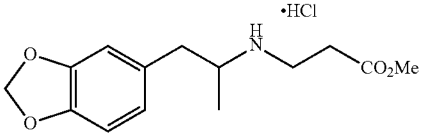

IIA-2 HCl

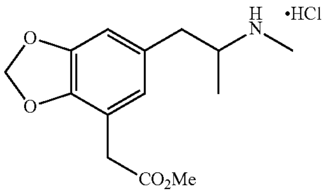

-continued

IIA-5 HCl

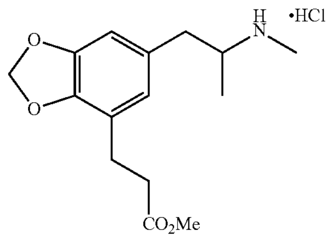

In some embodiments, the compound is not I-2 HCl. In some embodiments, the compound is any one of (I-5 HCl)

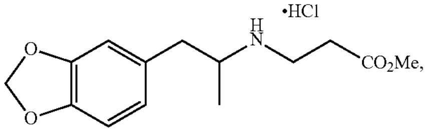

(IIA-2 HCl)

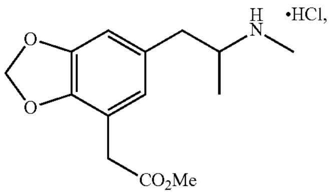

or (IIA-5 HCl)

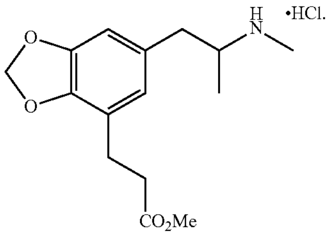

In some embodiments, disclosed esters are "soft drugs." Soft drugs exert therapeutic effects, for example, by interacting with a target receptor or site of action, prior to rapid metabolic conversion into a biologically inactive metabolite. In addition to considering efficacy, an aim of soft drug design is to leverage moieties that will yield inactive and/or non-toxic compounds after metabolism (Buchwald & Bodor, Pharmazie. 2014 June; 69(6):403-13). Quick metabolism of soft drugs yields various effects, including minimizing duration of action, eliminating exposure to toxic metabolites, and reducing any possible drug-drug interactions. For example, various esters of ketamine have exhibited diverse effects on potency, duration of action, and psychomimetic effects of the drug (Jose et al., Bioorganic & medicinal chemistry. 2013 Sep. 1; 21(17):5098-106; Harvey et al., Anesthesia & Analgesia. 2015 October; 121(4):925-33; Dimitrov et al., Bioorganic & med chemistry. 2019 Apr. 1; 27(7):1226-31). Provided that CYP450 enzymes, the major metabolizers, are subject to saturation and inhibition, fast metabolism may be facilitated by directing metabolism to hydrolytic enzymes, for example, by incorporating a metabolically sensitive "soft spot," such as an ester (Buchwald, Expert Opin Drug Metab Toxicol. 2020 August; 16(8):645-650).

Several strategies exist for preparing soft drugs. Some major approaches described herein pertain to soft analogs, active metabolite-based soft drugs, inactive metabolite-based soft drugs, controlled release endogenous agents or natural soft drugs, and activated soft compounds. Soft analogs are close structural analogs of a known or lead compound wherein metabolically sensitive moieties have been introduced to modify inactivation and/or excretion properties. The active metabolite approach leverages the biotransformation of a compound. Selecting an active species of biotransformation that exerts a desired pharmacological effect and undergoes a conversion into an inactive metabolite is one example of this approach. In contrast, the inactive metabolite approach relies on chemically modifying an inactive form of a compound to produce a pharmacologically active compound. A metabolic conversion would then restore the initial inactive compound and eliminate exposure to any toxic intermediates. Endogenous biologically active agents that are efficiently metabolized can be described as natural soft drugs. A pro-soft drug approach can be adopted to modify the metabolism and duration of action of such compounds, for example, when metabolism of a desired compound is so rapid that it interferes with or precludes a desired pharmacological effect. Activated soft compounds result from incorporating a moiety with known pharmacological activity into a non-toxic compound. After exerting therapeutic activity, activated soft compounds are metabolized into their original non-toxic state (Bhardwaj et al., Saudi Pharm. J., 22(4):290-302, 2014).

Esterases, hydrolases that split ester bonds, are ubiquitously distributed throughout the body, and can facilitate metabolism in the plasma, gut, liver, and other tissues (Williams, Man. Clin Pharmacokinet 10, 392-403, 1985). Hydrolytic degradation can inactivate an ester, for example, by introducing a change in charge and/or shape that diminishes the metabolite's binding affinity for the original target (Buchwald, Expert Opin Drug Metab Toxicol. 2020 August; 16(8):645-650). However, like CYP enzymes, genetic polymorphisms of esterases exist, and the enzymes are subject to induction, inhibition, and altered activity resulting from liver disease (Laizure et al. Pharmacotherapy. 2013 February; 33(2):210-22). Additionally, the activity of esterases can be unpredictable. The activity of such enzymes varies across tissues and between individuals, and is influenced by a variety of factors, including age (Di, 2019).

In some embodiments, the compounds provided herein are quickly metabolized. In some embodiments, aspects of the metabolism of the compounds provided herein, such as the rate of metabolism, can be modified by adjusting the size and bulk of the R group in an ester ($—CO_2R$). In some embodiments, the compounds provided herein are rapidly inactivated and/or eliminated, such as in and from the body of a subject. In some embodiments, rapid inactivation and/or elimination of the compounds provided herein facilitates a short duration of action. In some embodiments, hydrolysis of esters of the compounds provided herein facilitates a predictable duration of action. In some embodiments, hydrolysis of esters of the compounds provided herein facilitates a short duration of action. In some embodiments, the compounds provided herein exhibit a reduced duration of action relative to MDMA.

Pro-soft drugs, which require metabolic transformation for conversion into an active soft drug, have been described (Mukker et al., J Pharm Sci. 2016 September; 105(9):2509-2514). Prodrugs are differentiated from soft drugs in that they must undergo metabolic conversion to become biologically active, whereas metabolism of soft drugs, which are delivered as active agents, promotes inactivation and excretion. Incorporation of an ester moiety is an approach in preparing prodrugs (Rautio et al., Nat Rev Drug Discov. 2008; 7, 255-270). Examples of prodrugs using ester or phosphoramidate as biologically labile or cleavable (protecting) groups are disclosed in U.S. Pat. Nos. 6,875,751, 7,585,851, and 7,964,580.

MDMA and its metabolites can pose safety risks associated with toxicity. Side effects range in severity and include but are not limited to elevation in heart rate and blood pressure, hyperthermia, and hepatic toxicity (Kalant, CMAJ: Journal de l'Association médicale canadienne, 2001; 165(7), 917-928). Major metabolites of MDMA include 3,4-methylenedioxyamphetamine (MDA), 4-hydroxy-3-methoxy-methamphetamine (HMMA) and 4-hydroxy-3-methoxy-amphetamine (HMA). MDMA is mainly metabolized in the liver, where several different enzymes play a role in its metabolism, including CYP2D6 (Tucker, Biochem pharmacol., 47(7), pp. 1151-1156, 1994; de la Torre et al., Frontiers in genetics, 2012; 3, 235). However, such enzymes may be saturated at relatively low levels of the drug. Non-linearity in MDMA pharmacokinetics has been identified, and a small increase in dose of the drug has been shown to translate into a disproportionately high increase in plasma concentration (de la Torre et al., British journal of clinical pharmacology, 2000; 49(2), 104-109). Additionally, some MDMA metabolites, such as MDA, retain pharmacological activity and extend the duration of action, which can increase the likelihood of toxicity. The catechol moieties of MDMA and certain metabolites thereof, such as MDA, are postulated to be inherently reactive. Downstream effects of such reactivity include generation of reactive oxygen species, reactive nitrogen species, and other toxic byproducts (Carvalho et al., Curr Pharm Biotechnol. 2010 August; 11(5):476-95).

In embodiments, the compounds provided herein are not converted, such as metabolized, into pharmacologically active metabolites. In embodiments, the compounds provided herein are not converted, such as metabolized, into toxic metabolites, such as metabolites associated with side effects. In embodiments, the compounds provided herein are not converted, such as metabolized, into MDA. In embodiments, the compounds provided herein are not associated with side effects, such as following administration to a subject. In embodiments, the compounds provided herein do not cause side effects, such as following administration to a subject.

In the case of solid compositions, it is understood that the compounds used in the methods of the invention may exist in different forms. For example, the compounds may exist in stable and metastable crystalline forms, isotropic and amorphous forms, milled forms and nano-particulate forms, all of which are intended to be within the scope of the present invention. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravimetric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

The compounds described herein now generally described will be more readily understood by reference to the following description and examples, which are included for the purposes of illustration of certain aspects of the embodiments of the invention. The following is not intended to limit the invention, as one of skill in the art would recognize from the teachings and examples herein that other techniques and methods can satisfy the claims and be employed without departing from the scope of the invention. Indeed, while this invention has been particularly shown and described with reference to certain exemplary embodiments, it will be understood by those skilled in the art that various changes in form and details may be made without departing from the scope or spirit of the invention encompassed by the appended claims.

C. PHARMACEUTICAL COMPOSITIONS AND METHODS OF ADMINISTRATION

Provided are compositions, such as pharmaceutical compositions and formulations, and methods of administering the same. As referred to herein, "compositions" and "formulations" may be used interchangeably. In some embodiments, the individual compounds described herein are administered as part of a pharmaceutical composition or formulation, e.g., as the drug substance or active pharmaceutical ingredient ("API"). "Pharmaceutical compositions" are compositions comprising disclosed compound(s) together in an amount (for example, in a unit dosage form) with a pharmaceutically acceptable carrier, diluent, or excipient. It should be understood that some embodiments do not have a single carrier, diluent, or excipient alone, but include multiple carriers, diluents, and/or excipients. Compositions can be prepared by standard pharmaceutical formulation techniques such as disclosed in Remington: The Science and Practice of Pharmacy (2005) 21th ed., Mack Publishing Co., Easton, Pa.; The Merck Index (1996) 12th ed., Merck Publishing Group, Whitehouse, N.J.; Pharm. Principles of Solid Dosage Forms (1993), Technomic Publishing Co., Inc., Lancaster, Pa.; and Ansel and Stoklosa, Pharm. Calculations (2001) 11th ed., Lippincott Williams & Wilkins, Baltimore, Md.; and Poznansky et al. Drug Delivery Systems (1980), R. L. Juliano, ed., Oxford, N.Y., pp. 253-315).

"Pharmaceutically acceptable" as used in connection with one or more ingredients means that the ingredients are generally safe and, within the scope of sound medical judgment, suitable for use in contact with the cells of humans and other animals without undue toxicity, irritation, allergic response, or complication, and commensurate with a reasonable risk/benefit ratio.

In some embodiments, pure or substantially pure individual compounds described herein are administered as part of a pharmaceutical composition or formulation. The terms "pure" or "substantially pure" as used herein, refer to material that is substantially or essentially free from components that normally accompany the material when the material is synthesized, manufactured, or otherwise produced. A "pure" or "substantially pure" preparation of a compound is accordingly defined as a preparation having a chromatographic purity (of the desired compound) of greater than 90%, more preferably greater than 95%, more preferably greater than 96%, more preferably greater than 97%, more preferably greater than 98%, more preferably greater than 99%, more preferably greater than 99.5%, and most preferably greater than 99.9%, as determined by area normalization of an HPLC profile or other similar detection method. Preferably the pure or substantially pure compound used in the invention is substantially free of any other active compounds which are not intended to be administered to a subject. In this context "substantially free" can be taken to mean that no active compound(s) other than the active compound intended to be administered to a subject are detectable by HPLC or other similar detection method, or are below a desired threshold of detection such as defined above.

a. Compositions, Dosage Forms, and Methods for Preparing the Same

In some embodiments, a compound described herein can be formulated into any suitable dosage form, including aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed-release formulations, immediate-release formulations, modified release formulations, extended-release formulations, pulsatile release formulations, multi particulate formulations, and mixed immediate release and controlled release formulations. Generally speaking, one will desire to administer an amount of the active agent of the invention that is effective to achieve a plasma level commensurate with the concentrations found to be effective in vivo for a period of time effective to elicit the desired therapeutic effect(s).

In some embodiments, compositions comprising a compound provided herein are formulated in a unit dosage form. The term "unit dosage form" refers to a physically discrete unit suited as unitary dosages for the subject to be treated, each unit containing a predetermined quantity of active material calculated to produce the desired therapeutic effect (s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose), of the pharmaceutical composition administered. Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis of a subject for an extended or brief period of time.

In embodiments, compositions comprising a compound provided herein are formulated in a pharmaceutically acceptable oral dosage form, including oral solid dosage forms and oral liquid dosage forms. In embodiments, the compositions are formulated as a pharmaceutically acceptable oral solid dosage form. Oral solid dosage forms may include but are not limited to, lozenges, troches, tablets, capsules, caplets, powders, pellets, multiparticulates, beads, spheres, and/or any combinations thereof. Oral solid dosage forms may be formulated as immediate release, controlled release, sustained release, extended release, or modified release formulations.

In some embodiments, the solid dosage provided herein, such as oral solid dosage forms, may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived IPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. In embodiments, pharmaceutical formulations described herein may be administered as a single capsule or in multiple capsule dosage form. In embodiments, the pharmaceutical formulation is administered in two, three, four, or more capsules or tablets.

In some embodiments, solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. In some embodiments, solid dosage forms also can comprise one or more pharmaceutically acceptable additives such as a compatible carrier, complexing agent, ionic dispersion modulator, disintegrating agent, surfactant, lubricant, colorant, moistening agent, plasticizer, stabilizer, wetting agent, anti-foaming agent, alone or in combination, as well as supplementary active agent(s). In some embodiments, supplementary active agents include preservatives, antioxidants, antimicrobial agents including biocides and biostats such as antibacterial, antiviral and antifungal agents.

In some aspects, provided herein are methods for preparing a composition, such as a pharmaceutical composition comprising a compound described herein. In some embodiments, a pharmaceutical composition, as provided herein, comprises one or more excipients, such as a pharmaceutically acceptable excipient. Non-limiting examples of excipients include fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof.

In some embodiments, the pharmaceutical composition may be an immediate release formulation, wherein a therapeutically effective amount of the pharmaceutical composition is administered to the subject in a way that facilitates rapid release. Immediate-release formulations may be prepared by combining a superdisintegrant such as croscarmellose sodium and different grades of microcrystalline cellulose in different ratios. In some embodiments, to aid disintegration, sodium starch glycolate may be added.

In some embodiments, tablets provided herein are prepared by methods well known in the art. Various methods for the preparation of the immediate release, modified release, controlled release, and extended-release dosage forms (e.g., as matrix tablets having one or more modified, controlled, or extended-release layers) and the vehicles therein are well known in the art. In some embodiments, a tablet may be made by compression or molding. In some embodiments, compressed tablets may be prepared by compressing, in a suitable machine, an active ingredient in a free-flowing form such as a powder or granules, optionally mixed with a binder, lubricant, inert diluent, preservative, surface-active or dispersing agent. In some embodiments, molded tablets may be produced by molding, in a suitable apparatus, a mixture of powdered compound moistened with an inert liquid diluent. In some embodiments, the tablets may optionally be coated or scored and may be formulated so as to provide a slow or controlled release of the active ingredient therein. Generally recognized compendia of methods include Remington, The Science and Practice of Pharmacy, 23rd Ed., Academic Press, 2020 and Sheth et al., Compressed tablets in Pharm. Dosage forms, v.1, Lieberman & Lachtman, eds., 1980.

In some embodiments, solid dosage forms are prepared by mixing the active agents of the invention with one or more pharmaceutical excipients to form a "bulk blend" composition. In some embodiments, the bulk blend composition is homogeneous, i.e., the active agents are dispersed evenly throughout so that the bulk blend may be readily subdivided into equally effective unit dosage forms, such as tablets, pills, and capsules. In some embodiments, the individual unit dosages may also comprise film coatings, which disintegrate upon oral ingestion or upon contact with diluents. In some embodiments, these formulations are manufactured by conventional pharmaceutical techniques. Conventional pharmaceutical techniques for preparation of solid dosage forms include, but are not limited to, the following methods, which may be used alone or in combination: (1) dry mixing, (2) direct compression, (3) milling, (4) dry or non-aqueous granulation, (5) wet granulation, or (6) fusion (see, e.g., Lachman et al., Theory and Practice of Industrial Pharmacy, 1986). Other methods include spray drying, pan coating, melt granulation, granulation, fluidized bed spray drying or coating (e.g., Wurster coating), tangential coating, top spraying, tableting, and extruding.

In some embodiments, a composition comprising a compound as provided herein can be formulated to achieve a specific release profile. In some embodiments, oral solid dosage forms may be prepared as immediate release formulations, or as modified release formulations, such as controlled release, extended release, sustained release, or delayed release.

In some embodiments of modified release formulations, the plasma half-life compared to the plasma half-life of an immediate release formulation is greater by at least 5%, at least 10%, at least 15%, at least 20%, at least 25%, at least 30%, at least 35%, at least 50%, at least 75%, at least 100%, or values in between. In some embodiments of modified release formulations, the formulations are designed to result in a comparable area under the curve, or $AUC_{0-24}$, and a similar safety and efficacy profile, but having a delayed time to maximum concentration ($t_{max}$) of at least 5%, at least 10%, at least 15%, at least 20%, at least 25%, at least 30%, at least 35%, at least 50%, at least 75%, at least 100%, or values in between, as would be appreciated by one of skill. In some preferred embodiments, a formulation is designed to be a product with a specific time course based on an optimum "therapeutic window," such as less than about 30 minutes, about 30 minutes, about 45 minutes, about 60 minutes, about 90 minutes, about 2 hours, about 3 hours, about 4 hours, about 5, about 6, about 7, about 8, and greater than 8 hours, including lengths of time in between.

In some embodiments, oral solid dosage forms are formulated as a delayed release dosage form by utilizing an enteric coating to affect release in the small intestine of the gastrointestinal tract. An enteric-coated oral dosage form may be a compressed or molded or extruded tablet/mold (coated or uncoated) containing granules, powder, pellets, beads or particles of the active ingredient and/or other composition components, which are themselves coated or uncoated. The enteric-coated oral dosage form may also be a capsule (coated or uncoated) containing pellets, beads or granules of the solid carrier or the composition, which are themselves coated or uncoated. In some embodiments, enteric coatings may be used to prepare other controlled release dosage forms, including but not limited to extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

In some embodiments, the controlled release dosage form is a pulsatile release solid oral dosage form comprising at least two groups of particles, each containing active agents of the invention. In some embodiments, the first group of particles, upon ingestion by a subject, provides a substantially immediate dose of the active agents of the invention, and may either be uncoated, or comprise a coating and/or sealant. In some embodiments, using such means, a single unit dosage form can provide both a first and a second dosage amount in the single form (i.e., a first dosage amount in an immediate release form, and a second dosage amount in a delayed release form). In some embodiments, gastroretentive sustained release tablets are formulated by using a combination of hydrophilic polymer (e.g., hydroxypropyl methylcellulose), together with at least one swelling agent (e.g., crospovidone, sodium starch glycolate, and croscarmellose sodium), and an effervescent substance (e.g., sodium bicarbonate). Using known methods, gastroretentive tablets can be formulated to prolong the gastric emptying time and extend the mean residence time (MRT) in the stomach for optimal drug release and absorption (see, e.g., Arza et al., AAPS PharmSci Tech, 2009; 10, 220-226). In some embodiments, coatings for providing a controlled, delayed, or extended release may be applied to the compositions of the invention or to a core containing the compositions, and may comprise a pharmaceutically acceptable ingredient in an amount sufficient to provide a delayed release from, for example, about 1 hour to about 7 hours following ingestion before release of the active agents. In some embodiments, suitable coatings include one or more differentially degradable coatings including pH-sensitive coatings (enteric coatings), or non-enteric coatings having variable thickness to provide differential release of the active agents. Many other types of modified release systems will be known to those of skill in the art. Non-limiting examples of additional delivery systems include both polymer- and non-polymer-based systems, silastic systems, peptide-based systems, wax coatings, bioerodible dosage forms, and compressed tablets using conventional binders (see, e.g., Liberman et al., Pharmaceutical Dosage Forms, 2 Ed., v.1, 209-214, 1990; Singh et al., Encyclopedia of Pharm. Technology, 2nd Ed., 751-753, 2002; U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983).

In some embodiments, a composition comprising a compound provided herein is formulated as a pharmaceutically acceptable oral liquid dosage form. Non-limiting examples of oral liquid dosage forms include tinctures, drops, emulsions, syrups, elixirs, suspensions, and solutions, and the like. In some embodiments, oral liquid dosage forms may be formulated with any pharmaceutically acceptable excipient known to those of skill for the preparation of liquid dosage forms, and with solvents, diluents, carriers, excipients, and the like, chosen as appropriate to the solubility and other properties of the active agents and other ingredients. Non-limiting examples of solvents include, e.g., water, glycerin, simple syrup, alcohol, medium chain triglycerides (MCT), and combinations thereof.

In some embodiments, oral liquid dosage forms may be monophasic or biphasic, the former being a substantially homogenous solution dissolved in water or non-aqueous solvent, while the latter refers to oral liquid dosage forms in which the active ingredients do not fully dissolve in common solvents. In some embodiments, over time, the solid particles (i.e., the active agents) within the oral liquid dosage form may form a precipitate at the bottom of the container-requiring vigorous shaking to redisperse the active ingredients. Non-limiting examples of monophasic liquid forms include syrups, linctuses, spirits/essences, elixirs, and fluid extracts. Non-limiting examples of biphasic liquid forms include oral suspensions, oral emulsions, and mixtures.

Liquid dosage forms for oral administration may be prepared as liquid suspensions or solutions using a sterile liquid, such as but not limited to, an oil, water, an alcohol, combinations of pharmaceutically suitable surfactants, suspending agents, and emulsifying agents. In some embodiments, liquid formulations also may be prepared as single dose or multi-dose beverages. In some embodiments, suspensions may include oils. Such oils include but are not limited to peanut oil, sesame oil, cottonseed oil, corn oil, and olive oil. Suitable oils also include carrier oils such as MCT and long chain triglyceride (LCT) oils. In some embodiments, as suspension preparation may also contain esters of fatty acids such as ethyl oleate, isopropyl myristate, fatty acid glycerides, and acetylated fatty acid glycerides. In some embodiments, suspension formulations may include alcohols, such as ethanol, isopropyl alcohol, hexadecyl alcohol; glycerol, and propylene glycol. In some embodiments, ethers, such as polyethylene glycol; petroleum hydrocarbons, such as mineral oil and petrolatum; and water may also be used in suspension formulations. In some embodiments, a suspension can thus include an aqueous liquid or a non-aqueous liquid, an oil-in-water liquid emulsion, or a water-in-oil emulsion.

Dosage forms for oral administration may be aqueous suspensions such as aqueous oral dispersions, emulsions, solutions, and syrups (see, e.g., Singh et al., Encyclopedia of Pharm. Technology, 2nd Ed., 751-753, 2002). In addition to the active agents, the liquid dosage forms may comprise additives, such as one or more (a) disintegrating agents, (b) dispersing agents, (c) wetting agents, (d) preservatives, (e) viscosity enhancing agents, (f) sweetening agents, and/or (g) flavoring agents. In addition to the additives listed above, the liquid formulations of the invention, in some embodiments, may also comprise inert diluents commonly used in the art such as water or other solvents, solubilizing agents, emulsifiers, flavoring agents, and/or sweeteners. In some embodiments, co-solvents and adjuvants also may be added to a formulation.

In embodiments, effervescent powders containing the compositions of the invention may be prepared. In embodiments, effervescent salts are used to disperse medicines in water for oral administration. In embodiments, effervescent salts also may be packaged as single dose or multi-dose drink mixes, alone or in combination with other ingredients, such as vitamins or electrolytes. In embodiments, effervescent salts are granules or coarse powders containing a medicinal agent in a dry mixture, usually composed of sodium bicarbonate and sodium carbonate, citric acid, and/or tartaric acid. In embodiments, when salts of the invention are added to water, the acids and the base react to liberate carbon dioxide gas, thereby causing “effervescence.” In embodiments, any acid-base combination that results in the liberation of carbon dioxide may be used if the ingredients are suitable for pharmaceutical use and result in a pH of about 6.0 or higher.

In some embodiments, the compositions of the invention are formulated in a pharmaceutically acceptable transdermal application, and delivered transdermally. Generally speaking, transdermal delivery involves contacting the formulations of the invention with a subject’s skin under conditions effective for the active agent(s) to penetrate the skin and cause an effect. Non-limiting examples of transdermal formulations include ointments, creams, suspensions, lotions, pastes, gels, sprays, foams, oils, and the like, and any combination thereof.

An exemplary transdermal delivery form is a transdermal “patch” which contains the pharmaceutical compositions. Transdermal patches may be used to provide continuous or discontinuous infusion of the compounds described herein in controlled amounts. Such patches may be constructed for continuous, gradual, pulsatile, or on demand delivery of pharmaceutical agents. In some embodiments, a patch will be a medicated adhesive patch, i.e., a patch impregnated with a composition of the invention for application onto the skin. In some embodiments, a patch may be a single-layer or multi-layer drug-in-adhesive patch, wherein the one or more adhesive layers also contain the active agents. In some embodiments, a patch also may be a “matrix” (or “monolithic”) patch, wherein the adhesive layer surrounds and overlays the drug layer (wherein a solution or suspension of the active agents is in a semisolid matrix). In some embodiments, a “reservoir” patch may also be used, comprising a drug layer, typically as a solution or suspension of the active agents in a liquid compartment (i.e., the reservoir), separate from an adhesive layer. In some embodiments, a patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized.

In some embodiments, the compositions of the invention may also be prepared as formulations designed for subcutaneous, intravenous, intra-arterial, intraperitoneal, intraosseous, intramuscular, intrathecal, or intracerebroventricular, injection. In some embodiments, injection formulations may be prepared by dissolving, suspending, or emulsifying the active agent(s) in an aqueous or nonaqueous solvent, non-limiting examples of which include oils, such as vegetable oil, synthetic aliphatic acid glycerides, and esters of higher aliphatic acids or propylene glycol; and may also contain additives such as solubilizers, stabilizers, and suspending, preserving, wetting, emulsifying, dispensing, and isotonic agents.

In some embodiments, the compositions of the invention are formulated in a pharmaceutically acceptable nanostructured formulation, such as a nanoemulsion, a nanocapsule, a nanoparticle conjugate, or a nano-encapsulated oral or nasal spray. In some embodiments, preparations of the compositions of the invention as certain nanostructured formulations may be prepared by reference to the general knowledge of the art (see, e.g., Jaiswal et al., 3 Biotech, 5(2):123-127, 2015). The prefix “nano” as used in the terms describing various embodiments of a nanostructured formulation denotes a size range in the nanometer (“nm”) scale. Accordingly, sizes of such nanoparticle delivery vehicles include those in the range of about 1 to about 100 nm, about 100 to about 200 nm, about 200 to about 400 nm, about 400 to about 600 nm, about 600 to about 800 nm, and about 800 to about 1000 nm, as well as “microparticles” in the range of about 1000 to about 2000 nm (1-2 micrometer (“μm”) scale). Particles of certain sizes may be particularly advantageous depending on the method of administration, as will be immediately appreciated by one of skill (e.g., for oral liquid emulsion versus for transdermal or topical application). In some embodiments, lipid-based nanoparticles (LBNPs) such as liposomes, solid lipid nanoparticles (SLN), or nanostructured lipid carriers (NLC) are used.

In some embodiments, the active ingredients, such as the compounds described herein, are mixed with an excipient, diluted by an excipient, or enclosed within, encapsulated by, or attached to a carrier in the manufacture of a composition, such as a pharmaceutical composition. In some embodiments, the excipient serves as a diluent, it can be a solid, semi-solid, or liquid material, which acts as a vehicle, carrier, or medium for the active ingredient. In some embodiments, the compositions can be in the form of, e.g., tablets, pills, lozenges, sachets, cachets, elixirs, suspensions, emulsions, solutions, syrups, aerosols (as a solid or in a liquid medium), ointments, soft or hard gelatin capsules, suppositories, sterile injectable solutions, and sterile packaged powders. In some embodiments, it may be necessary to mill the active agent to provide the appropriate particle size prior to combining with the other ingredients. In some embodiments, if an active agent is substantially insoluble, it ordinarily is milled to a particle size of less than about 200 mesh. Different embodiments include immediate, delayed, extended, and controlled release forms. Many other variations are possible and known to those skilled in the art.

It should be readily appreciated that the compositions of the invention are not limited to combinations of a single compound, or (when formulated as a pharmaceutical composition) limited to a single carrier, diluent, and/or excipient alone, but may also include combinations of multiple compounds (including additional active compounds), and/or multiple carriers, diluents, and excipients. Pharmaceutical compositions of this invention thus may comprise a compound of Formula (I) together with one or more other active agents (or their derivatives and analogs) in combination, together with one or more pharmaceutically-acceptable carriers, diluents, and/or excipients, and additionally with one or more other active compounds.

In some embodiments, a formulation of the invention will be prepared so as to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, entheogenic, entactogenic or empathogenic, psychedelic, nootropic, sedative, and stimulant effects.

"Synergistic effects" should be understood to include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components when applied alone, thereby producing "1+1>2." One such method is the isobologram analysis (or contour method) (see Huang et al., Front. Pharmacol., 10:1222, 2019).

The goal of increasing an existing therapeutic effect, providing an additional therapeutic effect, increasing a desired property such as stability or shelf-life, decreasing an unwanted effect or property, altering a property in a desirable way (such as pharmacokinetics or pharmacodynamics), modulating a desired system or pathway (e.g, a neurotransmitter system), or otherwise inducing synergy, in some embodiments is achieved by the inclusion of an additional active compound.

Such additional active compounds may be selected from the group including amino acids, antioxidants, anti-inflammatory agents, analgesics, antineuropathic and antinociceptive agents, antimigraine agents, anxiolytics, antidepressants, antipsychotics, anti-PTSD agents, cannabinoids, dissociatives, immunostimulants, anti-cancer agents, antiemetics, orexigenics, antiulcer agents, antihistamines, antihypertensives, anticonvulsants, antiepileptics, bronchodilators, neuroprotectants, entheogens, entactogens and empathogens, psychedelics, monoamine oxidase inhibitors, tryptamines, terpenes, phenethylamines, sedatives, stimulants, nootropics, and vitamins. These ingredients may be in ion, freebase, or salt form, and may be isomers, prodrugs, derivatives (preferably physiologically functional derivatives), or analogs.

For any of the compounds described herein, substitution of the compound by its ion, free base, salt form, polymorph, hydrate or solvate form, co-crystal, or an isomer or enantiomerically enriched mixture, shall be understood to provide merely an alternative embodiment still within the scope of the invention (with modifications to the formulation and dosage amounts made according to the teachings herein and ordinary skill, if necessary or desired). Further, compositions within the scope of the invention should be understood to be open-ended and may include additional active or inactive compounds and ingredients.

In some preferred embodiments, compounds of Formula (I), or pharmaceutically acceptable salts, hydrates, solvates, or pro-soft drugs thereof, are produced and tested in compliance with current Good Manufacturing Practice ("GMP" or "cGMP") requirements.

The type of formulation employed for the administration of the compounds employed in the methods of the invention generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

b. Route of Administration

A "route of administration" is the path by which the compound or composition is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract).

In some aspects, provided are compositions comprising a compound described herein, such as pharmaceutical compositions, that are suitable for administration by a variety of routes. Non-limiting examples of routes of administration include enteral administration, such as oral, sublingual, buccal, and rectal administration; parenteral administration, including bolus injection or continuous infusion, intravenous, intra-arterial, intraperitoneal, intraosseous, intramuscular, intrathecal, intracerebroventricular, vaginal, ocular, nasal, cutaneous, topical, otic, ocular, transdermal, and subcutaneous administration.

In some embodiments, as appreciated by one of skill in the art, the compounds employed in the methods of the invention are effectively administered as oral solid and oral liquid dosage forms; sublingually or buccally; as injections, including intravenous, intra-arterial, intraperitoneal, intraosseous, intramuscular, intrathecal, and intracerebroventricular; rectally, vaginally, ocularly, nasally, cutaneously, topically, optically, transdermally, and subcutaneously.

c. Methods of Administration

In some aspects, provided are methods of administration or methods of administering a compound described herein. As used herein, the terms "subject," "user," "patient," and "individual" are used interchangeably, and refer to any mammal, preferably a human. Such terms will be understood to include one who has an indication for which a compound, composition, or method described herein may be efficacious, or who otherwise may benefit by the invention. In general, all of the compounds, compositions, and methods of the invention will be appreciated to work for all individuals, although individual variation is to be expected, and will be understood.

The invention provides methods for using therapeutically effective amounts of the pharmaceutical compositions of the invention in a mammal, and preferably a human. Such methods include those for treating a mental health disorder and for improving mental health and functioning, including in a healthy individual.

Administration of pharmaceutical compositions in an "effective amount," a "therapeutically effective amount," a "therapeutically effective dose," or a "pharmacologically effective amount," refers to an amount of an active agent that is sufficient to provide the desired therapeutic effect, for example, relieving to some extent one or more of the symptoms of the disease or condition being treated. The result can be reduction and/or alleviation of the signs, symptoms, or causes of a disease or disorder, or any other desired alteration of a biological system. The term "therapeutically effective amount" includes, for example, a prophylactically effective amount.

An "effective amount" of a compound disclosed herein is an amount effective to achieve a desired pharmacologic effect or meaningful therapeutic improvement. It is understood that "an effect amount" or "a therapeutically effective amount" can vary from subject to subject, due to variation in metabolism of a compound, such as a compound described herein, of age, weight, general condition of the subject, the condition being treated, the severity of the condition being treated, and the judgment of the prescribing physician. The effective amount will vary depending upon the subject and the disease condition being treated or health benefit sought, the weight and age of the subject, the severity of the disease condition or degree of health benefit sought, the manner of administration, and the like, all of which can readily be determined by one of skill. Additionally, pharmacogenomic (the effect of genotype on the pharmacokinetic, pharmacodynamic or efficacy profile of a therapeutic) information about a particular patient may affect dosage used.

As used herein, "therapeutic effect" or "therapeutic efficacy" means the responses(s) in a mammal, and preferably a human, after treatment that is judged to be desirable and beneficial. Hence, depending on the disorder to be treated, or improvement in physiological or psychological functioning sought, and depending on the particular constituent(s) in the compositions of the invention under consideration, those responses shall differ, but would be readily understood by those of skill. For example, in some embodiments, "therapeutic effect" may refer to an effect caused by the pharmaceutical composition of the invention, or its use in a method of the invention, such as the treatment of a mental health disorder.

"Therapeutically effective dose" refers to the dose necessary to elicit a desired result within a patient undergoing treatment. A therapeutically effective dose therefore may, in some embodiments, refer to a dose of the pharmaceutical composition or therapeutic combination necessary to deliver measurable patient-specific biologic effects in the treatment or prevention of a condition or disorder. A "therapeutically effective dose" may be used interchangeably with a "therapeutically effective amount" or an "effective amount."

d. Dosing

It will be readily appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

In some embodiments, the pharmaceutical composition of the invention comprises the compounds described herein (e.g., a compound of Formulas (I)-(V)) in an amount so that a single dose is (whether or not such dose is present in a unit dosage form), about 1 mg or less (including a dose of about 0.5 mg or less, about 0.25 mg or less, about 0.1 mg or less, about 0.05 mg or less, about 0.005 mg or less, about 0.001 mg or less, and about 0.0005 mg or less), or at least about 1 mg or more, including 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, and 200 mg, as well as amounts within these ranges. In some embodiments, a single dose may be greater than 200 mg, including 225 mg, 250 mg, or greater than 250 mg.

In some embodiments, the pharmaceutical composition of the invention comprises the compounds described herein (e.g., a compound of Formulas (I)-(V))) in an amount so that a single dose is (whether or not such dose is present in a unit dosage form), when administered to a patient, about 1 mg/kg or less (including a dose of about 0.5 mg/kg or less, about 0.25 mg/kg or less, about 0.1 mg/kg or less, about 0.05 mg/kg or less, about 0.005 mg/kg or less, about 0.001 mg/kg or less, and about 0.0005 mg/kg or less), or at least about 1 mg/kg or more, including 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, as well as amounts within these ranges. In some embodiments, a single dose may be greater than 5.0 mg/kg, including 7.5 mg/kg, 10.0 mg/kg, or greater than 10 mg/kg.

It will be understood that, in some embodiments, the dose actually administered will be determined by a physician, in light of the relevant circumstances, the method of delivery, (i.e., methods that are systemic and that are not subject to first pass effect will require less of a dose than those which are metabolised prior to entering the bloodstream); the age of the patient, the weight of the patient, whether the patient has any comorbidities (i.e., any other medical conditions simultaneously present within a patient), other medications the patient is taking (routinely or presently), and any patient-specific aspects that could affect the way in which the pharmaceutical composition interacts with the patient, such as variations in metabolism, variations in patient response, etc., and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately.

In such embodiments, the pharmaceutical compositions may be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Dosage levels, including starting and maintenance dosages if different, thus may differ from patient to patient, for individual patients across time, and for different pharmaceutical compositions and formulations, but shall be able to be determined with ordinary skill. Determination of appropriate dosing shall include not only the determination of single dosage amounts, but also the determination of the number and timing of doses, and the time(s) of day or time(s) during a psychotherapeutic session preferable for their administration.

Dose amount, frequency or duration may be increased or reduced, as indicated by the clinical outcome desired, status of the pathology or symptom, any adverse side effects of the treatment or therapy, or concomitant medications. The skilled artisan with the teaching of this disclosure in hand will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

In other embodiments, appropriate dosages to achieve a therapeutic effect, including the upper and lower bounds of any dose ranges, can be determined by an individual, including an individual who is not a clinician, by reference to available public information and knowledge, and reference to subjective considerations regarding desired outcomes and effects.

e. Pharmaceutical Kits

In some embodiments, especially where a formulation is prepared in single unit dosage form, suggested dosage amounts shall be known by reference to the format of the preparation itself. In other embodiments, suggested dosage amounts may be known by reference to the means of administration or by reference to the packaging and labeling, package insert(s), marketing materials, training materials, or other information and knowledge available to those of skill or the public. Another aspect of this disclosure therefore provides pharmaceutical kits containing a pharmaceutical composition or formulation of the invention, suggested administration guidelines or prescribing information therefor, and a suitable container. Individual unit dosage forms can be included in multi-dose kits or containers. Pharmaceutical formulations also can be packaged in single or multiple unit dosage forms for uniformity of dosage and ease of administration. Accordingly, another aspect of this disclosure provides pharmaceutical kits containing a pharmaceutical composition or formulation of the invention, suggested administration guidelines or prescribing information therefore, and a suitable container. Individual unit dosage forms can be included in multi-dose kits or containers. Pharmaceutical formulations also can be packaged in single or multiple unit dosage forms for uniformity of dosage and ease of administration.

D. METHODS OF TREATMENT

In some aspects, provided herein are methods of treatment comprising administration of a compound described herein. In some embodiments, provided are methods for use in treating a disease or condition in a subject. In some embodiments, the compounds described herein are used to treat CNS disorders, mental conditions or mental health disorders, and psychiatric or neuropsychiatric disorders.

As used herein, the terms "treating" or "treatment" include preventing or delaying the appearance of clinical symptoms of a disease or condition developing within a subject afflicted with, or predisposed to, the disease or condition but who does not yet experience or display clinical or subclinical symptoms of the disease or condition; inhibiting the disease or condition, i.e., arresting or reducing the development of the disease or condition, or at least one clinical or subclinical symptom thereof, and relieving the disease or condition, i.e., causing regression of the disease or condition or at least one of its clinical or subclinical symptoms.

In some embodiments, a therapeutically effective amount of the pharmaceutical composition of the invention is administered to a subject in need thereof. As it relates to the invention, "effective," "an effective amount," "effective dose," "sufficient amount," "sufficient dose," "therapeutically effective," "a therapeutically effective amount," "a therapeutically effective dose," "therapeutically sufficient amount," "therapeutically sufficient dose," or "a pharmacologically effective amount" refer to an amount of an active agent that is sufficient to provide the desired therapeutic effect. An effective amount will vary depending upon the subject and the disease condition being treated or health benefit sought, the weight and age of the subject, the severity of the disease condition or degree of health benefit sought, the manner of administration, and the like, all of which will be readily determined by one of skill.

As used herein, "therapeutic effect" or "therapeutic efficacy" means the responses(s) in a mammal, and preferably a human, after treatment that is judged to be desirable and beneficial. Hence, depending on the disorder to be treated, or improvement in physiological or psychological functioning sought, and depending on the particular constituent(s) in the compositions of the invention under consideration, those responses shall differ, but would be readily understood by those of skill. In preferred embodiments, the mammal is a human.

Measures of therapeutic effect include outcome measures (primary or secondary), endpoints, effect measures, and measures of effect within clinical or medical practice or research which can be used to assess an effect (positive and/or negative) of an intervention or treatment, whether patient-reported (e.g., questionnaires); based on other patient data (e.g., patient monitoring); gathered through laboratory tests such as from blood or urine; through medical examination by a doctor or other medical professional, or by digital means, such as by using electronic tools such as online tools, smartphones, wireless devices, biosensors, or health apps.

In some embodiments, the compounds described herein are administered (to the patient alone, with another patient as in couples therapy, or as part of group therapy) in the presence of one or more therapists in a therapeutic setting to facilitate psychotherapy. Numerous such treatment paradigms have been described in the art, using terms such as psychedelic-assisted psychotherapy or drug-assisted therapy (see, e.g., Sessa et al., *Frontiers in Psychiatry,* 10, 138, 2019). Drug-assisted therapy, broadly, includes a range of related approaches that involve at least one session where the patient ingests a psychoactive compound or substance and is monitored, supported, and/or otherwise engaged (such as in one or more forms of psychotherapy) by one or more trained mental health professionals while under the effects of said substance (see, e.g., Schenberg, *Front. Pharmacol.*, v.9, 2018). In some embodiments, two therapists are present and/or oversee administration of a compound or composition as described herein. In some embodiments, the two therapists are a dyadic therapist team.

In various embodiments, a patient may be administered a compound or composition and be monitored, a patient may be administered a compound or composition and receive psychological support, and a patient may be administered a compound or composition and receive psychotherapy, and such may take place for example with a psychiatrist, medical doctor, clinical psychologist, or other trained clinician, as well as with a "guide" or non-clinical practitioner. "Therapist" herein therefore may refer to any person who treats a patient using the compositions and methods of the invention, whether that person is a care provider, a psychiatrist, clinical psychologist, clinical therapist, psychotherapist, or other trained counselor, facilitator, or guide, and who may or may not be a trained counselor. Generally, therapists are certified in the use of the treatment manual for the drug-assisted therapy or psychotherapy administered (and familiar with any applicable requirements in a Risk Evaluation and Mitigation Strategies (REMS) or its equivalents), and will have completed or have the intent to complete the appropriate training in delivering one or more forms of drug-assisted therapy or psychotherapy.

Protocols have been developed for the standardization of procedures which emphasize a high degree of care (see, e.g., Johnson, Richards, & Griffiths (2008. Human hallucinogen research: guidelines for safety. *Journal of psychopharmacology,* 22(6), 603-620)), such as the therapeutic approach used by MAPS to treat patients with PTSD using MDMA (e.g., as described in Mithoefer et al. A Manual for MDMA-Assisted Therapy in the Treatment of PTSD (2017)). Other forms of MDMA-assisted or psychedelic-assisted psychotherapy which may be applied as part of methods of drug-assisted psychotherapy herein, will be known to those in the field and are disclosed, for example, in Grof (2008) *LSD Psychotherapy* (Ben Lomond, CA: Multidisciplinary Association for Psychedelic Studies); Passie (2012) *Healing with Entactogens: Therapist and Patient Perspectives on MDMA-Assisted Group Psychotherapy* (Ben Lomond, CA: Multidisciplinary Association for Psychedelic Studies); Johnson, Richards, & Griffiths (2008. Human hallucinogen research: guidelines for safety. *Journal of psychopharmacology,* 22(6), 603-620); Sessa & Fischer (2015, *Underground MDMA-, LSD-and 2-CB-assisted individual and group psychotherapy in Zurich*: Outcomes, implications and commentary. *Drug Science, Policy and Law,* 2, 2050324515578080); Schmid, Gasser, Oehen, & Liechti (2020. Acute subjective effects in LSD- and MDMA-assisted psychotherapy. *Journal of psychopharmacology,* 0269881120959604); Greer & Tolbert (1998. A method of conducting therapeutic sessions with MDMA. *Journal of psychoactive drugs,* 30(4), 371-379); Mithoefer et al. A Manual for MDMA-Assisted Therapy in the Treatment of PTSD (2017); Mithoefer (2013. MDMA-assisted psychotherapy: How different is it from other psychotherapy. *Manifesting minds: A review of psychedelics in science, medicine, sex, and spirituality,* 125).); see also U.S. Pat. App. No. 2020/0360311A1, generally discussing drug-assisted psychotherapy practices, which can be applied with MDMA.

In some embodiments, the compounds described herein are administered to a subject along with the provision of therapy or the use of one or more therapeutic techniques. Non-limiting examples of therapy or therapeutic techniques include breathing exercises, mindfulness, acceptance and commitment therapy (ACT), psychoanalytic therapy, cognitive behavioral therapy, and other similar practices. In such embodiments, the compounds described herein may be administered to a patient in a controlled environment wherein the patient is monitored (e.g., a treatment room, such as but not limited to a traditional practitioner's office; an inviting space, wherein temperature, lighting, scent, music, the display of symbolic items, and/or other aspects of "setting" are tailored to the patient undergoing the dosing session, etc.), or may be prescribed to a patient with instructions to self-administer at a place of the patient's choosing.

In some embodiments, the compounds described herein are used to treat CNS disorders, including mental conditions and mental health disorders, and psychiatric and neuropsychiatric disorders. In some embodiments, such disorders and conditions will be related to or affected by one or more monoamine neurotransmitter systems, such as the serotonin, dopamine, and/or norepinephrine systems. Non-limiting examples of disorders and conditions that may be treated by the compounds and compositions disclosed herein include post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, and dissociative disorders.

The term "mental health disorder" refers to a disease condition that generally involves negative changes in emotion, mood, thinking, or behavior. Examples of mental health disorders include anxiety and stressor-related disorders, dissociative disorders, eating disorders, mood disorders, obsessive-compulsive and related disorders, personality disorders, bipolar and related disorders, schizophrenia and related disorders, sexuality, gender dysphoria, and paraphilias, somatic symptom and related disorders, suicidal behavior and self-injury, and substance-related disorders. (See Merck Manual of Diagnosis and Therapy, 20th Ed. (2018).) In some embodiments, included among mental health disorders are depression including in forms such as treatment-resistant depression and major depressive disorder (including bipolar, manic, and hypomanic disorders that may accompany or correlate with depressive disorders), dysthymia, anxiety and phobia disorders (including generalized anxiety, social anxiety, panic, post-traumatic stress and adjustment disorders), feeding and eating disorders (including binge eating, bulimia, and anorexia nervosa), other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders (including antisocial, avoidant, borderline, histrionic, narcissistic, obsessive compulsive, paranoid, schizoid and schizotypal personality disorders), attachment disorders, autism, and dissociative disorders.

A variety of methods for screening or assessing a subject for a mental health disorder exist. In some embodiments, a diagnosis of a mental health disorder is facilitated with use of the Diagnostic and Statistical Manual of Mental Disorders, such as the DSM-5. In embodiments, diagnosis of a mental health disorder is facilitated with use of self-reported or observer-report surveys or questionnaires. Non-limiting examples of such questionnaires include the Patient Health Questionnaire 9 (PHQ-9), Generalized Anxiety Disorder 7 (GAD-7), PTSD Checklist for DSM-5 (PCL-5), Alcohol Use Disorders Identification Test (AUDIT), Binge Eating Scale (BES), Obsessive-Compulsive Inventory (OCI), Personality Disorders Questionnaire (PDQ-IV), Dissociative Experiences Scale (DES), Drug Use Questionnaire (DAST-20), Mood Disorder Questionnaire (MDQ), and other like questionnaires. In embodiments, alternative questionnaires, such as the Clinical Global Impression-Improvement scale (CGI-I), may be used to assess improvement of a subject's mental health state, such as by comparing baseline responses to responses after a treatment intervention. In some embodiments, any of the diagnostic manuals and assessments described, and other similar tools, may be used to confirm a reduction in symptoms, a reduction in symptom severity, or elimination of symptoms and/or a previous diagnosis.

E. SYNTHESIS OF SELECT COMPOUNDS DESCRIBED HEREIN

Methods for synthesis of the compounds described herein and any necessary starting materials are either described in the art or will be readily apparent to the skilled artisan in view of general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the compounds described herein.

The skilled artisan understands that while the reaction schemes depict exemplary reagents and/or solvents, alternatives are also embraced by the present disclosure. It is within the capabilities of one of ordinary skill of the art-through routine experimentation and without undue burden—to select alternative reagents and/or solvents for any particular reaction step, choose which of the various possible synthetic routes may be used to obtain a disclosed compound, or modify the reaction conditions or reaction sequences disclosed herein. For example, while $Pd(OAc)_2$ is depicted below in the Exemplary Synthesis of IIA-2 HCl as a $Pd^{II}$ reagent, the skilled artisan understands that alternative $Pd^{II}$-containing reagents (e.g., $Pd(PPh_3)_2Cl_2$) may be suitable for the same purpose. Likewise, the conversion of an Boc-protected amine to an N-methylamine product—e.g., in the depicted syntheses of IIA-2 HCl or IIA-5—may involve an additional methylation reagent (e.g., methyl iodide, methyl bromide), optionally in combination with a suitable base (e.g., triethylamine, diisopropylethylamine). The present disclosure will be understood to include such modifications and others that one of ordinary skill may employ to arrive at disclosed compounds according to the general synthesis strategies provided herein.

Exemplary Synthesis (I-2; I-2 HCl):

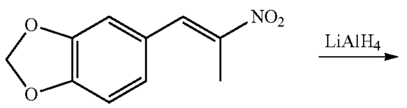

1

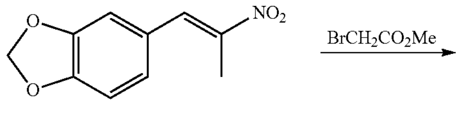

2 MDA

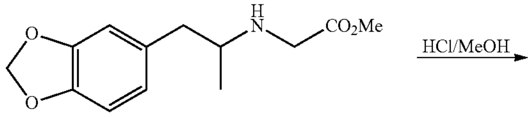

I-2

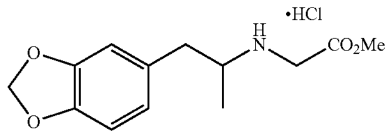

I-2 HCl

Exemplary Synthesis (I-5; I-5 HCl):

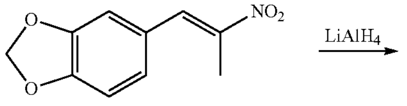

1

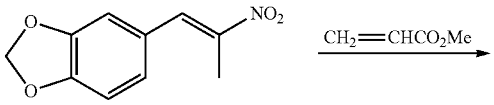

2 MDA

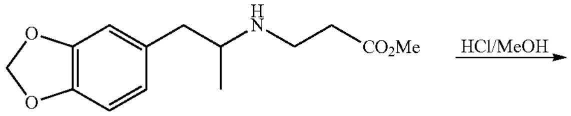

I-5

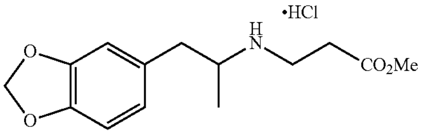

I-5 HCl

Exemplary Synthesis (IIA-2 HCl):
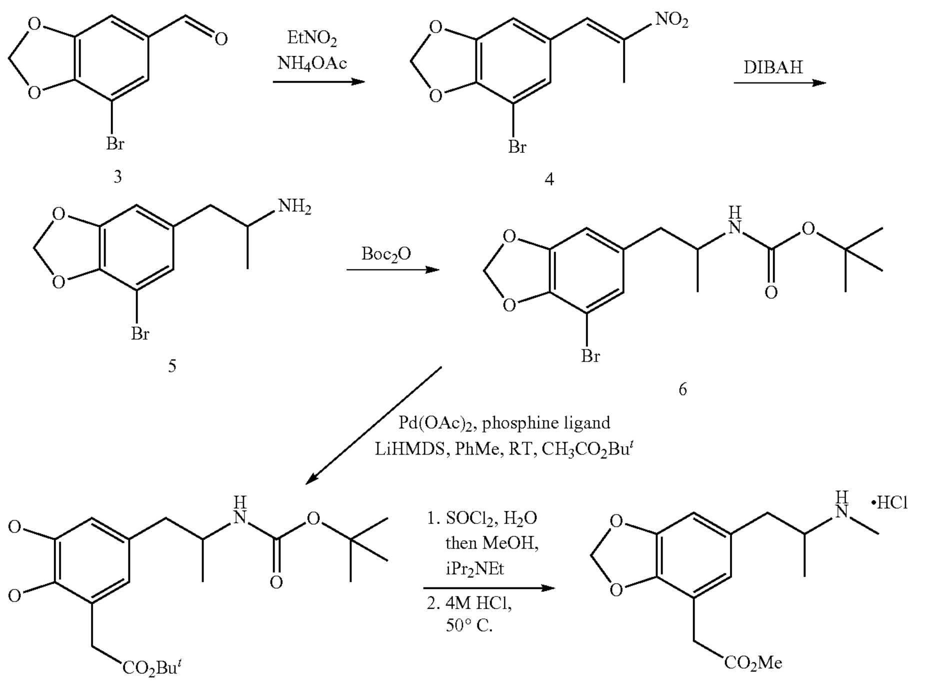
3
4
5
6
7
IIA-2 HCl
Exemplary Synthesis (IIA-5 HCl):
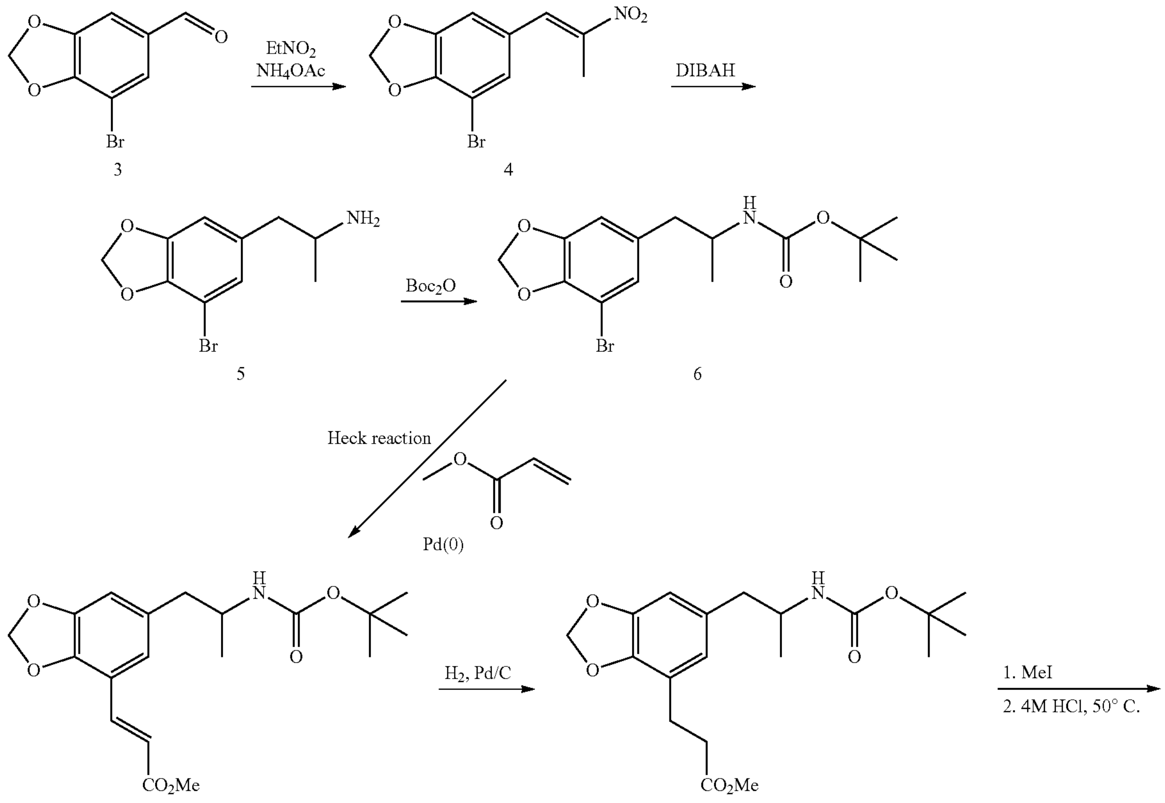
3
4
5
6
9
10

-continued

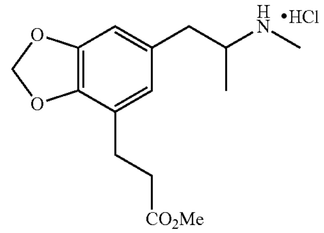

IIA-5 HCl

F. ADDITIONAL EXAMPLES

That the compounds and compositions of the invention are useful to treat the conditions and disorders discussed herein may be shown in part by the following Examples. While every attempt is made to use the present and future tenses, for avoidance of doubt, these Examples (and any examples discussed elsewhere, even if not so labeled, and unless stated otherwise) are prophetic examples. It will be readily understood and appreciated that these Examples are merely exemplary and are intended to be illustrative and not to be limiting.

Example 1: Functional DAT Uptake Assay in Recombinant hDAT-CHO Cells

Purpose: In this Example, the inhibitory activity of tested compounds on dopamine active transporter (DAT) function is determined.

Methods and Procedure: Potency of disclosed compounds for inhibiting DAT function is measured using an uptake assay in a recombinant CHO cell line that stably expresses human DAT (hDAT-CHO). Potency is measured in terms of $pIC_{50}$ by testing for inhibition of [$^3$H]-dopamine uptake in hDAT-CHO cells in a 384-well format scintillation proximity assay (SPA).

On experiment days, hDAT-CHO cells are detached using Versene and added at a density of approximately 300,000 cells/mL to the SPA Mixture, which contains the following components in assay buffer (20 mM HEPES, 145 mM NaCl, 5 mM KCl, 2 mM $CaCl_2$, 1 mM $MgCl_2$, 5.5 mM glucose, 0.01% Pluronic F127, pH 7.3): 0.75 mg/mL SPA Imaging beads (RPNQ0001, PerkinElmer), 10 μM pargyline and 80 nM of [$^3$H]-dopamine (NET673, PerkinElmer). 20 μL/well of the SPA Mixture is added to 384 well plates containing 0.1 μL/well of test compound in neat DMSO (11 points of 1:5 serial dilution, 0.5% DMSO final) or 0.1 μL of DMSO (total uptake) or 0.1 μL of the standard inhibitor indatraline (at 1 μM final concentration, as nonspecific uptake). Plates are sealed with a Top-seal A and read using a Microbeta counter (PerkinElmer) after 45 minutes of incubation at room temperature. The raw experimental data (cpm) are elaborated for the determination of $pIC_{50}/IC_{50}$ values as % inhibition of specific uptake. Concentration-response curves of MDMA, MDDMA, citalopram and GBR-12909 are used as internal standards in all experiments, and the signal window is monitored in each plate performing Z' calculations, as described in Zhang et al., *J Biomol Screen.,* 1999; 4: 67-73.

Results and Significance: The results of tested compounds and reference compound MDMA are compared. The results will demonstrate the inhibitory activity of tested compounds on DAT, which is implicated in the uptake of dopamine. In comparison to MDMA, compounds that more potently inhibit DAT may further reduce DAT-mediated dopamine trafficking and resultant effects thereof on dopamine activity. Compounds that are less potent inhibitors of DAT are expected to have less of an effect on DAT function, such as DAT-mediated dopamine trafficking.

Example 2: Functional Serotonin Transporter (SERT) Assay in Recombinant hSERT-CHO Cells Purpose: The inhibitory activity of tested compounds on SERT function is determined.

Methods and Procedure: Potency of the compounds herein for inhibiting SERT function is measured using an uptake assay in a recombinant CHO cell line that stably expresses human SERT (hSERT-CHO). Potency is measured in terms of $pIC_{50}$ by evaluating inhibition of [$^3$H]-serotonin uptake in hSERT-CHO cells in a 384-well format scintillation proximity assay (SPA).

hSERT-CHO cells are detached using Versene and added at a density of 150,000 cells/mL to the SPA Mixture, containing the following components in the Assay Buffer (20 mM HEPES, 145 mM NaCl, 5 mM KCl, 2 mM $CaCl_2$, 1 mM $MgCl_2$, 5.5 mM glucose, 0.01% Pluronic F127, pH 7.3): 0.5 mg/mL SPA Imaging beads (RPNQ0001, PerkinElmer), 10 μM pargyline and 35 nM of [$^3$H]-serotonin (NET498, PerkinElmer). 20 μL/well of the SPA Mixture is added to 384 well plates containing 0.1 μL/well of test compound in neat DMSO (11 points of 1:5 serial dilution, 0.5% DMSO final), 0.1 μL of DMSO (total uptake), or 0.1 μL of the standard inhibitor indatraline (1 μM, nonspecific uptake). Plates are sealed with a Top-seal A and read using a Microbeta counter (PerkinElmer) after 120 minutes of incubation at room temperature. Raw experimental data (cpm) are elaborated for determination of $pIC_{50}/IC_{50}$ values as percentage (%) inhibition of specific uptake. Concentration-response curves of MDMA, MDDMA, citalopram and GBR-12909 are used as internal standards in all experiments, and the signal window is monitored in each plate performing Z' calculations, as described in Zhang et al., J Biomol Screen., 4: 67-73; 1999.

Results and Significance: The results of tested compounds and reference compound MDMA are compared. The results of the study will demonstrate the inhibitory activity of tested compounds on SERT, which is implicated in the uptake of serotonin. In comparison to MDMA, compounds that more potently inhibit SERT may further reduce SERT-mediated serotonin trafficking and resultant effects thereof on serotonin activity. Compounds that are less potent inhibitors of SERT are expected to have less of an effect on SERT function, such as SERT-mediated serotonin trafficking.

Example 3: Dopamine Release Assay in Rat Synaptosomes

Purpose: The effects of the compounds described herein on dopamine release are assessed.

Methods and Procedure: The potency of the tested compounds for stimulating dopamine (DA) release is measured by an endpoint release filtration assay in a 96-well format using rat synaptosomes, essentially as described by Sandtner et al., Mol Pharmacol. 2016; 89(1):165-75 and Baumann et al. Neuropsychopharmacol. 2013; 38:552-562, with some variations.

Broadly, one male rat is sacrificed and striatum/cortex regions are dissected over ice. The striatum portions are weighed and put in a glass tube for homogenization, containing ice-cold 0.32 M sucrose (dilution 1:24 w/v), while the frontal cortex tissue is diluted in ice-cold 0.32 M sucrose, 1:20 w/v. Tissues are homogenized and centrifuged for 10 mins at 1000×g. The two supernatants from striatum and cortex (crude synaptosomes) are retained on ice until use.

The test compounds are then serially diluted 1:4 in neat DMSO as concentration-response curves (CRC) of 11 points. To each well of a 2-mL 96 deep-well plate (Whatman UNIPLATE 96 well) are added: 2 μL of test compounds or 2 μL of DMSO (no-release condition) or 2 μL of MDMA 10 mM solution (final 50 μM, for maximal release), followed by 200 μL/well of complete Krebs-phosphate buffer (126 mM NaCl, 2.4 mM KCl, 0.83 mM $CaCl_2$, 0.8 mM $MgCl_2$, 0.5 mM $KH_2PO_4$, 0.5 mM $Na_2SO_4$, 11.1 mM Glucose, 0.05 mM pargyline, 1 mg/mL ascorbic acid, freshly added, pH 7.4), containing 1 μM reserpine to block vesicular uptake of substrate. Desipramine (100 nM) and citalopram (100 nM) are also added to the release assay buffer in order to inhibit NET and SERT uptake, respectively. The final compound dilution, then, is 1:200 in 0.5% DMSO.

[$^3$H]-Dopamine is added to the tube containing the crude striatal synaptosomes preparation, diluted 1:20 (v/v) in complete Krebs-phosphate buffer, and is incubated at RT and gently mixed for 60 minutes. Then, 200 μL/well of [$^3$H]-DA loaded synaptosomes are dispensed to the compound plate (final 400 μL/well) and the release reaction allowed to proceed for an additional 15 minutes at RT. The release is terminated by vacuum filtration and washing three times with 1 mL of saline solution (NaCl 0.9%) at RT. The retained radioactivity is counted in a scintillation counter after the addition of 50 μL/well Microscint-20.

The raw data (cpm) from residual radioactivity onto the filter are elaborated for the determination of $pEC_{50}/EC_{50}$ values. Specifically, the compound effect is expressed as the percent of maximal release obtained with 50 μM MDMA (100% release) in comparison to vehicle (0.5% DMSO, 0% release). Both MDMA and D-amphetamine in CRC are used as internal controls in each release experiment. In each plate, for both 0% and 100% of release, the signal window is monitored performing Z' calculations using raw data of four replicates.

Results and Significance: The DA release $pEC_{50}$ values of test compounds are determined and referenced with the observed $pEC_{50}$ of MDMA. Higher $pEC_{50}$ values indicate greater potency, while lower values indicate weaker potency. The results of the study will demonstrate the potency of the compounds for stimulating dopamine release. Stimulation of dopamine release may be leveraged to modulate the activity of the monoamine neurotransmitter.

Example 4: Serotonin Release Assay in Rat Synaptosomes

Purpose: The effects of the compounds described herein on serotonin release are assessed.

Methods and Procedure: The potency of the test compounds for stimulating release of serotonin (5-HT) is measured by an endpoint release filtration assay in a 96-well format using rat synaptosomes, as described for DA release, except that 5 nM [$^3$H]-serotonin is added to crude cortex synaptosomes preparation diluted 1:13 (v/v) in complete Krebs-phosphate buffer containing 1 μM Reserpine, 100 nM GBR12909 and 100 nM nomifensine to block vesicular, DAT, and NET uptake, respectively.

Synaptosomes are loaded with [$^3$H]-5HT for 60 minutes at RT. After dispensing loaded synaptosomes onto a compound plate (200 μL/well), the release reaction is allowed to proceed for an additional 15 minutes. The release is terminated by vacuum filtration and washing three times with 1 mL of saline solution (NaCl 0.9%) at RT. The retained radioactivity is counted in a scintillation counter after the addition of 50 μL/well Microscint-20.

The raw data (cpm) from residual radioactivity onto the filter are elaborated for the determination of $pEC_{50}/EC_{50}$ values. Specifically, the compound effect is expressed as the percent of maximal release obtained with 50 μM MDMA (100% release) in comparison to vehicle (0.5% DMSO, 0% release). Both MDMA and D-amphetamine in CRC are used as internal controls in each release experiment. In each plate, for both 0% and 100% of release, the signal window is monitored performing Z' calculations using raw data of four replicates.

Results and Significance: In this Example, the 5-HT release $pEC_{50}$ values of the test compound are determined and referenced with the observed $pEC_{50}$ of MDMA. Higher $pEC_{50}$ values indicate greater potency, while lesser values indicate weaker potency. The results of the study will show the potency of the test compounds for stimulating serotonin release. Stimulation of serotonin release may be leveraged to modulate the activity of the monoamine neurotransmitter.

Example 5: Intracellular Calcium Response in CHO Cells Expressing the Human 5-$HT_{2A}$ Receptor Purpose: The aim of the study is to assess the 5-$HT_{2A}$ receptor selectivity of the compounds described herein. Selectivity is assessed in agonist and antagonist modes.

Methods and Procedure: Selectivity for the serotonin 5-$HT_{2A}$ receptors is assessed by measuring $[Ca^{2+}]_i$ in a CHO recombinant cell line stably expressing the human 5-$HT_{2A}$ receptor, using Fluorometric Imaging Plate Reader (FLIPR TETRA, Molecular Devices).

The day before the experiment, CHO cells are seeded into clear-bottom 384-well plates at a density of 10,000 cells per well, in F-12K Medium (ThermoFisher #21127) supplemented with 10% dialyzed fetal bovine serum, and grown overnight at 37° C., 5% $CO_2$.

On the day of the experiment, the medium is replaced with assay buffer (20 mM HEPES, 145 mM NaCl, 5 mM KCl, 5.5 mM glucose, 1 mM $MgCl_2$, 2 mM $CaCl_2$ and 2.5 mM probenecid, pH 7.4) containing the cytoplasmic $Ca^{2+}$ indicator Fluo-4 AM at 2 μM and 0.02% Pluronic F-127. After an incubation of 45-60 minutes at 37° C., 0% $CO_2$, cells are washed by Microplate Washer (BIOTEK) 384 with the assay buffer, and the plate is transferred in the FLIPR TETRA. Then, intracellular fluorescence is measured in real time by FLIPR TETRA (excitation wavelength at 470-495 nm, emission wavelength at 515-575 nm), using a dual addition protocol. In the first addition, the test compounds are added to the cell plate (11 points of 1:4 serial dilution, 0.5% DMSO final) to evaluate their effect on intracellular calcium levels. In the event of a response, the signal is elaborated for the determination of $pEC_{50}/EC_{50}$ values. After 10 minutes of incubation, a second addition of a submaximal concentration of serotonin ($EC_{80}$) is performed. Inhibition of 5-HT response vs. vehicle effect (0.5% DMSO) is elaborated for the determination of $pIC_{50}/IC_{50}$ values. Concentration-response curves (CRC) of serotonin and LSD are used as internal controls in the agonist, full agonist, and partial agonist formats, respectively. A CRC of ketanserin is used as the internal antagonist control. The activity of MDMA is also assessed and used as a comparison for the compounds of the invention.

Results and Significance: Selectivity for the $5\text{-HT}_{2A}$ receptor, for example, as represented by the $pEC_{50}$, is determined for test compounds and compared to reference compound MDMA. The results of the study will illustrate the $5\text{-HT}_{2A}$ selectivity of the test compounds as agonists and antagonists and allow for comparisons of the same.

Example 6: In Vivo Analysis of Monoamines by Microdialysis in Rat Brain after Administration Purpose: The aim of the study is to assess the effect of administration of compounds described herein on extracellular dopamine (DA), serotonin (5-HT), and norepinephrine (NE) levels over time in the nucleus accumbens (NAcc).

Methods and Procedure: An in vivo microdialysis technique is applied to measure the over-time variations of DA, 5-HT, and NE extracellular (EC) concentrations in conscious, freely-moving Sprague Dawley rats. Levels of the neurotransmitters in microdialysis samples are determined using LC-MS/MS analysis. MDMA is used for comparative purposes.

For cannula implantation, rats are anesthetized with isoflurane 4% in oxygen (2-2.5 L/min), then the isoflurane concentration 2-2.5% is maintained via a nose cone adapted to the stereotaxic apparatus. The rats are treated with meloxicam (0.2 mg/kg, subcutaneously, SC; Meloxidolor) and amoxicilline (150 mg/kg, SC, Betamox LA). The skull is shaved and disinfected. Rats are then placed in a stereotaxic apparatus for small animals. One vertical guide cannula is inserted through a 1 mm hole drilled on the exposed skull. Coordinates, with respect to bregma, to target specific brain areas, followed indications from stereotaxic atlas of the rat brain. Specifically a guide cannula (MAB 4.12.IC, Agn Tho's AB, Lidingö, Sweden) is inserted in the NAcc (anteroposterior+1.6; lateral −1.6; dorsoventral −6.0). The guide cannula is then secured with dental cement and 2-4 screws. At the end of the surgery, the animal is isolated in a single cage during recovery, for a period of at least one week, during which animal health conditions are assessed twice daily and the weight recorded twice a week. Animals continue to be housed singly throughout the experiment. One day before the experiment, the cannula stylet is removed and a microdialysis probe with a dialyzing length of 2 mm (MAB 4.12.2 Cu, Agn Tho's AB, Lidingö, Sweden) is inserted.

Post-surgery, rats are maintained in a heating chamber prior to waking up in order to avoid hypothermia that could be caused by anaesthesia. 5 mL of physiologic solution is subcutaneously administered immediately after surgery, and once/day for 2-3 days, if signs of dehydration are noticed. Meloxicam (Meloxidolor) 0.2 mg/kg is again administered subcutaneously the day after surgery as well as 48 h after surgery together with Amoxicilline Long Acting (Betamox LA) 150 mg/kg. Health status and body weight is checked every day during the first week.

Disclosed compounds, MDMA, or vehicle (saline) are administered to rats according to a Latin square design over five separate experimental days (one day/week). In some examples, the compounds are administered by injection, such as subcutaneously, intraperitoneally, or intravenously. In other examples, the compounds are administered by the oral route.

On the day of the experiment, each animal is taken into the laboratory in its home cage. Inlet tubing of the probe is attached to a dual quartz-lined two channel liquid swivel mounted on a low mass spring counterbalance arm which, in turn, is connected to a gas-tight syringe on a microinfusion pump. Artificial cerebrospinal fluid (aCSF; containing KCl 2.5 mM, NaCl 125 mM, $CaCl_2$ 1.3 mM, $MgCl_2$ 1.18 mM, $Na_2HPO_4$ 2 mM, pH 7.4) is perfused through the probe (Univentor 864 Syringe Pump, Agn Tho's, Sweden) at a steady flow rate of 1 L/min. An equilibration period of about two hours of perfusion is allowed before collecting samples. Following the equilibration period, 4 basal samples are collected for each experimental animal followed by further 10 post-treatment samples. Samples are collected every 20 minutes (up to 3 hours and 20 minutes post-treatment) by means of a refrigerated auto-sampler (Univentor 820 Microsampler, Agn tho's, Sweden) maintained at 8° C. At the end of all experimental sessions, 2 L of 0.1% methylene blue solution will be injected through the microdialysis probe, animals will be euthanized, and their brains will be removed to check for the correct probe-position.

As noted, the concentration of DA, 5-HT and NE in CSF samples is determined using an optimized method based on LC-MS/MS analysis. Study samples are spiked with appropriate Internal Standard (IS) to improve the precision of the assay.

Liquid chromatography separations are performed using Agilent HP1100 system (Agilent Technologies) equipped with a binary pump, a column oven and a PAL CTC Autosampler. The LC system is coupled with an API4000 Triple Quadrupole System (ABSciex) equipped with a TIS ion source. Analyst software 1.6.2 (ABSciex) is used to control the instruments.

Results and Significance: The effects of the test compounds on the levels of the studied monoamine neurotransmitters are determined and compared to reference compound MDMA. The results of the study will illustrate the effect of compounds described herein on extracellular concentrations of 5-HT, DA, and NE in the rat brain and facilitate comparisons of the same.

Example 7: Pharmacokinetic Study of Intravenous and Oral Administration of Compounds in Rats Purpose: To assess the pharmacokinetics, including penetration into the brain, of the compounds described herein in rats following intravenous (IV) and oral administration (PO).

Methods and Procedure: Three experimental groups, as below, are included in the study:

- Group 1: Exemplary compound is administered via the IV route to three rats at a target dose level of 0.5 mg/kg. Blood and brain samples are collected at 2 h after IV administration.
- Group 2: Exemplary compound is administered via the IV route to three rats (brain penetration group) at a target dose level of 0.5 mg/kg. Blood and brain samples are collected at 2 h after IV administration.
- Group 3: Exemplary compound is orally administered to three rats at a target dose level of 1 mg/kg. Blood and brain samples are collected up to 24 h after oral administration.

All test formulations are prepared on the day of administration prior to dosing, stored at room temperature, and used as soon as possible. Formulations are prepared and administered by volume for both IV and oral dosing. Actual body weights are determined on the day of dose administration, and dose volumes are adjusted to the animal weight at time of dose administration.

Blood is collected into K3 EDTA tubes at each of the following time points post-administration:

Group 1 (IV): 0.083, 0.33, 1, 2, 4, 6, 8, and 24 hours after dosing

Group 2 (IV): 2 hours after dosing for terminal brain analysis

Group 3 (PO): 0.250, 0.5, 1, 2, 4, 6, 8, and 24 hours after dosing

Blood samples are thoroughly but gently mixed following collection and placed on wet ice. Within 0.5 h of collection, blood is centrifuged (3000 g for 10 min at approximately 4° C.). Within 0.5 h, 20 μL of each plasma sample is transferred into micronic tubes containing 80 μL of 0.1N Hepes buffer (pH 7.0-7.5). Residual plasma is transferred in micronic tubes as a second aliquot.

Brain specimens are diluted with 4 volumes of 0.1 N Hepes buffer and homogenized using the Precellys system. Blood and brain samples are assayed using an optimized method based on protein precipitation with acetonitrile followed by HPLC/MS-MS analysis. Given the unknown stability of the analytes in blood and brain, Calibration standards (CS) and Quality control samples (QC) are prepared in blood and brain samples on the day of dosing and stored together with study samples. It is assumed that this procedure accounts for any possible analyte degradation.

Study samples, CS, QC, and blanks are spiked with an internal standard (IS), to improve the precision of the assay. Study samples are analyzed together with CS, QC and blank samples (including double blanks). From the calibration curve, the linear range of the analytical method is determined and the lower/upper limits of quantitation are specified.

The results of blood and brain specimens are subjected to non-compartmental pharmacokinetic analysis using Phoenix WinNonlin 6.3, with the following parameters reported:

Calculated concentration of test items in the corresponding formulation (expressed as mg/mL), dose levels (expressed as mg/kg) for each compound, actual collection times (expressed as hh: mM), blood concentrations (expressed as ng/ml) for each compound, brain concentrations (expressed as ng/g) for each compound, PK parameters (IV: $C_{max}$, AUC, $CL_p$, $V_{ss}$, $t_{1/2}$, if applicable; oral (PO): $C_{max}$, $t_{max}$, AUC, F %, Fa %, $E_h$, $AUC_{BB}$ ratio, if applicable) for each compound, and abnormal clinical signs and relevant findings, if any.

Results and Significance: The results from IV and oral administration of the compounds described herein are determined and compared with reference compound MDMA. Results will show the pharmacokinetic properties, including the brain penetration, of such compounds. Pharmacokinetic parameters as detailed above are calculated, and penetration into the brain is represented by the determined concentration ratio of unbound drug in brain to blood ($K_{p,\ uu}$).

Example 8: Solubility Assessment of Compounds in PBS (pH 7.4)

Purpose: The main objective of this study is to evaluate the solubility of compounds described herein using an HPLC-UV-based method.

Methods and Procedure: Control compounds included ibuprofen as a reference for high solubility and progesterone as a reference for low solubility. Stock solutions of disclosed compounds (20 mM) are prepared in DMSO, on the same day of the experiment when feasible.

These solutions are compared with an external standard solution of known concentration via HPLC-UV To prepare the standard, 4 μL from a 20 mM compound stock solution is added to DMSO in a vial/well, and mixed with shaking at room temperature for 10 minutes. Standard buffer for assessment is PBS buffer (pH 7.4), but alternative buffers may be used, such as biologically relevant Fluids, including Simulated Gastric fluid (SGF) at pH 1.2, Fasted State Simulated Intestinal Fluid (FaSSIF) at pH 6.5, and Fed State Simulated Intestinal Fluid (FeSSIF) at pH 5.0.

An isotonic phosphate buffer (iPBS) is prepared by dissolving a phosphate buffered saline tab (Sigma-Aldrich P4417-50Tab) in 200 mL of deionized water, the final composition of the solution being 10 mM PBS, 2.7 mM KCl, and 137 mM NaCl, yielding a final pH of 7.4 at 25° C.

Samples are prepared by dispensing 8 μL from a 20 mM compound stock solution in DMSO in a vial/well in duplicate, adding 392 μL of buffer in each vial/well, and mixed by shaking at room temperature for 2 hrs. The final compound concentration is approximately 400 M, while the final concentration of DMSO is about 2%. The solutions are then filtered prior to analysis.

Concentrations are determined by comparing UV absorbance of the test solution and of the known standard solution following HPLC separation using a generic fast gradient method employing a DAD detector and UV detection at 230 and 254 nm. Concerning the HPLC Mobile phase, Phase A is a 50 mM ammonium acetate aqueous solution (pH adjusted to 7.4 with ammonia), and Phase B is acetonitrile. For data analysis, chromatographic peaks are automatically integrated, and the parameters are optimized to enable consistent integration of all chromatograms in the entire analytical run. The solubility of each compound is expressed as the ratio of compound amount in the sample test solution to the amount of compound in the standard solution, calculated from the equation "solubility of sample=peak area of sample/peak area of standard x concentration of standard."

Results and Significance: The solubility of the compounds described herein is determined and compared to reference compound MDMA. The results will show the solubility of the test compounds in one or more of PBS buffer at a pH of 7.4, SGF) at pH 1.2, Fasted State Simulated Intestinal Fluid (FaSSIF) at pH 6.5, and Fed State Simulated Intestinal Fluid (FeSSIF). The methods described herein may be adapted to evaluate solubility in any other fluid of interest. The solubility of a test compound can then be classified or characterized, for example, as a high or low solubility compound. Solubility is a key physicochemical property of a new chemical entity that can be further evaluated in a pharmacological context, such as when considering absorption.

Example 9: Evaluation of Lipophilicity by Chromatographic Hydrophobicity Index (CHI)

Purpose: Lipophilicity of compounds is evaluated using an HPLC-UV-based method.

Methods and Procedure: A CHI value is determined by comparing retention time of test compound to a linear curve based on a set of calibration compounds with known CHI values. The CHI value can be converted to a CHI Log D value using an established linear regression equation.

Reference compounds with known CHI values, including theophylline, phenyltetrazole, benzymidazole, colchicine, phenyltheophylline, acetophenone, indole, propiophenone, butyrophenone, valerophenone, are used to create a calibration line. Test compounds (10 mM) are prepared in DMSO on the same day of the experiment, when feasible. For sample preparation, 10 μL of test solution is diluted with 190 μL of a solution of Ammonium Acetate solution (50 mM) and Acetonitrile (1:1) pH 7.4, which is then mixed via shaking at room temperature for 10 minutes. Test solutions are compared with the reference compounds via HPLC-UV, as described in Example 8. The gradient is calibrated by determining the retention time of each reference compound on a reverse phase LC system at a pH of 7.4.

The relationship of CHI with retention time is "CHI=Atr+B," wherein A and B are the constants of a linear plot of CHI against their gradient retention times, and tr is the retention time.

Test compounds are analyzed on the same system as test mix. The equation generated from the calibration line for the reference compounds is then used to determine the unknown CHI value for the test compound. From the CHI value, the Log D is extrapolated according to the following equation, as described in Valko et al, 2001: Log D=0.0525×CHI pH 7.4-1.467. Log D represents the log of the partitioning of a chemical compound between the lipid and aqueous phases.

Results and Significance: The lipophilicity of the compounds described herein is determined and compared to reference compound MDMA. Lipophilicity represents the affinity of a molecule for a lipophilic environment. Differences in lipophilicity will affect the comparative absorption, distribution, metabolism, and excretion of compounds, with compounds disclosed herein demonstrating lipophilicity characteristic of drugs suitable and advantageous for human use.

Example 10: In Vitro Clearance Study in Liver Microsomes

Purpose: The objective of the study is to evaluate the in vitro metabolic stability and hepatic clearance of compounds described herein in liver microsomes. Experimentation can be conducted using liver microsomes from different organisms, for example, from humans and preclinical species, such as a rat.

Methods and Procedure: The general procedure involves incubating test compounds with liver microsomes, and subsequently detecting the compounds to determine intrinsic clearance. From the rate of depletion k (min-1), the volume of the incubation V (mL), and the amount of microsomal proteins in the incubation M (mg), clearance will be estimated. Intrinsic clearance is defined by the following equation: $CL_{int}$=k*V/M Values for $CL_{int}$ are expressed as μL/min/mg protein. Verapamil and DXM are used as positive controls for CYP3A4 and CYP2D6 isoforms, respectively, to confirm metabolic activity. The stock and working solutions are illustrated in the table below:

| Test Item | Stock Solution in DMSO | Working Solution (stock solution diluted in MeOH) |
|---|---|---|
| Disclosed compound(s) | 10 mM | 50 mM |
| Positive Controls | | |
| Verapamil | 10 mM | 50 mM |
| Dextromethorphan (DXM) | 10 mM | 50 mM |

Positive control and compounds for testing are dissolved in an appropriate solvent to obtain a 10 mM stock solution, which is diluted to achieve a final working solution, as detailed in the above table. Stock solutions are prepared at 10 mM DMSO, whereas working solutions are made by adding 5 μL 10 mM DMSO+995 μL MeOH. However, this concentration can be varied, e.g., when the test item is not soluble in the selected solvent.

Prior to experimentation, frozen liver microsomes are thawed in a water bath at 37° C. and kept on ice until use. The microsomes are then diluted with 50 mM potassium phosphate buffer pH 7.4 to a protein concentration of 0.56 mg/mL. To prepare test and control items in final incubation conditions, 5 μL of test compound and positive control working solutions are added to 445 μL of microsomes incubation mixture at 0.56 mg/mL and 50 μL of regenerating system.

As it relates to the automated incubation procedure for microsomes incubation, the following procedure is followed:

1. 150 μL of quenching solution (ACN containing an appropriate Internal Standard, i.e. Rolipram and Diclofenac for positive and negative ion mode, respectively) will be manually dispensed or dispensed by using the Hamilton system in each well of 96 deep well 1 mL plates.
2. 800-1000 μL-aliquots of NADPH regenerating system is pre-warmed at 37° C. for 5 minutes.
3. 5 μL of 50 μM test items and control will be added to 445 μL of the 0.56 mg/mL microsomes solution and the incubation mixture will be pre warmed in a 96 deep well 2 mL plate (incubation plate) at 37° C. for 5 minutes.
4. The incubation reactions will be initiated by adding 50 μL of pre-warmed NADPH regenerating system to the incubation mixtures.
5. 50 μL-aliquots will be taken from incubation mixtures at: 0, 3, 10, 15, 30, and 45 minutes.
6. Samples are centrifuged at 3,000 rpm for 10 minutes, and will be further diluted in order to optimize the analytical condition prior to the LC MS/MS or Rapid Fire-MS/MS analysis.
7. Incubations of test items are run in duplicate (n=2); positive controls are run in single (n=1).

For sample analysis, LC-MS/MS system is used to monitor test samples/control to internal standard peak area ratios as representative of test or control item concentration. Data from test item incubation are processed, giving mean values where applicable. Metabolic stability is calculated from ratio of peak area of remaining test or control item with internal standard versus time.

Peak areas for test and control items are integrated using Integrator Software from Agilent or Analyst or MultiQuant Software from AB Sciex™ and are exported to XLFit or Morphit (The Edge), which are designed to calculate in vitro metabolic stability parameters. The integrated peak areas of the test and control items at the selected time points are divided by the respective peak areas of the IS, and the percent of parent remaining is calculated by normalizing the peak area ratio of parent to IS at 0 min. Observed rate constant ($k_{obs}$) for parent degradation is calculated by determining the slope of the line of the graph of the natural log of percentage parent remaining versus time of incubation. This is scaled for the protein in incubation relative to that in the liver.

Results and Significance: Intrinsic clearance (L/min/mg protein) is determined for the compounds described herein and reference compound MDMA. Determining metabolic stability facilitates comparison of different molecules in terms of their intrinsic clearance values. The experiment described herein also provides insight into variation of clearance across different species, such as in potential pre-clinical and clinical subjects. Generally, compounds with high intrinsic clearance are likely to be cleared rapidly in vivo, minimizing their duration of action. In contrast, metabolically stable molecules with low clearance may exhibit a relatively prolonged duration of action. Compounds demonstrate optimal duration of action for drug-assisted therapy.

Example 11: In Vitro Evaluation of Membrane Permeability and Interactions with P-Glycoprotein Purpose: Compounds are screened to assess their rate of transport across a cell membrane, i.e., apparent permeability ($P_{app}$). Evaluations are also made to determine whether the compounds act as substrates for P-glycoprotein (P-gp), an efflux transporter, in MDCKII MDR1 cells.

Methods and Procedure: Experiments are designed to evaluate the apparent permeability ($P_{app}$) of test compounds at pH 7.4. Additionally, the MDCKII-MDR1 cell line (Madin-Darby Canine Kidney clone II cell line heterologously expressing the human P-glycoprotein transporter) and mock cell line MDCKII are used to determine whether a compound acted as a P-gp substrate, in the absence and in the presence of the potent P-gp inhibitor. Test control items (digoxin, metoprolol, and atenolol) and control P-gp inhibitor (GF120918) stock solution are prepared in DMSO. Bidirectional assays (Apical to Basolateral [AB] and Basolateral to Apical [BA]) are run, in both the absence and presence of P-gp inhibitor GF120918 in MDCKII-MDR1 and mock cell line MDCKII, using as transport buffer HBSSH at a pH of 7.4 (n=3).

Compounds are tested at a single concentration (i.e. at 3 or 10 μM) at one time point (i.e. 60 min). Alternative concentrations or timepoints may also be investigated. As reference compounds, digoxin (P-gp substrate), atenolol (low permeable compound) and metoprolol (high permeable compound) are included at a single concentration (e.g., 10 or 25 μM) and at single time point (e.g., 60 min). Digoxin transport is evaluated in two directions (apical-to-basolateral [AB] and basolateral-to-apical [BA]) in the absence and presence of GF120918 or in mock cells, MDCKII (n=3). Atenolol and metoprolol are only tested in the AB direction in absence of GF120918 or in mock cells, MDCKII (n=3). The integrity of the cell monolayer is evaluated after the permeability experiment using the paracellular permeability marker Lucifer yellow (LY) in the apical to basolateral direction in each well.

MDCKII or MDCKII-MDR1 cells cultivated using DMEM (high glucose, GlutaMAX™ supplemented with pyruvate, 10% FBS HI and Pen/Strep) and seeded onto microporous PET (Polyethylene Terephthalate) membranes in HTS 96-Multiwell Insert plates at a density of ~175,000-245,000 cells/$cm^2$ (25000-35000 cells/well; 50 μL/well) in DMEM medium and incubated for 3-4 days at 37° C., 5% $CO_2$. Medium is changed the day before the experiment.

Stock solutions of test items are prepared in DMSO at a concentration of 5 or 10 mM and stored at −20° C. until use. The potent P-gp inhibitor, GF120918 (stock solution 10 mM) and the reference controls digoxin, atenolol, metoprolol (stock solutions 3 or 10 mM) are prepared in DMSO and stored at −20° C. until use.

Donor working solutions of test items and reference controls will be prepared at a concentration of 10 or 25 M, diluting the stock solutions in HBSSH. Receiver working solutions contained transport buffer only. All working solutions are prepared such that the final concentration of DMSO is ≤1% (v/v). A donor working solution containing LY is also prepared in transport buffer at 100 M.

MDCKII and MDCKII-MDR1 cells are preincubated (37° C., 15 to 30 minutes) in receiver working solutions containing transport buffer on apical (A) and basolateral (B) sides. Following pre-incubation, test items and control items (digoxin) transport are measured in two directions (apical to basolateral [AB]) and basolateral to apical [BA]), and these directions are performed in triplicate sets of wells, in both the absence and presence of 10 M GF120918 or mock MDCKII cells. For [AB] directional transport, 75 μL of donor working solution is added to the A (apical) compartment and 235 μL of receiver working solution is added to the B (basolateral) compartment. For [BA] directional transport, 235 μL donor working solution with test items or reference controls is added to the B compartment and 75 μL receiver working solution is added to the A compartment. Transport of permeability reference controls, atenolol and metoprolol, are measured in one direction (apical to basolateral [AB]) (n=3).

Cells are incubated (at 37° C., with shaking) for 1 h. Samples are removed from donor solutions and transport buffer (blank samples) for t=0 samples (Co) and at the end of the incubation period, from the receptor site (basolateral compartment for A→B direction and apical compartment for B→A direction) and from donor side ($C_o$ fin). Samples are extracted by protein precipitation with acetonitrile containing rolipram (for positive ion mode) or diclofenac (negative ion mode) as generic internal standard compounds and centrifuged for 10 mins at 3,000 rpm.

Additionally, to evaluate the integrity of the cell monolayer, LY permeability is measured in one direction, A→B, at the end of incubation. Residual solutions in the apical compartment are gently removed, and 75 μL of donor working solution containing LY at 100 μM is then added to the A compartment and 235 μL of receiver working solution to the B compartment. The cells are incubated (at 37° C.) for 60 minutes.

100 μL from each sample receiver well, 100 μL/well of donor solution containing 100 M LY and 100 μL/well of Transport buffer are transferred to a 96-well clear bottom black plate. Fluorescence is measured using a fluorescence plate reader, such as the Tecan Spectrafluor plus, at Ex=485 nm, Em=535 nm.

The samples themselves are analyzed using a LC MS/MS system via discrete or cassette analysis to monitor the test item or positive control to internal standard peak area ratios as representative of the test or control item's concentrations. The rate of transport ($P_{app}$) of test items and digoxin are determined in the apical to basolateral ([AB]) and basolateral to apical ([BA]) directions in the absence and presence of GF120918, where feasible. The rate of transport (Papp) of metoprolol and atenolol will be determined in the apical to basolateral ([AB]) direction in the absence of GF120918 or mock MDCKII cells.

The efflux ratio of test items and of digoxin in the absence and presence of GF120918 or in mock MDCKII cells is then calculated. Comparing the efflux ratios generated in the presence and absence of GF120918 or in mock MDCKII cells indicated whether test items are P-gp substrates. A test item is considered to be a P-gp substrate when the efflux ratio in the absence of inhibitor is >2 and if the ratio is significantly reduced in the presence of inhibitor or in mock MDCKII cells.

Mass balance as a percentage (%) is calculated using the following equation:

$$\% \text{ Recovery} = 100 \times (CD(t) + CR(t))/C_0$$

Where CD(t) is the measured concentration in the donor well at time t (expressed as IS ratio), CR(t) is the measured concentration in the receiver well at time t (expressed as IS ratio), $C_0$ is the initial concentration in the donor solution (expressed as IS ratio). The amount of compound associated with the cells or plastic is not determined.

The percentage of cell integrity is calculated using the following equation:

$$\% \text{ Integrity} = 100 \times [1 - RFUbasolateral/RFUapical]$$

LY RFU values are normalized by background mean values. Wells are considered fully acceptable if the % Integrity is >98%, acceptable with caution for values included between 98% and 95%, and not acceptable for values <95%

Results and Significance: Apparent permeability is determined for the compounds described herein and compared to reference compound MDMA. Whether a compound acts as a P-gp substrate is also determined. Measures of permeability are widely used to understand the absorption of a compound, such as into a cell. P-gp is a transmembrane efflux transporter that is found in different tissues in the body, such as the brain and the liver. P-gp influences drug transport in various ways, including effluxing a drug from inside of a cell to the outside. Thus, permeability and P-gp substrate screening provide insight into the transportation of a compound and resultant effects on efficacy, such as in a biological system, and demonstrate suitability as a human drug.

Example 12: In Vitro Assessment of Inhibitory Activity on CYP45 Isoforms

Purpose: The objective of this study is to investigate the potential inhibitory effect of compounds described herein on CYP450 enzymes, which mediate variability in drug pharmacokinetics and, consequently, responses to treatment. Exemplary CYP45 enzyme isoforms include CYP1A2, CYP2C8, CYP2B6, CYP2C9, CYP2C19, CYP21D6, and CYP3A4.

Methods and Procedure: Recombinant human CYP45 isoenzymes are used to metabolize pro-fluorescent probe substrates to fluorescent products. $IC_{50}$ values determined from the effect of test compounds on the metabolism of these probe substrates are then used to determine inhibitory potency against CYP450 isoforms.

Exemplary chemical reagents are described below:

| Component | Supplier/Cat. Number | Storage |
|---|---|---|
| Trizma | Sigma T2663 | Store at RT |
| EDTA | Sigma E6635 | Store at RT |
| Sodium Bicarbonate | Sigma S5761 | Store at RT |
| Potassium Phosphate monobasic solution | Sigma P8709 | Store at 4° C. |
| Potassium Phosphate dibasic solution | Sigma P8584 | Store at 4° C. |
| NAPD monosodium salt | Sigma N3886 | Store at −20° C. |
| Glucose-6-phosphate disodium salt hydrate | Sigma G7250 | Store at −20° C. |
| Glucose-6-phosphate dehydrogenase | Sigma G6378 | Store at −20° C. |
| Miconazole | Sigma M3512 | Store at RT |
| DMSO | Sigma 527963 | Store at RT |

Exemplary substrates are described below:

| Component | Supplier/Cat. Number | MW |
|---|---|---|
| Ethoxyresorufin (ER) | Sigma E3763 | 249.249 |
| 7-Methoxy-4-trifluoromethyl-coumarin-3-acetic acid (FCA) | SB-355907 | 302.203 |
| 3-Butyryl-7-methoxycoumarin (BMC) | SB-363399 | 249.241 |
| 4-Methylaminomethyl-7-methoxycoumarin (MMMC) | SB-285033 | 219.239 |
| 7-Benzyloxyquinoline (7-BQ) | Sigma B5182 | 235.288 |
| Vivid DBOMF substrate | Life Technologies P2974 | 572.6 |
| Vivid BOMCC substrate | Life Technologies P2974 | 307.3 |

The test system is based on a three-step procedure with a "mix and read" format, where reaction and reading are performed at 37° C. The assays described herein measure in vitro inhibitory effects ($pC_{50}$) of compounds on the human P450 isoforms (1A2, 2B6, 2C8, 2C9, 2C19, 2D36, 3A4) expressed in recombinant microsomes. Pro-fluorescent probe substrates are metabolized to fluorescent products by the enzymes. Fluorescence is measured in kinetic mode (1 read/minutes for 10 minutes), and the fluorescence rate is calculated. Data are normalized to controls: DM represents 0% effect (i.e., no inhibition), while 10 μM of the CYP inhibitor miconazole demonstrates 100% effect (i.e., complete inhibition).

Inhibition of the fluorescent signal resulting from P450 activation indicated inhibitory activity and facilitated calculation of the compound $pIC_{50}$. A quality check is included in each compound plate, wherein the signal window is monitored by performing Z' calculations (Z'≥0.2), and the antagonist potency of internal standards is within the $pIC_{50}\pm2SD$ range. Concentration response curves (CRCs) of compounds are run on two different test occasions (n=2) by preparing serial dilutions from the same compound stock solution.

| Solutions | Components | Guidelines |
|---|---|---|
| Assay buffer | 100 mM Trizma HCl + 0.5 mM EDTA | store 4° C., shelf life: 3 months |
| Vivid Assay Buffer | Potassium Phosphate Buffer 100 mM, pH 8.0 | store 4° C., shelf life: 3 months |
| Cofactor buffer | 2% (w/v) sodium bicarbonate | store 4° C., shelf life: 3 months |
| Cofactor | 7.8 mg glucose-6-phosphate, 1.7 mg NADP, 6 Units glucose-6-phosphate dehydrogenase/mL of 2% $NaHCO_3$ | prepare fresh each time on the day of the experiment |
| Vivid Regeneration System | 333 mM Glucose-6-phosphate, 30 U/ml Glucose-6-phosphate dehydrogenase in Vivid Assay Buffer | Store at −80° C. |
| NADP | 10 mM in Vivid Assay Buffer | Store at −80° C. |
| 1A2 Substrate | 50 μM ER | Dissolve 12 μg/ml in acetonitrile |
| 2C9 Substrate | 12.5 mM FCA | Dissolve 3.67 mg/mL in acetonitrile |
| 2C19 Substrate | 2.5 mM BMC | Dissolve 0.615 mg/mL in DMSO |
| 2D6 Substrate | 2.5 mM MMMC | Dissolve 0.547 mg/mL in methanol |
| 3A4 Substrate | 2.5 mM 7-BQ | Dissolve 0.588 mg/mL in acetonitrile |

To prepare the compound plate, test compounds serial dilutions 1 to 3 are performed from a 10 mM stock solution in DMSO by Biomek FX to generate 10 point CRC with the highest concentrations in column 3 and 13.

100% DMSO is placed in column 1 and 2 and used for assay low controls. 10 mM Miconazole solution in DMSO is placed in column 23 and 24 and serves as assay high controls. 1 μL copy plates are then stamped into V-bottom drug plates at a concentration which is 200 fold the final assay concentration. The copy plates are diluted prior to the experiment with assay buffer to reach 4 times the final assay concentration (2% w/v DMSO).

A reference compound (e.g., miconazole) is included in each compound plate in row A, column 3 and 13. The reference compound is diluted and stamped together with test compounds. The final concentrations of the 10 point CRCs of test compounds in the assay plate are 5.00E-05; 1.67E-05; 5.56E-06; 1.85E-06; 6.17E-07; 2.06E-07; 6.86E-08; 2.29E-08; 7.62E-09 and 2.54E-09, respectively. All solutions are prepared immediately before the assay.

As for assay plate preparation, microsomes and substrate are mixed together according to the following table:

| Mix | 1A2/ ER | 2C9/ FCA | 2C19/ BMC | 2D6/ MMMC | 3A4HR/ 7BQ |
|---|---|---|---|---|---|
| Assay buffer (mL) | 14 | 14 | 14 | 14 | 14 |
| Microsomes (μL) (0.1 mg/mL protein) | 330 | 330 | 330 | 330 | 330 |
| Substrate (μL) | 224 | 90 | 90 | 90 | 224 |

Microsomes are added to the buffer prior to the substrate addition. The solution is carefully mixed without vortexing. 30 μL/well of the mixture is then transferred to the assay plate (384-well black plate) using a 16-channel pipette. For each P450 isoform a separate plate is prepared and labeled with a barcode.

For fluorescence measurement, 10 μL/well of the test compounds are transferred from compound plate to assay plate using Biomek FX with the appropriate protocol. The assay plate is then incubated at 37° C. for 10 minutes on a shaker to allow for the interaction between compounds and enzymes. 10 μL/well of the cofactor is then added to the assay plate using the Multidrop before placing the assay plate in the plate reader EnVision to measure fluorescence. The overall final DMSO concentration for the assay is 0.5%.

Plates are read every minute for 10 minutes according to a protocol optimized for P450 isoforms, as exemplified below.

| Assay | 1A2/ ER | 2C9/ FCA | 2C19/ BMC | 2D6/ MMMC | 3A4HR/ 7BQ |
|---|---|---|---|---|---|
| Excitation | 535 | 405 | 405 | 405 | 405 |
| Emission | 590 | 515 | 515 | 515 | 535 |
| Mirror | 50/50 | 505 FITC | 505 FITC | 505 FITC | 505 FITC |

The CYP3A4 and CYP2C8 are assayed using the Vivid CYP3A4 Baculosomes, CYP2C8 Baculosomes and Vivid DBOMF Substrate (Life Technologies, cat. P2377, PV6138 and P2974 respectively), while 2B6 is tested by Vivid CYP2B6 Baculosomes and Vivid BOMCC Substrate (Life Technologies, cat. P3028 and P2975). Test compounds are prepared as specified above.

The assay plate is prepared by preparing premix by diluting P450 Baculosomes Plus Reagent and Vivid Regeneration System in 1× Vivid CYP450 Reaction Buffer (Potassium Phosphate Buffer, 100 mM, pH 8.0). Add 8 μL/ml of P450 Baculosomes Plus Reagent and 16 μL/ml of Vivid Regeneration System to achieve the appropriate final concentrations. Mix by inversion. Dispense 30 μL of pre-mix into each well of a black, 384-well plate.

Next, 10 μL/well from the compound plate is added and incubated for 10 minutes at 37° C. on a plate shaker, while a mixture of Vivid Substrate and Vivid NADP+ in Vivid CYP450 Reaction Buffer is prepared. The reaction is started by adding 10 μL/well of the Vivid Substrate and NADP+ mixture, before transferring the plate into the fluorescent plate reader (immediately, within 2 minutes) and monitor fluorescence every minute for 10 minutes according to the specific protocol.

Regarding data analysis, the inhibition effect is expressed as a percentage. Normalization is based on the inhibition rate in the presence of 10 μM Miconazole (100% effect=C2) and inhibition rate in presence of 0.5% DMSO (0% effect=C1), according to the following formula: Y=100×[(data−C1)/(C2−C1)]. Curve fitting and $pIC_{50}$ estimations are carried out using a four-parameter logistic model.

Results and Significance: Results of the inhibitory effects, for example, represented as $IC_{50}$, of the compounds described herein are determined and compared to reference compound MDMA. Cytochrome P450 (CYP450) represents a superfamily of enzymes that exhibit metabolic activity, specifically oxidation reactions. Inhibitors of CYP450 interfere with or reduce such enzymatic activity. Some drugs are metabolized by only one CYP enzyme, while others may be metabolized by many. Comparing the results of an experiment as described herein may provide insight into potential similarities or differences in metabolism between compounds.

Example 13: In Vitro Determination of Plasma Protein Binding and Tissue Protein Binding Purpose: To determine the plasma protein binding of test compounds in rat and human specimens, including blood, brain, and lung samples, using an equilibrium dialysis assay.

Methods and Procedure: Plasma protein binding and blood tissue binding of test items (0.5 μM) is determined using biological samples from male Sprague Dawley (SD) rats and humans. Clozapine is used as a control compound for plasma protein binding and blood and brain tissue binding, as it exhibits extensive binding to plasma proteins (~97%). Dexamethasone is used as a control compound for lung tissue binding. Various biological samples are spiked with test compounds according to the methods that follow.

Preparation of Plasma or Blood Spiked with Test Compound:

An appropriate amount of test item is dissolved in DMSO (or an appropriate solvent) to produce a 10 mM solution. Further dilutions, to obtain 50 μM working solutions (WS), are then prepared using 50% acetonitrile in Milli-Q water. These 100× WS are used to spike plasma or blood to obtain a final concentration of 0.5 μM. From this initial spiking solution, control samples (n=3), referred to as T=0, are immediately extracted and used to calculate recovery of the test item.

Preparation of Brain Homogenate Spiked with Test Compound:

An appropriate amount of test item is dissolved in DMSO (or an appropriate solvent) to provide a 10 mM solution. Further dilutions, to obtain 166.7 μM working solutions (WS), are prepared using 50% acetonitrile in Milli Q water. These 100× WS are used to spike the brain homogenate to obtain a final concentration of 5 μM. From this initial spiking solution, control samples (n=3), referred to as T=0, are immediately extracted by protein precipitation. Preparation of lung homogenate spiked with test compound:

An appropriate amount of test item is dissolved in DMSO (or an appropriate solvent) to provide a 10 mM solution. Further dilutions, to obtain 71 μM working solutions (WS), are then prepared using 50% acetonitrile in MilliQ water. 71 μM WS is used to spike the lung homogenate to obtain a final concentration of 5 μM. From this initial spiking solution control samples (n=3), referred to as T=0, are immediately extracted and used to calculate the recovery of the test item. Preparation of tissue homogenate spiked with test compound:

An appropriate amount of test item is dissolved in DMSO (or an appropriate solvent) to prepare a 10 mM solution. Further dilutions, to obtain working solutions (WS), are then prepared using 50% acetonitrile in MilliQ water. WS is used to spike the tissue homogenate to obtain a final concentration of 5 μM in neat tissue. From this initial spiking solution control samples (n=3), referred to as T=0, are immediately extracted and used to calculate the recovery of the test item.

An equilibrium dialysis method is performed to determine protein binding in the various biological samples described herein. Materials are prepared and methods are in accordance with the following procedures: Membranes are prepared for use in the equilibrium dialysis experiment. by soaking in deionized water for at least 60 minutes. After this period, 20% of pure ethanol is added, and the membranes are left in this solution for at least 20 minutes. The membranes are then rinsed in Milli-Q water prior to use. To initiate the experiment, 150 μL of test item-free buffer (isotonic phosphate buffer for plasma and blood, artificial CSF buffer for brain or HBSS buffer for lung) is dispensed on one half-well of a 96-well dialyzer apparatus (HTDialysis LLC), and 150 μL of spiked matrix (plasma, blood, brain or lung) is loaded on the other half-well. Alternative volumes may be used according to the operating instructions of HTDialysis.

The artificial cerebral spinal fluid (CSF) buffer is prepared as follows, NaCl 3.652 g, KCl 93.2 mg, $MgCl_2$ 119.96 mg, $CaCl_2$ 92.61 mg, $Na_2HPO_4{*}H_2O$ 268.0 mg. These are dissolved in 0.5 L of MilliQ water, and the pH is adjusted to a pH of 7.4 with $H_3PO_4$. Dialysis buffer is prepared by dissolving 8.69 g of $Na_2HPO_4$, 1.90 g of $KH_2PO_4$, and 4.11 g of NaCl in 1 L of MilliQ water, and adjusting the pH to 7.4 with $H_3PO_4$. For equilibration, the device will be sealed and incubated (shaking for 5 hours at 37° C.). At the end of the equilibration period, 50 μL of dialysed matrix will be added to 50 μL of corresponding test item free dialysed buffer, and vice versa for buffer, such that the volume of buffer to matrix will be the same. Samples are extracted by protein precipitation with 300 μL of acetonitrile containing rolipram (for positive ionization mode) or diclofenac (for negative ionization mode) as internal standard and centrifuged for 10 minutes at 2800 rpm. Supernatants are collected (100 μL), diluted with 18% ACN in Milli Q water (200 μL).

Samples are then injected onto an HPLC MS/MS or UPLC MS/MS system. To control the integrity of the membrane after the dialysis process, the presence of protein is assessed in the buffer compartment. 5 μL of dialysed buffer will be added with 250 μL of Bio-Rad protein assay reagent (Bio-Rad) diluted 1:5 with Milli-Q water. A change in color from brown to a brilliant blue indicates protein contamination. Contaminated samples are excluded from all calculations.

Samples are analyzed in a LC-MS/MS system using an analytical method to monitor the compound to internal standard peak area ratios as representative of the compound concentrations. Protein binding, in plasma, blood, brain, and lung tissue binding will all be determined with the following formula: Afu=Buffer/x, wherein "x" may be plasma, blood, brain, or lung, and "Afu" is the apparent fraction unbound, and the other variables refer to the analyte/internal standard ratio determined in their specific compartment (buffer, plasma, blood, brain homogenate, and lung homogenate);

$$fucr = \frac{\frac{1}{D}}{\left[\left(\frac{1}{Afu} - 1\right) + \frac{1}{D}\right]},$$

wherein fucr is the fraction unbound corrected, D is the matrix dilution factor (D=1 for plasma, 2 for blood, 3 for brain, 7 for lung). % Binding=1−fucr)×100 and % Unbound=100−% Bound.

Each test item and the control compound (clozapine or dexamethasone) will be processed in n=3 replicates and average (with standard deviation) will be calculated. If the SD will be greater than 20% the median (with range) will be calculated. To validate results, % binding values for clozapine and dexamethasone must be within Ave±2SD (where Ave is calculated from historical data produced in-house).

Recovery, generally, may be determined by comparing the sum of area ratio (analyte/internal standard) determined in buffer and plasma, blood, brain or lung compartments with area ratio of the T=0 samples, a recovery value will obtained, as described in the following formula: Recovery=[(Buffer+Matrix)/T=0]×100, wherein "Buffer" is the analyte/internal standard ratio determined in buffer compartment, "Matrix" is the analyte/internal standard ratio determined in plasma, blood, brain, or lung compartment, and T=0 are the control samples.

As it relates to recovery specifically, recovery of >200 or <50 indicates that the experimental data is not valid; 50≤recovery <80 or 120<recovery ≤200 indicates that the experimental data should be met with caution, and 80≤recovery ≤120 indicate the data is valid.

Results and Significance: The results of tested compounds and reference compound MDMA are compared. The results of the study will show the protein binding of test items in various biological samples, such as blood, plasma, brain, and lung specimens of rat and/or human origin, as described herein. The binding affinity of a compound to plasma proteins and tissue influences its pharmacokinetic and pharmacodynamic properties. Generally, the free (unbound) form of a compound is available to reach a target site and exert pharmacological activity. Compounds that are more extensively bound to plasma proteins may have relatively lower volume of distribution, longer plasma half-lives, and lower clearance by both renal and hepatic routes.

Example 14: In Vitro Activity at Trace Amine-Associated Receptor 1 (TAAR1)

Purpose: To assess the activity of disclosed compounds at trace amine-associated receptor 1, a target of psychoactive substances. See, e.g., Rickli et al., Neuropsychopharmacology, 2016; 26(8), 1327-1337, Di Cara et al., Journal of Neuroscience 2011; 31(47):16928-16940; Miller et al., Journal of Neurochemistry, 116(2), 164-176; Simmler et al., Br J Pharmacol. 2013 January; 168(2): 458-470, and Simmler et al., J Pharmacol Exp Therapeutics, 2016; 357(1):134-144.

Methods: A radioligand binding assay is performed according to previously described methods, for example, by Rickli et al., Neuropsychopharmacology, 2016; 26(8), 1327-1337, using [3H] RO5166017 as a radiolabel and RO5166017 as a competitor. Briefly, membrane preparations of human embryonic kidney (HEK) 293 cells that overexpress TAAR1 receptors, for example, of human origin (Revel et al., PNAS, 2011; 108:8485-8490) are incubated with the radiolabeled selective ligand at concentrations equal to $K_d$. Ligand displacement by the compounds is then measured. Specific binding of radioligand to target receptor is defined as the difference between total binding and nonspecific binding determined in the presence of selected competitors in excess.

Results & Significance: Activation of TAAR1 has been shown to modulate monoaminergic neurotransmission. See, e.g., Revel et al., PNAS. 2011; 108(20):8485-8490. TAAR1 may be a promising target for the treatment of neuropsychiatric disorders. For example, the effects of TAAR1 activation on dopaminergic neurotransmission may provide therapeutic benefit for addiction, such as substance use disorders (Liu & Li, Front Pharmacol. 2018; 9:279).

Example 15: Human Trials

The compounds described herein are administered to human volunteers by administration means including oral solid form, such as capsule or tablet, inhaled form, and injected form, such as IM, IV, or subcutaneous administration, at a dosage selected following initial safety studies and SAD/MAD ascending dose studies, performed according to ordinary procedures therefor, for example a dosage of 15 mg, 25 mg, 50 mg, 100 mg, 125 mg, or 150 mg. Blood samples are collected at 20, 40, 60, and 200 minutes post-administration. Samples are analyzed by LCMS. Subjective effects are measured by standardized questionnaires or assessments known to those of skill, such as the Subjective Drug Effects Questionnaire (Katz et al., J Abnormal Psych., 73(1), 1-14; Waskow, and Olson, 1968); the Brief Fear of Negative Evaluation-revised (BFNE) (Carleton et al., 2006, Depression and Anxiety, 23(5), 297-303; Leary, 1983, Personality and Social Psychology bulletin, 9(3), 371-375), the Authenticity Inventory (Kernis & Goldman. 2006. Advances in experimental social psychology, 38, 283-357) as modified by Baggott et al (J Psychopharmacol. 2016, 30.4: 378-87), the Abnormal Mental States questionnaire, first published in 1998 by Adolf Dittrich, which includes three dimensions, including "Oceanic Boundlessness (OSE)," "Dread of Ego Dissolution (AIA)," and Visionary Restructuralization (VUS)," Positive and Negative Symptom Schedule-X (PANAS-X), Brief Fear of Negative Evaluation (BFNE), Visual Analog Scale Items (VAS), and Trustworthy Face Task (TFT), and such other questionnaires or assessments as will be known to those of skill. The questionnaires will illustrate that patients perceive feelings associated with subjective entactogenic effects, the intensity of which is correlated with blood levels of the compounds described herein (e.g., by measuring sera concentrations using enzyme-linked immunosorbent assay or other methods known in the art). Regarding said blood levels, samples obtained at 20, 40, 60, and 200 minutes post-administration will illustrate higher levels of target monoamines than present at baseline, indicating the compounds described herein act as at least one of a monoamine uptake inhibitor and a monoamine releasing agent in human patients, when administered using the methods disclosed herein.

Example 16: Use in an Exemplary Psychedelic-Assisted Therapy Treatment

The compounds described herein are administered in a therapeutically effective amount to a patient with at least one mental health disorder in a therapist-supervised dosing session, the at at least one mental health disorder selected from the group consisting of post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, or dissociative disorders.

Prior to the administration, the patient may be evaluated to determine whether the therapist-supervised dosing session is appropriate for the patient. The evaluation may include completing questionnaires, obtaining objective health measurements from the patient, including but not limited to weight, body temperature, heart rate (HR), respiratory rate, blood oxygenation, blood pressure (BP) and its variables, including, but not limited to: systolic (SBP), diastolic (DBP), mean arterial (MAP), and pulse (PP); continuous non-invasive beat-by-beat blood pressure (CNIBP); measurements from an electrocardiogram (ECG), including, but not limited to, RR interval or its variability, QT interval or its variability, heart rate variability (HRV) (or measured by devices other than an ECG); hemodynamic response (HR), and levels of glucose, cortisol, serotonin, dopamine, cholesterol; electroencephalography (EEG) measures such as quantitative EEG (qEEG); electrocochleogram (ECochG), electromyography (EMG), electrooculography (EOG), magnetoencephalography (MEG); electrocorticography (ECoG); magnetic resonance imaging (MRI); functional MRI (fMRI); computed tomography (CT); positron emission tomography (PET); nuclear magnetic resonance (NMR) spectroscopy or magnetic resonance spectroscopy (MSR); single-photon emission computed tomography (SPECT); near infrared spectroscopy (NIRS); event-related optical signal (EROS); computed axial tomography; diffuse optical imaging (DOI); cranial ultrasound; or functional ultrasound imaging (fUS) (together, "EEG measures"); brain derived neurotrophic factor (BDNF); genetic markers including relating to CYP enzymes or drug metabolism; genetic variation in mGluR5 or FKBP5; and others, as appreciated by those of skill. If the objective measurements obtained from the patient are within established safety standards, the patient may proceed with the dosing session, and the objective measurements also may be used to determine dose amount and other characteristics of the dosing session itself.

Dosing is performed in a quiet setting with the patient resting comfortably, and is supervised by one, or in some embodiments by two or more therapists, as part of a therapist team. The patient's eyes may be covered, and music played, to create a calming atmosphere. A therapeutically effective dose of the compounds described herein is then administered. While under the effects of the disclosed compounds, the subject may be encouraged to remain in a resting position, and to focus inwardly. Once the effects of the compounds described herein have ceased (e.g., after a duration of time where the therapy team is confident that the subject will cease to have significant subjective effectives, or that the subject otherwise will cease to have subjective effects above the threshold that, for example, may interfere with remaining daily activities or driving home), and/or the patient confirms subjective effects have ceased the patient is permitted to stand and move around. In other embodiments, the patient and the therapist may engage in psychotherapy as described herein, during the dosing session. Psychotherapy may be provided during all or part of the dosing session, such as by waiting until the subjective effects have sufficiently ceased, by providing a smaller dose to permit psychotherapy, or by administering a disclosed compound that permits or that favors psychotherapy, and engagement with the therapist over inward focus or purely individual reflection. In some embodiments, e.g., for certain relatively short-acting compounds of the invention, when compared, e.g., to MDMA, this may be after about an hour, about 90 minutes, about two hours, about 150 minutes, or after about three hours. After the duration of drug effects, they psychotherapy, if provided, and the period of free movement and further acclimatization, if necessary, the patient is discharged. The following day (i.e., roughly 24 hours after the initial dosing session) the patient may meet again with the therapy team or with a single therapist from the team or another, and undergo a psychotherapy session that recounts the experience ("integration"). Integration sessions may also occur at a later date, or be avoided altogether for certain patients or certain protocols. The patient also may participate in activities that constitute integration on his or her own, e.g., by using a software app, or may interact with a therapist via telemedicine or via a pre-recorded session, which also may be interactive.

Example 17: Use as a Medication

The disclosed compounds are prescribed, in a therapeutically effective amount, to a patient with at least one mental health disorder, the at at least one mental health disorder selected from the group consisting of post-traumatic stress disorder (PTSD), adjustment disorder, affective disorder, depression, atypical depression, postpartum depression, catatonic depression, a depressive disorder due to a medical condition, premenstrual dysphoric disorder, seasonal affective disorder, dysthymia, anxiety, phobia disorders, binge disorders, body dysmorphic disorder, alcohol or drug abuse or dependence disorders, substance-related disorders, substance-induced mood disorder, a mood disorder related to another health condition, disruptive behavior disorders, eating disorders, impulse control disorders, obsessive compulsive disorder (OCD), attention deficit hyperactivity disorder (ADHD), personality disorders, attachment disorders, or dissociative disorders.

Prior to prescribing the medication, the patient also may be evaluated to determine whether such is appropriate for the patient. The evaluation may include completing questionnaires, obtaining objective health measurements from the patient, including but not limited to weight, body temperature, heart rate, respiratory rate, blood oxygenation, BP and its variables, including, but not limited to: SBP, SBP, MAP, and PP; CNIBP; ECG measurements, including RR interval or its variability, QT interval or its variability, HRV (including measured by devices other than an ECG); hemodynamic response, and levels of glucose, cortisol, serotonin, dopamine, cholesterol; EEG measures; BDNF; genetic markers including relating to CYP enzymes or drug metabolism; genetic variation in mGluR5 or FKBP5. If the objective measurements obtained from the patient are within established safety standards known to those of skill, the patient may be prescribed the medication containing the compounds described herein, wherein the prescribed dose is appropriate for the age and weight of the patient, taking into consideration other factors known to those of skill, including but not limited to comorbidities, current medications (if any), and metabolic variations among patient populations.

To confirm a reduction in symptoms, a reduction in symptom severity, or elimination of symptoms and/or a previous diagnosis, one or more diagnostic or clinical tools is used, such as the DSM-5, one or more self-reported or observer-report surveys or questionnaires, and any one or more of the Patient Health Questionnaire 9 (PHQ-9), the Hamilton Depression Rating Scale (HAM-D); the Generalized Anxiety Disorder 7 (GAD-7), PTSD Checklist for DSM-5 (PCL-5), The Alcohol Use Disorders Identification Test (AUDIT), Binge Eating Scale (BES), Obsessive-Compulsive Inventory (OCI), the Personality Disorders Questionnaire (PDQ-IV), Dissociative Experiences Scale (DES), Drug Use Questionnaire (DAST-20), the Mood Disorder Questionnaire (MDQ), and one or more other similar questionnaires, which will be chosen based on the condition or disorder to be treated, as known to those of skill. See, e.g., Morean et al., Psychopharmacology, 227(1), 177-192. By comparing baseline responses to responses after a treatment intervention, the compound or composition of the invention is shown to be effective in the methods disclosed herein.

Example 18: Exemplary Non-Inferiority Trial of Formulations and Methods

Non-inferiority trials are performed to demonstrate that the compositions and methods herein perform no worse than at least one comparator composition (e.g., MDMA, or an alternative entactogen) or method (e.g., MDMA-assisted therapy, or drug-assisted therapy using an alternative entactogen), by more than a pre-specified amount. Such trials show that the compositions and methods of the invention are at least as useful as for treatment of a specified indication and have approximately the same efficacy as the comparator(s). In embodiments, the compositions and methods of the invention are shown to offer other benefits such as a better safety profile.

Example 19: Exemplary Equivalence Trial of Formulations and Methods

Equivalence trials are performed to demonstrate that the compositions and methods herein are at least as effective as at least one comparator composition or method (as above), within a pre-specified range. Such trials show that the compositions and methods of the invention are at least as useful for treatment of a specified indication and are at least as effective as the comparator(s). In embodiments, the compositions and methods of the invention are shown to offer other benefits, such as an improved safety profile.

Example 20: Exemplary Superiority Trial of Formulations and Methods

Superiority trials are performed to demonstrate that the compositions and methods herein perform better than at least one comparator composition or method (as above), by more than a pre-specified amount. Such trials show that the compositions and methods of the invention are more useful for treatment of a specified indication and have better efficacy than the comparator(s). In embodiments, the compositions and methods of the invention are shown to offer other benefits such as a better safety profile.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise compositions, formulations, methods, or the like disclosed; many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A compound of Formula (A), or a pharmaceutically acceptable salt thereof:

(A)

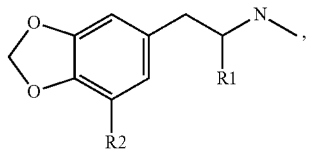

wherein:

$R^1$ is H, methyl, or ethyl; and $R^2$ is $-(CH_2)_n-CO_2Y$, where n is an integer between 0 and 4 inclusive, and Y is alkyl, cycloalkyl, aryl, or arylalkyl.

2. The compound of claim 1, wherein Y is alkyl.

3. The compound of claim 2, wherein Y is methyl.

4. The compound of claim 2, wherein $R_1$ is H.

5. The compound of claim 2, wherein $R_1$ is methyl.

6. The compound of claim 3, wherein n is 1 or 2.

7. The compound of claim 6, having the structure:

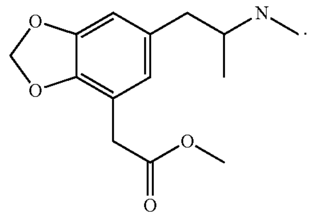 [SMILES: CNC(C)Cc1cc(CC(=O)OC)c2c(c1)OCO2]

8. The compound of claim 7, in the form of a hydrochloride salt.

9. A pharmaceutical composition, comprising the compound of claim 1, and a pharmaceutically acceptable carrier, diluent, or excipient.

10. The pharmaceutical composition of claim 9, formulated for oral, buccal, sublingual, subcutaneous, intramuscular, intravenous, or transdermal administration.

11. The pharmaceutical composition of claim 10, formulated for oral administration.

12. The pharmaceutical composition of claim 10, formulated for intravenous administration.

13. The pharmaceutical composition of claim 9, formulated in unit dosage form.

14. The pharmaceutical composition of claim 9, formulated for immediate release, controlled release, sustained release, extended release, or modified release.

15. The pharmaceutical composition of claim 9, wherein the compound has the structure:

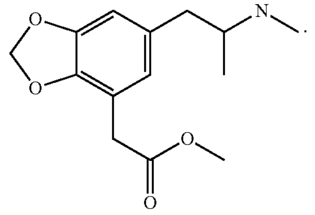 [SMILES: CNC(C)Cc1cc(CC(=O)OC)c2c(c1)OCO2]

16. The pharmaceutical composition of claim 15, wherein the compound is in the form of a hydrochloride salt.

17. The compound of claim 6, having the structure:

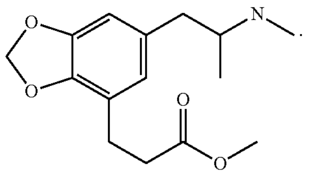 [SMILES: CNC(C)Cc1cc(CCC(=O)OC)c2c(c1)OCO2]

18. The compound of claim 17 in the form of a hydrochloride salt.

19. The pharmaceutical composition of claim 9, wherein the compound has the structure:

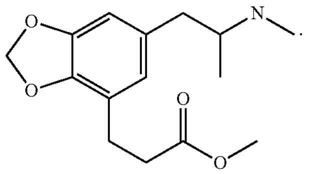 [SMILES: CNC(C)Cc1cc(CCC(=O)OC)c2c(c1)OCO2]

20. The pharmaceutical composition of claim 19, wherein the compound is in the form of a hydrochloride salt.

* * * * *